US010913710B2

(12) United States Patent
Waldmann et al.

(10) Patent No.: US 10,913,710 B2
(45) Date of Patent: Feb. 9, 2021

(54) BENZENE DISULFONAMIDE FOR THE TREATMENT OF CANCER

(71) Applicant: Max-Planck-Gesellschaft zur Forderung der Wissenschaften e.V., Munich (DE)

(72) Inventors: Herbert Waldmann, Dortmund (DE); Pablo Antonio Martin-Gago, Salamanca (ES); Sandip Murarka, West Bengal (IN); Christian Klein, Dortmund (DE); Philippe Bastiaens, Wuppertal (DE); Alfred Wittinghofer, Herdecke (DE); Eyad Kalawy Fansa, Dortmund (DE)

(73) Assignee: Max-Planck-Gesellschaft zur Forderung der Wissenschaften e.V, Munich (DE)

( * ) Notice: Subject to any disclaimer, the term of this patent is extended or adjusted under 35 U.S.C. 154(b) by 0 days.

(21) Appl. No.: 16/477,233

(22) PCT Filed: Jan. 11, 2018

(86) PCT No.: PCT/EP2018/050699
§ 371 (c)(1),
(2) Date: Jul. 11, 2019

(87) PCT Pub. No.: WO2018/130625
PCT Pub. Date: Jul. 19, 2018

(65) Prior Publication Data
US 2019/0359563 A1 Nov. 28, 2019

(30) Foreign Application Priority Data
Jan. 12, 2017 (EP) ..................... 17151296

(51) Int. Cl.
| | | |
|---|---|---|
| *C07C 311/16* | (2006.01) | |
| *C07D 221/00* | (2006.01) | |
| *C07D 239/26* | (2006.01) | |
| *C07D 241/04* | (2006.01) | |
| *C07D 401/12* | (2006.01) | |
| *C07D 405/14* | (2006.01) | |
| *C07D 493/10* | (2006.01) | |

(52) U.S. Cl.
CPC .......... *C07C 311/16* (2013.01); *C07D 221/00* (2013.01); *C07D 239/26* (2013.01); *C07D 241/04* (2013.01); *C07D 401/12* (2013.01); *C07D 405/14* (2013.01); *C07D 493/10* (2013.01)

(58) Field of Classification Search
CPC ... C07C 311/16; C07D 221/00; C07D 239/26; C07D 241/04; C07D 401/12; C07D 405/14
See application file for complete search history.

(56) References Cited

FOREIGN PATENT DOCUMENTS

| | | |
|---|---|---|
| EP | 1990335 | 11/2008 |
| WO | 2007-056099 | 5/2007 |
| WO | 2010-025308 | 4/2010 |

OTHER PUBLICATIONS

Frett et al. ChemMedChem 2013, 8, 1620-1622 (Year: 2013).*
Luo et al. Cell, 2009, 136, pp. 823-837 (Year: 2009).*
Martin-Gago et al. Angew. Chem. Int. Ed. 2017, 56, 2423-2428 (Year: 2017).*
International Search Report and Written Opinion for International Patent Application No. PCT/EP2018/050699 dated Mar. 21, 2018, 13 pages.
Papke, et al. "Identification of pyrazolopyridazinones as PDE[delta] inhibitors", Nature Communications, vol. 7, Apr. 20, 2016, p. 11360.
Zawahir et al. "Pharmacophore Guided Discovery of Small-Molecule Human Apurinic/Apyrimidinic Endonuclease 1 Inhibitors", Journal of Medicinal Chemistry, American Chemical Society, vol. 52, No. 1, Jan. 8, 2009, pp. 20-32.
Islam, et al. "The possible use of sulphonamides as insecticides Part II. Derivatives of benzene and naphthalene-disulphonamides", Egyptian Journal of Chemistry, vol. 19, No. 6, Jan. 1, 1976, pp. 969-987.
Pulla, et al. "Targeting NAMPT for Therapeutic Intervention in Cancer and Inflammation: Structure-Based Drug Design and Biological Screening", Chemical Biology & Drug Design, vol. 86, No. 4, Oct. 24, 2015, pp. 881-894.

* cited by examiner

*Primary Examiner* — Matthew P Coughlin
(74) *Attorney, Agent, or Firm* — Amin, Turocy & Watson, LLP

(57) ABSTRACT

The present invention relates to novel substituted benzene disulfonamides, as well as pharmaceutical compositions containing at least one of these substituted benzene disulfonamides together with at least one pharmaceutically acceptable carrier, excipient and/or diluent. Said substituted benzene disulfonamides are binding to the prenyl binding pocket of PDE6δ and therefore, are useful for the prophylaxis and treatment of cancer by inhibition of the binding of PDE6δ to farnesylated Ras proteins and thereby, inhibition of oncogenic Ras signaling in cells.

11 Claims, 23 Drawing Sheets

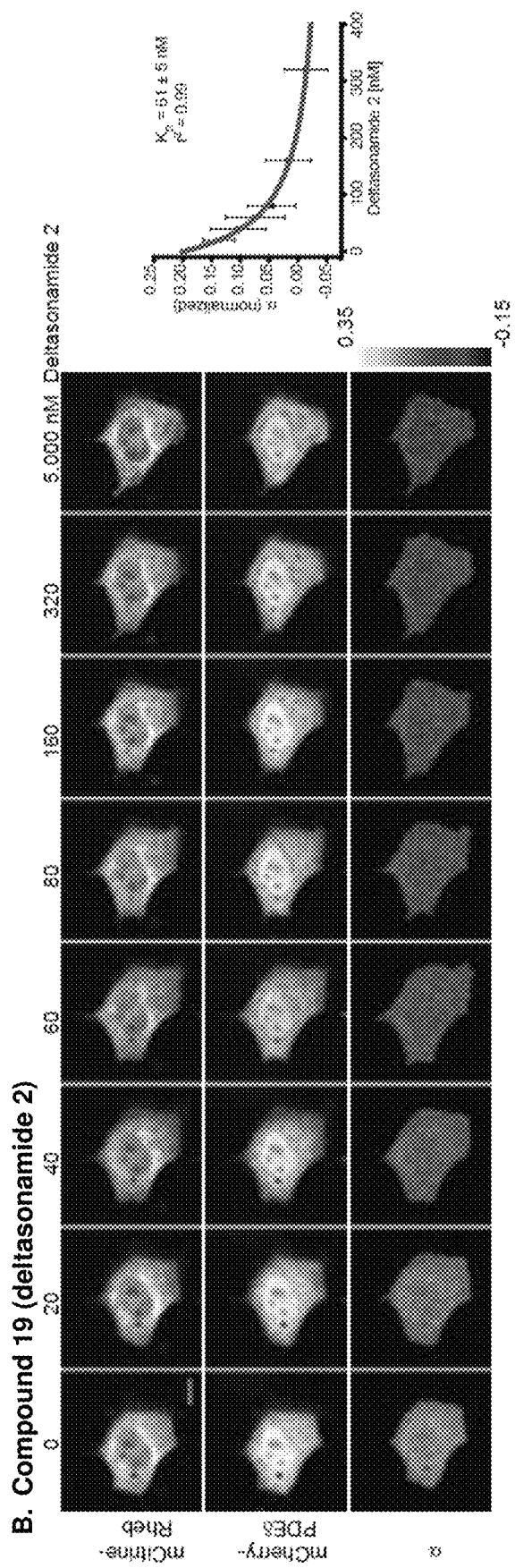

A. SW480

F. Hkh2

G.

BENZENE DISULFONAMIDE FOR THE TREATMENT OF CANCER

The present invention relates to novel substituted benzene disulfonamides, as well as pharmaceutical compositions containing at least one of these substituted benzene disulfonamides together with at least one pharmaceutically acceptable carrier, excipient and/or diluent. Said substituted benzene disulfonamides are binding to the prenyl binding pocket of PDE6δ and therefore, are useful for the prophylaxis and treatment of cancer by inhibition of the binding of PDE6δ to farnesylated Ras proteins and thereby, inhibition of oncogenic Ras signaling in cells.

BACKGROUND OF THE INVENTION

In cancer treatment, there is an ongoing need for the development of novel substances, which are effective to induce cell cycle/proliferation arrest or cell death of cancer cells. The fundamental characteristics of these cells are that the control of the cell cycle and proliferation is disturbed and they evade oncogene induced stress response and cell senescence.

Ras proteins, H-Ras, K-Ras and N-Ras are key regulators of diverse cellular processes including proliferation and differentiation. Ras proteins are normally tightly regulated by guanine nucleotide exchange factors (GEFs) promoting GDP dissociation and GTP binding and GTPase-activating proteins (GAPs) that stimulate the intrinsic GTPase activity of Ras to switch off signaling. Ras alternates between an active "on" state with a bound GTP and an inactive "off" state with a bound GDP. The active "on" state binds to and activates proteins that control growth and differentiation of cells. Aberrant Ras function is associated with proliferative disorders, cancers and tumors. Mutation at these conserved sites favors GTP binding and produces constitutive activation of Ras. Importantly, all Ras isoforms share sequence identity in all of the regions responsible for GDP/GTP binding, GTPase activity, and effector interactions suggesting functional redundancy (*Cancer Res.* 2012, 72 (10), 2457).

20 to 30% of the human tumors have activating point mutations in Ras, most frequently in K-Ras, then N-Ras, then H-Ras. These mutations all compromise the GTPase activity of Ras, preventing GAPs from promoting hydrolysis of GTP on Ras and therefore, causing Ras to accumulate in the GTP-bound, active form.

Despite substantial efforts to interfere with signaling by oncogenic Ras proteins, in particular by means of Ras-farnesyltransferase inhibitors, up to present no clinically useful drug has been found. Signaling by Ras proteins critically depends on their correct subcellular localization, which in turn is regulated by lipid modifications at their C-terminus. Thus, K-Ras, a major proto-oncogenic isoform of the Ras proteins, is S-farnesylated at its C-terminal CaaX box. Correct localization and signaling by farnesylated Ras is regulated by the prenyl binding protein PDE6δ (Phosphodiesterase 6 delta subunit, GDI-like solubilizing factor PDE6δ) (*Nature Cell Biol.* 2012, 14, 148-158).

PDE6δ was originally identified as a regulatory (noncatalytic) subunit of the enzyme phosphodiesterase 6 (PDE6). PDE6δ is referred to in the scientific literature using several different designations, including PDE delta, PDEG, PDE6δ, PDE6 delta, PDE66, PDE6D (Phosphodiesterase 6 delta) and PDED.

PDE6δ binds farnesylated Ras via the farnesylated C-terminus and has an essential role in sustaining its spatial organization and proper localization in cells, by facilitating its intracellular diffusion to enhance the kinetics of trapping at the right membrane compartment, i.e. the plasma membrane for Ras (*Nature Cell Biol.* 2012, 14, 148-158). This regulation of Ras localization and signaling by PDE6δ suggests that interfering with the PDE6δ-Ras interaction by means of small molecules might provide a novel opportunity to suppress signaling from oncogenic and normal Ras. Suppressing oncogenic Ras signaling results in halting Ras-dependent tumor proliferation.

The known PDE6δ inhibitors Deltarasin and Deltazinone 1 bind to PDE6δ with low nanomolar affinity in vitro, but show cellar activity only at micromolar concentrations (see FIG. 1; and B. Papke et al. *Nat. Commun.* 2016, 7, 11360.) The release factor Arl2 stabilizes PDE6δ and causes a discharge of the medium affinity KRas cargo (S. A. Ismail et al. *Nat. Chem. Biol.* 2011, 7, 942-949.). It is found that Arl2 also induces release of the high affinity PDE6δ inhibitors such as Deltarasina and Deltazinone 1. Therefore, a novel PDE6δ inhibitor is required, which has a high affinity to PDE6 δ and prevents efficiently release thereof by Arl2.

It is the objective of the present invention to provide novel benzene disulfonamides that can be used as pharmaceutically active agents, especially for the treatment or prophylaxis of cancers, tumors and proliferative diseases, as well as compositions comprising at least one of these compounds as pharmaceutically active agent.

The objective of the present invention is solved by the teaching of the independent claims. Further advantageous features, aspects and details of the invention are evident from the dependent claims, the description, the figures, and the examples of the present application.

DESCRIPTION OF THE INVENTION

In the present invention, it was surprisingly found that the binding of benzene disulfonamde of the general formula (I) to the prenyl binding pocket of PDE6δ induces strong inhibition of the binding of PDE6δ to Ras and oncogenic Ras signaling in cells, thereby causing inhibition of tumor cell proliferation and tumor cell death. Hence, these inventive compounds are useful for the treatment or prophylaxis of cancers, tumors and other proliferative diseases.

Thus, the present invention refers to a compound of general formula (I)

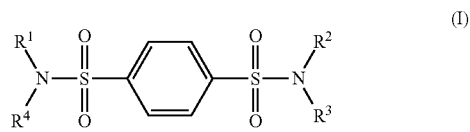

wherein
R$^1$ represents —CH$_2$—R$^5$, or —CH$_2$—CH$_2$—R$^5$;
R$^2$ represents —H, —R$^A$, —CH$_2$—R$^6$;
R$^3$ represents —R$^B$, —R$^7$, —CH$_2$—R$^7$, or —CH$_2$—CH$_2$—R$^7$; or
—NR$^2$R$^3$ represents

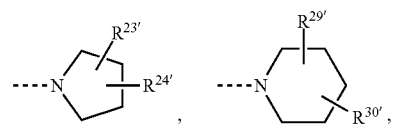

-continued
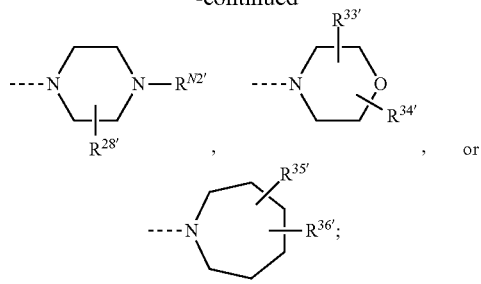
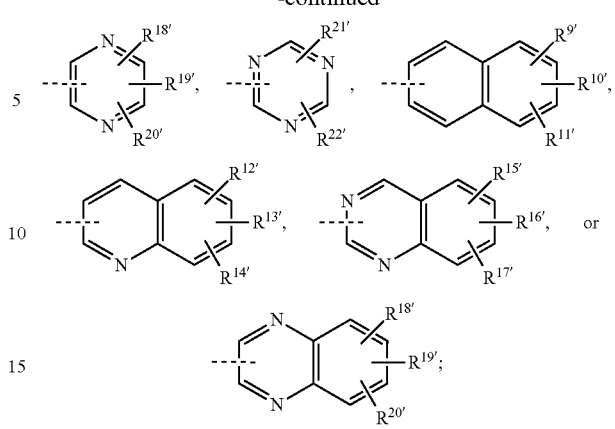
R⁴ represents —R$^C$, —R⁸, —CH$_2$—R⁸, or —CH$_2$—CH$_2$—R⁸; or
R¹ and R⁴ form together
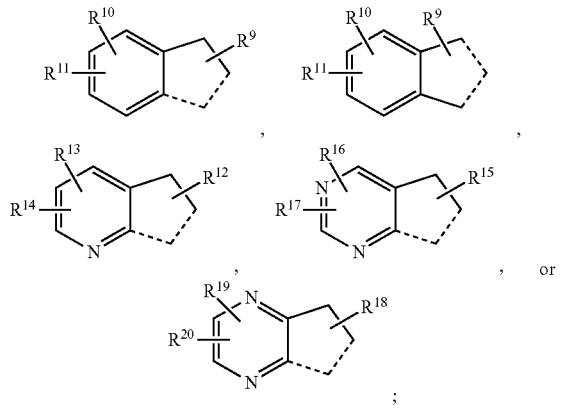
wherein R², R³ and R⁴ are not R$^A$, R$^B$, R$^C$ at the same time;
R⁵ represents
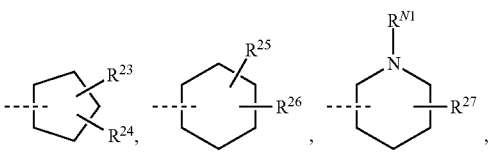
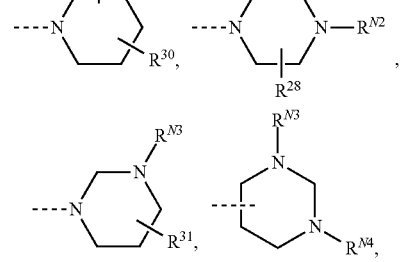
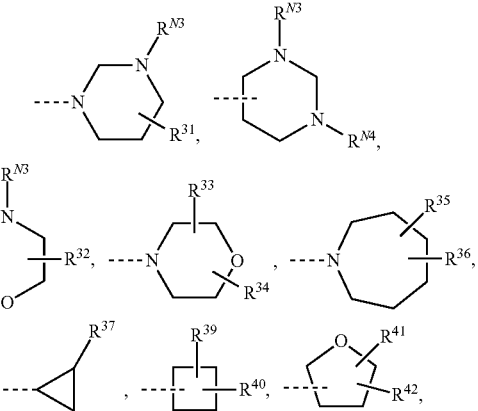
R⁶ represent
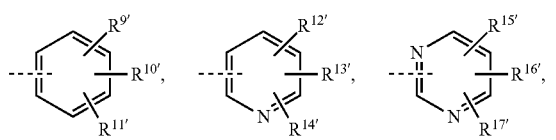
R⁷ represents
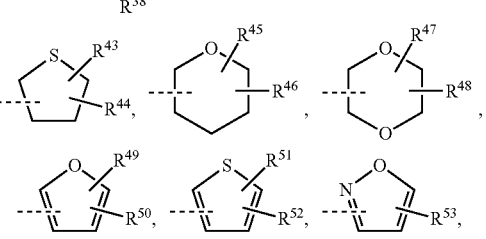
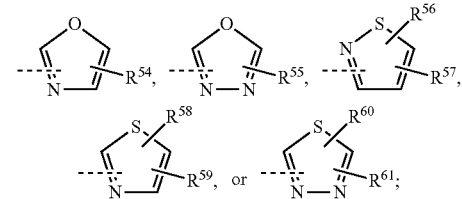
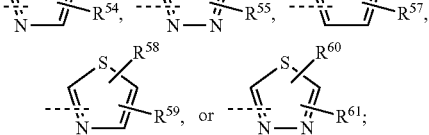

$R^8$ represents

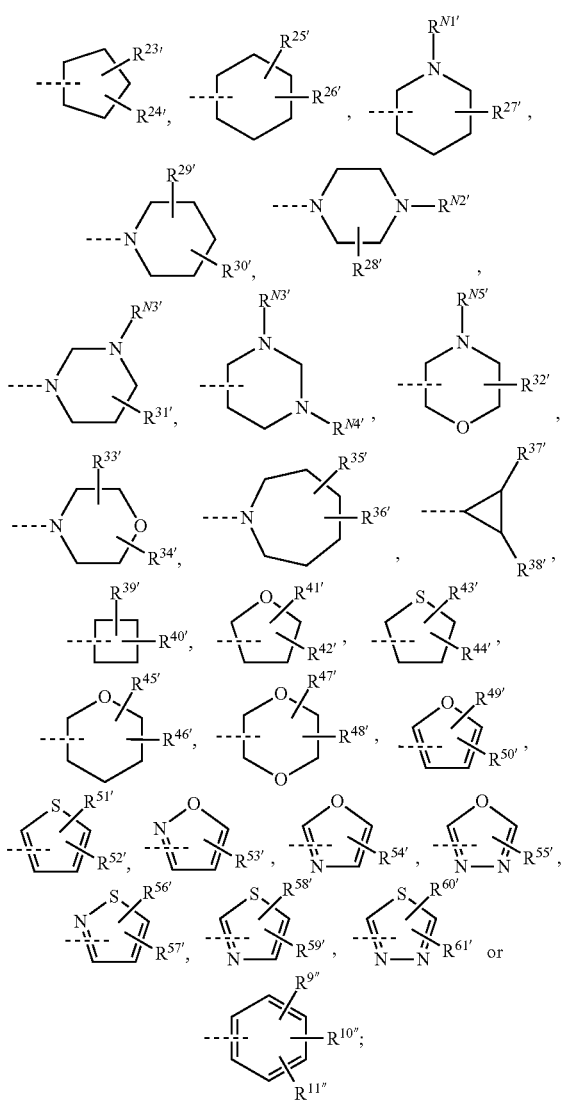

$R^A$, $R^B$, and $R^C$ represent independently of each other
—$CH_3$, —$C_2H_5$, —$C_3H_7$, —$CH(CH_3)_2$, —$C_4H_9$, —$CH(CH_3)$—$CH_2CH_3$, —$CH_2$—$CH(CH_3)_2$, —$C(CH_3)_3$, —$C_5H_{11}$, —$C_6H_{13}$, —$CH(CH_3)$—$CH_2CH_2CH_3$, —$CH_2$—$CH(CH_3)CH_2CH_3$, —$CH_2$—$CH_2CH(CH_3)_2$, —$CH(CH_3)$—$CH(CH_3)_2$, —$CH_2$—$C(CH_3)_3$, —$CH_2CH_2CH_2CH(CH_3)_2$, —$CH_2OH$, —$C_2H_4OH$, —$C_3H_6OH$, —$C_4H_8OH$, —$C_5H_{10}OH$, —$C_6H_{12}OH$, —$CH(OH)$—$CH_2OH$, —$CH_2$—$CH(OH)$—$CH_2OH$, —$CH(CH_2OH)_2$, —$CH_2$—$CH(CH_2OH)_2$, —$CH_2OSi(CH_3)_3$, —$C_2H_4OSi(CH_3)_3$, —$C_3H_6OSi(CH_3)_3$, —$C_4H_8OSi(CH_3)_3$, —$C_5H_{10}OSi(CH_3)_3$, —$C_6H_{12}OSi(CH_3)_3$, —$CH_2OSi(C_2H_5)_3$, —$C_2H_4OSi(C_2H_5)_3$, —$C_3H_6OSi(C_2H_5)_3$, —$C_4H_8OSi(C_2H_5)_3$, —$C_5H_{10}OSi(C_2H_5)_3$, —$C_6H_{12}OSi(C_2H_5)_3$, —$CH_2OSi[CH(CH_3)_2]_3$, —$C_2H_4OSi[CH(CH_3)_2]_3$, —$C_3H_6OSi[CH(CH_3)_2]_3$, —$C_4H_8OSi[CH(CH_3)_2]_3$, —$C_5H_{10}OSi[CH(CH_3)_2]_3$, —$C_6H_{12}OSi[CH(CH_3)_2]_3$, —$CH_2OSi(CH_3)_2C(CH_3)_3$, —$C_2H_4OSi(CH_3)_2C(CH_3)_3$, —$C_3H_6OSi(CH_3)_2C(CH_3)_3$, —$C_4H_8OSi(CH_3)_2C(CH_3)_3$, —$C_5H_{10}OSi(CH_3)_2C(CH_3)_3$, or —$C_6H_{12}OSi(CH_3)_2C(CH_3)_3$;

$R^9$-$R^{22}$, $R^{9'}$—$R^{22'}$ and $R^{9''}$—$R^{11''}$ represent independently of each other
—H, —F, —Cl, —Br, —I, —OH, —CN, —$NO_2$, —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, -cyclo-$C_3H_5$, —$CH_2$-cyclo-$C_3H_5$, —$CH_2F$, —$CHF_2$, —$CF_3$, —$CH_2Cl$, —$CH_2Br$, —$CH_2I$, —$CH_2$—$CH_2F$, —$CH_2$—$CHF_2$, —$CH_2$—$CF_3$, —$CH_2$—$CH_2Cl$, —$CH_2$—$CH_2Br$, —$CH_2$—$CH_2I$, —$OCH_3$, —$OC_2H_5$, —$OC_3H_7$, —$OCH(CH_3)_2$, —$OC(CH_3)_3$, —$OC_4H_9$, —$OCHF_2$, —$OCF_3$, —$OCH_2CF_3$, —$OC_2F_5$, —$OCH_2OCH_3$, —O-cyclo-$C_3H_5$, —$OCH_2$-cyclo-$C_3H_5$, —O—$C_2H_4$-cyclo-$C_3H_5$, —CHO, —$COCH_3$, —$COCF_3$, —$COC_2H_5$, —$COC_3H_7$, —$COCH(CH_3)_2$, —$COC(CH_3)_3$, —COOH, —$COOCH_3$, —$COOC_2H_5$, —$COOC_3H_7$, —$COOCH(CH_3)_2$, —$COOC(CH_3)_3$, —OOC—$CH_3$, —OOC—$CF_3$, —OOC—$C_2H_5$, —OOC—$C_3H_7$, —OOC—$CH(CH_3)_2$, —OOC—$C(CH_3)_3$, —$NH_2$, —$NHCH_3$, —$NHC_2H_5$, —$NHC_3H_7$, —$NHCH(CH_3)_2$, —$NHC(CH_3)_3$, —$N(CH_3)_2$, —$N(C_2H_5)_2$, —$N(C_3H_7)_2$, —$N[CH(CH_3)_2]_2$, —$N[C(CH_3)_3]_2$, —$CH_2NH_2$, —$CH_2NHCH_3$, —$CH_2NHC_2H_5$, —$CH_2N(CH_3)_2$, —$CH_2N(C_2H_5)_2$, —$NHCOCH_3$, —$NHCOCF_3$, —$NHCOC_2H_5$, —$NHCOC_3H_7$, —$NHCOCH(CH_3)_2$, —$NHCOC(CH_3)_3$, —$CONH_2$, —$CONHCH_3$, —$CONHC_2H_5$, —$CONHC_3H_7$, —$CONHCH(CH_3)_2$, —CONH-cyclo-$C_3H_5$, —$CONHC(CH_3)_3$, —$CON(CH_3)_2$, —$CON(C_2H_5)_2$, —$CON(C_3H_7)_2$, —$CON[CH(CH_3)_2]_2$, —$CON[C(CH_3)_3]_2$, —$SO_2NH_2$, —$SO_2NHCH_3$, —$SO_2NHC_2H_5$, —$SO_2NHC_3H_7$, —$SO_2NHCH(CH_3)_2$, —$SO_2NH$-cyclo-$C_3H_5$, —$SO_2NHC(CH_3)_3$, —$SO_2N(CH_3)_2$, —$SO_2N(C_2H_5)_2$, —$SO_2N(C_3H_7)_2$, —$SO_2N[CH(CH_3)_2]_2$, —$SO_2N[C(CH_3)_3]_2$, —$NHSO_2CH_3$, —$NHSO_2CF_3$, —$NHSO_2C_2H_5$, —$NHSO_2C_3H_7$, —$NHSO_2CH(CH_3)_2$, —$NHSO_2C(CH_3)_3$, —CH=$CH_2$, —$CH_2$—CH=$CH_2$, —$C(CH_3)$=$CH_2$, —CH=CH—$CH_3$, —C≡CH, —C≡C—$CH_3$, —$CH_2$—C≡CH, -Ph, —O-Ph, —O—$CH_2$-Ph, —$OSi(CH_3)_3$, —$OSi(C_2H_5)_3$, —$OSi(CH_3)_2C(CH_3)_3$,

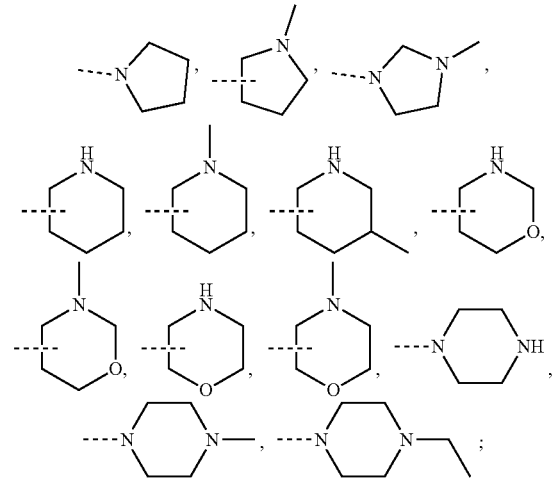

or $R^{10}$-$R^{11}$ and $R^{10'}$-$R^{11'}$ can form together any one of the following five or six rings;

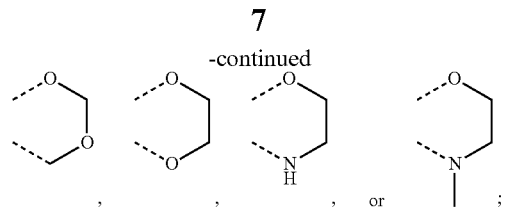
or ;

$R^{23}$-$R^{61}$ and $R^{23'}$-$R^{61'}$ represent independently of each other

—H, —F, —Cl, —OH, —CN, —NO$_2$, —CH$_3$, —C$_2$H$_5$, —C$_3$H$_7$, —CH(CH$_3$)$_2$, —CF$_3$, —OCH$_3$, —OC$_2$H$_5$, —OC$_3$H$_7$, —OCH(CH$_3$)$_2$, —OCF$_3$, —OCH$_2$OCH$_3$, —O-cyclo-C$_3$H$_5$, —OCH$_2$-cyclo-C$_3$H$_5$, —COOCH$_3$, —COOC$_2$H$_5$, —OOC—CH$_3$, —OOC—CF$_3$, —OOC—C$_2$H$_5$, —OOC—C(CH$_3$)$_3$, —NH$_2$, —NHCH$_3$, —NHC$_2$H$_5$, —NHCH(CH$_3$)$_2$, —N(CH$_3$)$_2$, —N(C$_2$H$_5$)$_2$, —CH$_2$NH$_2$, —CH$_2$NHCH$_3$, —CH$_2$NHC$_2$H$_5$, —CH$_2$N(CH$_3$)$_2$, —CH$_2$N(C$_2$H$_5$)$_2$, —NHCOCH$_3$, —NHCOCF$_3$, —CONH$_2$, —CONHCH$_3$, —CONHC$_2$H$_5$, —CON(CH$_3$)$_2$, —CON(C$_2$H$_5$)$_2$, —SO$_2$NH$_2$, —SO$_2$NHCH$_3$, —SO$_2$NHC$_2$H$_5$, —SO$_2$N(CH$_3$)$_2$, —SO$_2$N(C$_2$H$_5$)$_2$, —NHSO$_2$CH$_3$, —NHSO$_2$CF$_3$, or —NHSO$_2$C$_2$H$_5$;

$R^{N1}$-$R^{N5}$ and $R^{N1'}$-$R^{N5'}$ represent independently of each other

—H, —CH$_3$, —C$_2$H$_5$, —C$_3$H$_7$, —CH(CH$_3$)$_2$, -cyclo-C$_3$H$_5$, —COCH$_3$, —COCF$_3$, —COC(CH$_3$)$_3$, —OOC—CH$_3$, —OOC—CF$_3$, —OOC—C$_2$H$_5$, —OOC—C(CH$_3$)$_3$, —SO$_2$CH$_3$, or —SO$_2$CF$_3$;

and pharmaceutically acceptable salts thereof

Preferably, $R^5$ represent the following groups:

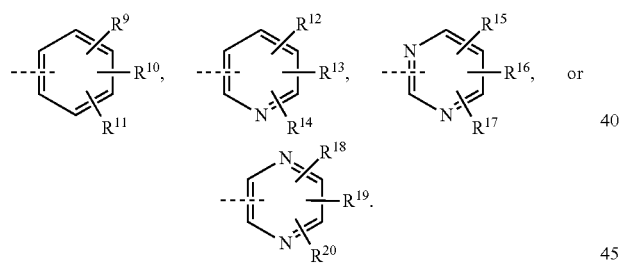

More preferably, $R^5$ represent the following groups:

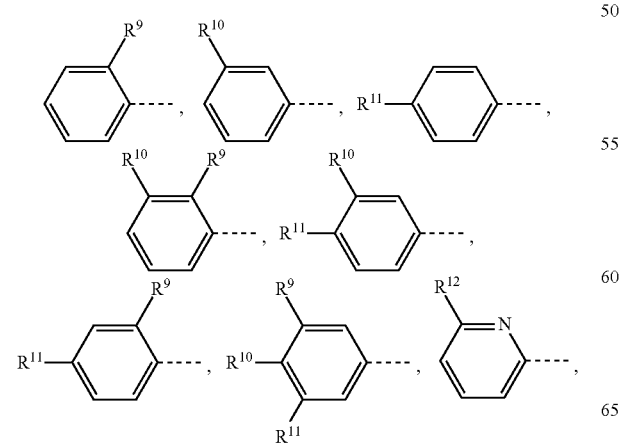

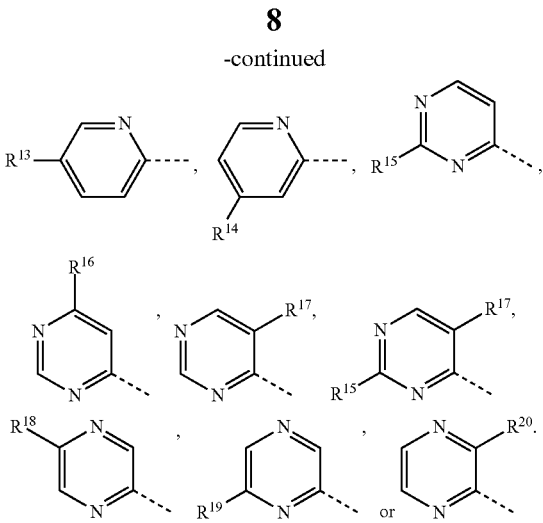

Most preferably $R^5$ represent the following groups:

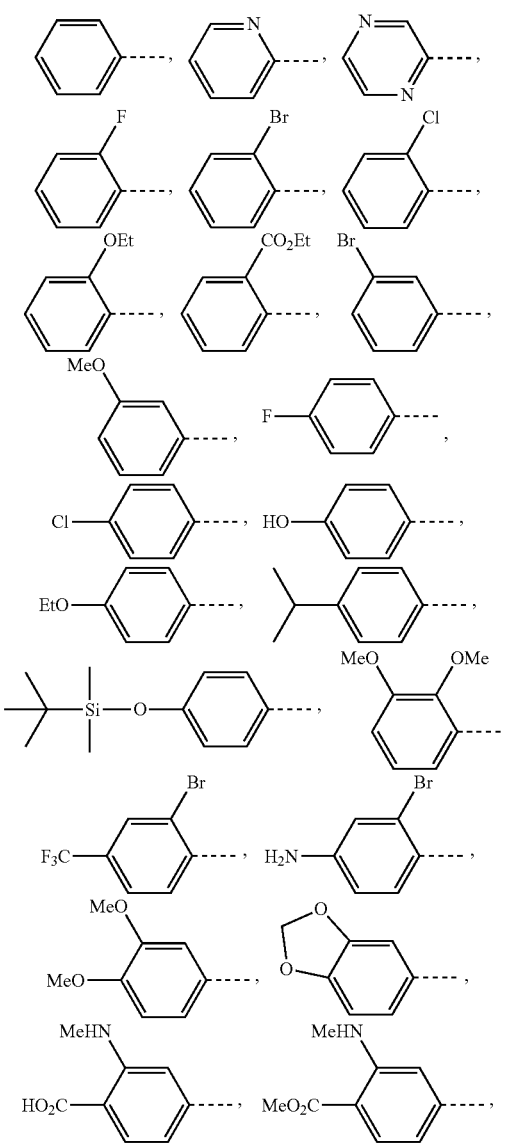

-continued
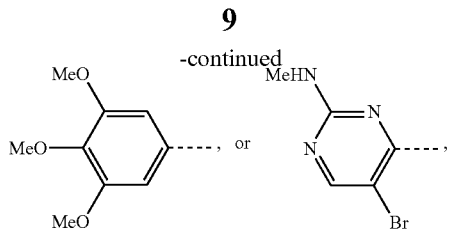
Preferably, $R^6$ represents the following groups:
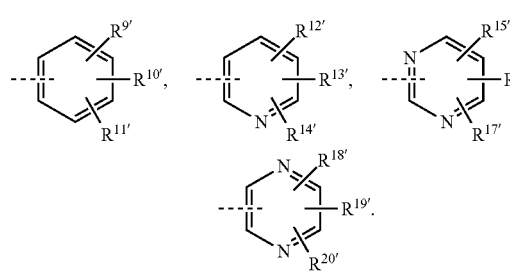
More preferably, $R^6$ represents the following groups:
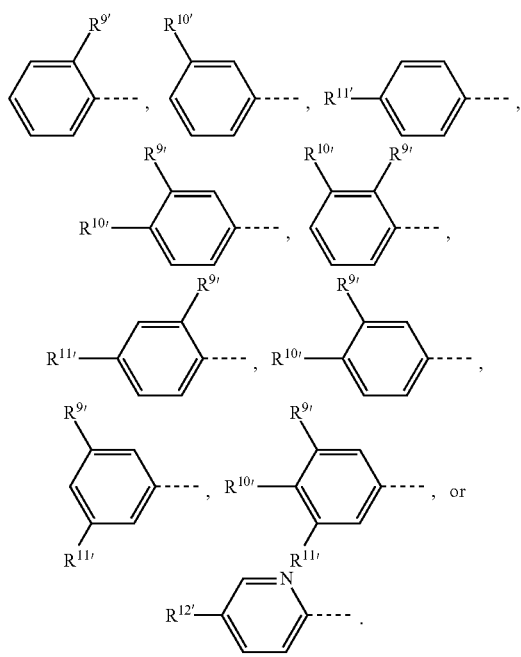
Still more preferably, $R^6$ represents the following groups:
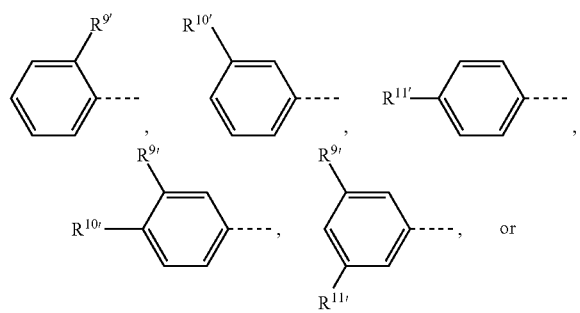
-continued
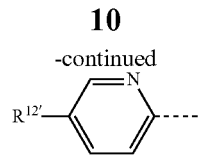
Most preferably, $R^6$ represents the following groups:
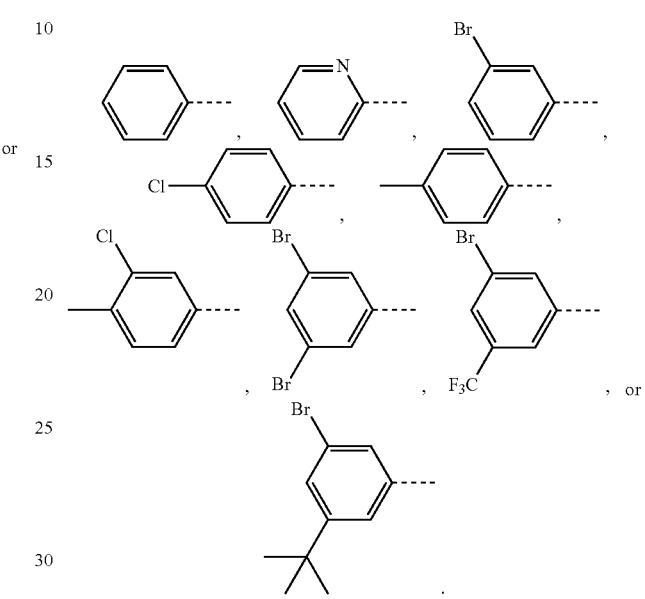
Preferably, $R^1$ and $R^4$ form together
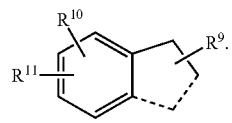
Preferably, $R^7$ represents
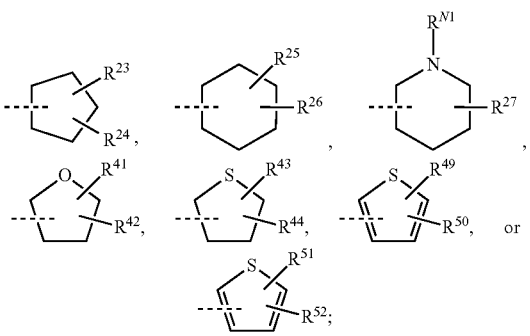
Most preferably, $R^7$ represents
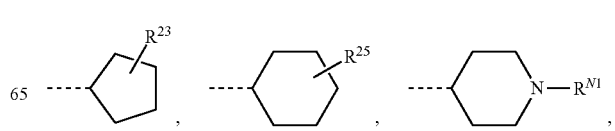

-continued

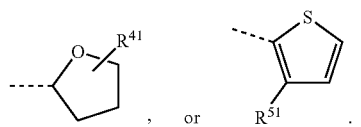

Most preferably, R⁷ represents

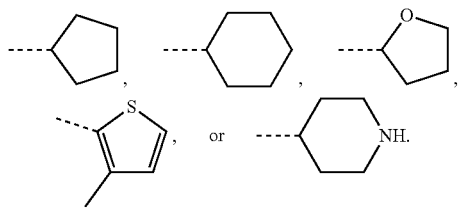

Preferably, R⁸ represents

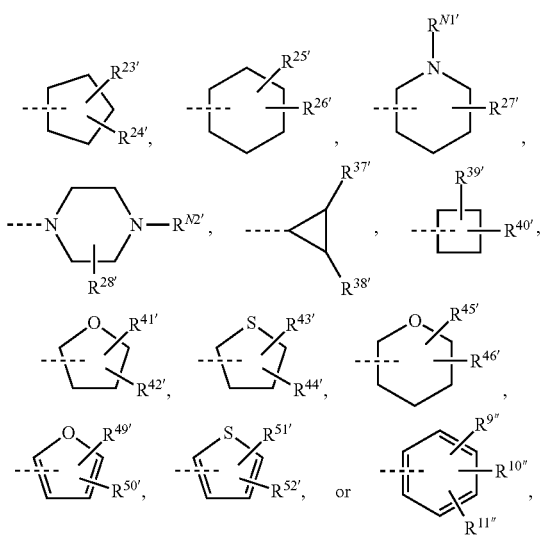

More preferably

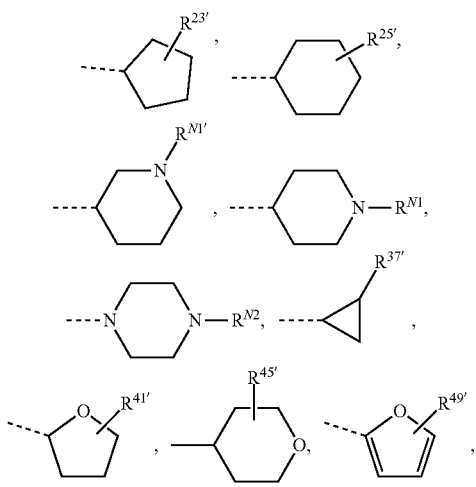

-continued

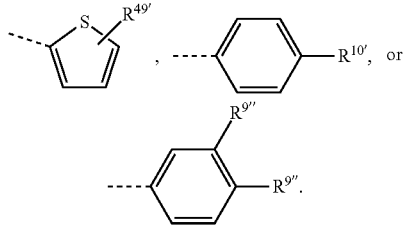

Still more preferably,

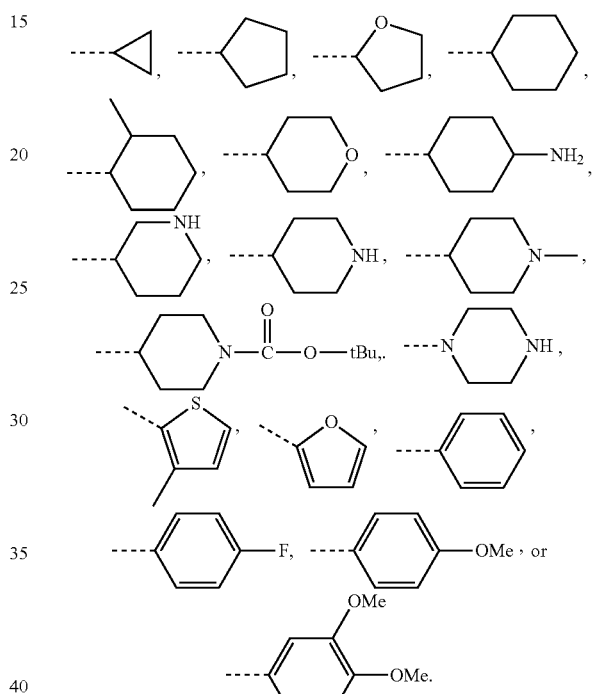

Preferably, $R^C$ represent

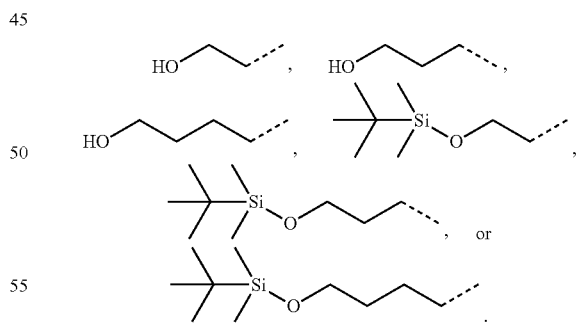

Preferably, $R^9$-$R^{22}$, $R^{9'}$-$R^{22'}$ and $R^{9'''}$-$R^{11'''}$ represent independently of each other
—H, —F, —Cl, —Br, —OH, —CH₃, —C₂H₅, —C₃H₇, —CH(CH₃)₂, —C(CH₃)₃, —CF₃, —OCH₃, —OC₂H₅, —OC₃H₇, —OCH(CH₃)₂, —OCHF₂, —OCF₃, —COOH, —COOCH₃, —COOC₂H₅, —NH₂, —NHCH₃, —NHC₂H₅, —N(CH₃)₂, —N(C₂H₅)₂, or —OSi(CH₃)₂C(CH₃)₃.

In an embodiment the present invention refers to a compound of the formula (I):

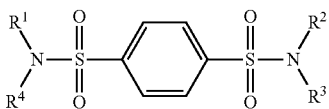
(I)

wherein
R¹ represents —CH₂—R⁵;
R² represents —CH₂—R⁶;
R³ represents —R⁷, —CH₂—R⁷, or —CH₂—CH₂—R⁷;
R⁴ represents —R⁸, —CH₂—R⁸, or —CH₂—CH₂—R⁸;
R⁵ represents

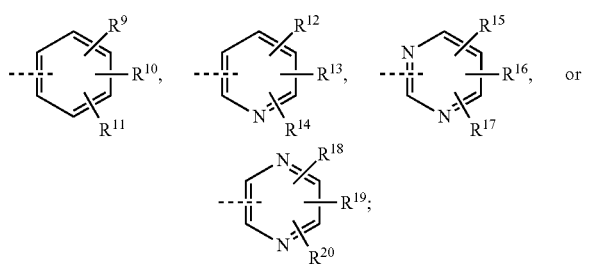

R⁶ represents

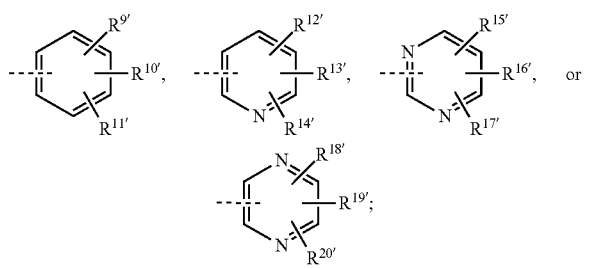

R⁷ represents

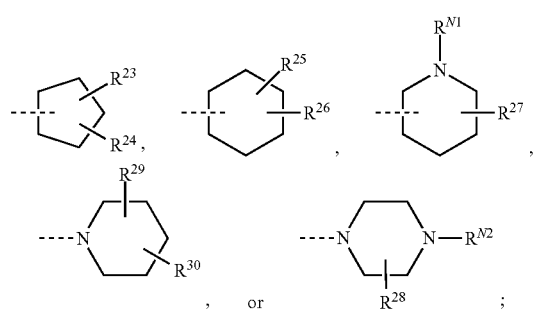

R⁸ represents

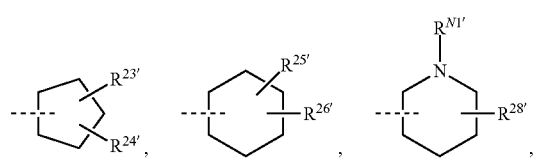

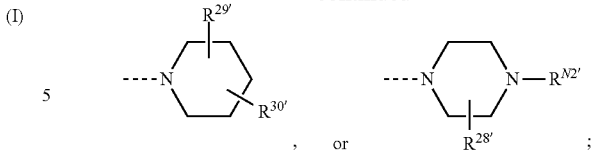

$R^9$-$R^{20}$ and $R^{9'}$-$R^{20'}$ represent independently of each other
—H, —F, —Cl, —Br, —I, —OH, —CN, —NO₂, —CH₃, —C₂H₅, —C₃H₇, —CH(CH₃)₂, —C₄H₉, —CH₂—CH(CH₃)₂, —CH(CH₃)—C₂H₅, —C(CH₃)₃, -cyclo-C₃H₅, —CH₂-cyclo-C₃H₅, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, —OCH₃, —OC₂H₅, —OC₃H₇, —OCH(CH₃)₂, —OC(CH₃)₃, —OC₄H₉, —OCHF₂, —OCF₃, —OCH₂CF₃, —OC₂F₅, —OCH₂OCH₃, —O-cyclo-C₃H₅, —OCH₂-cyclo-C₃H₅, —O—C₂H₄-cyclo-C₃H₅, —CHO, —COCH₃, —COCF₃, —COC₂H₅, —COC₃H₇, —COCH(CH₃)₂, —COC(CH₃)₃, —COOH, —COOCH₃, —COOC₂H₅, —COOC₃H₇, —COOCH(CH₃)₂, —COOC(CH₃)₃, —OOC—CH₃, —OOC—CF₃, —OOC—C₂H₅, —OOC—C₃H₇, —OOC—CH(CH₃)₂, —OOC—C(CH₃)₃, —NH₂, —NHCH₃, —NHC₂H₅, —NHC₃H₇, —NHCH(CH₃)₂, —NHC(CH₃)₃, —N(CH₃)₂, —N(C₂H₅)₂, —N(C₃H₇)₂, —N[CH(CH₃)₂]₂, —N[C(CH₃)₃]₂, —CH₂NH₂, —CH₂NHCH₃, —CH₂NHC₂H₅, —CH₂N(CH₃)₂, —CH₂N(C₂H₅)₂, —NHCOCH₃, —NHCOCF₃, —NHCOC₂H₅, —NHCOC₃H₇, —NHCOCH(CH₃)₂, —NHCOC(CH₃)₃, —CONH₂, —CONHCH₃, —CONHC₂H₅, —CONHC₃H₇, —CONHCH(CH₃)₂, —CONH-cyclo-C₃H₅, —CONHC(CH₃)₃, —CON(CH₃)₂, —CON(C₂H₅)₂, —CON(C₃H₇)₂, —CON[CH(CH₃)₂]₂, —CON[C(CH₃)₃]₂, —SO₂NH₂, —SO₂NHCH₃, —SO₂NHC₂H₅, —SO₂NHC₃H₇, —SO₂NHCH(CH₃)₂, —SO₂NH-cyclo-C₃H₅, —SO₂NHC(CH₃)₃, —SO₂N(CH₃)₂, —SO₂N(C₂H₅)₂, —SO₂N(C₃H₇)₂, —SO₂N[CH(CH₃)₂]₂, —SO₂N[C(CH₃)₃]₂, —NHSO₂CH₃, —NHSO₂CF₃, —NHSO₂C₂H₅, —NHSO₂C₃H₇, —NHSO₂CH(CH₃)₂, —NHSO₂C(CH₃)₃, —CH=CH₂, —CH₂—CH=CH₂, —C(CH₃)=CH₂, —CH=CH—CH₃, —C≡CH, —C≡C—CH₃, —CH₂—C≡CH, -Ph, —O-Ph, —O—CH₂-Ph, —OSi(CH₃)₃, —OSi(C₂H₅)₃, —OSi(CH₃)₂C(CH₃)₃,

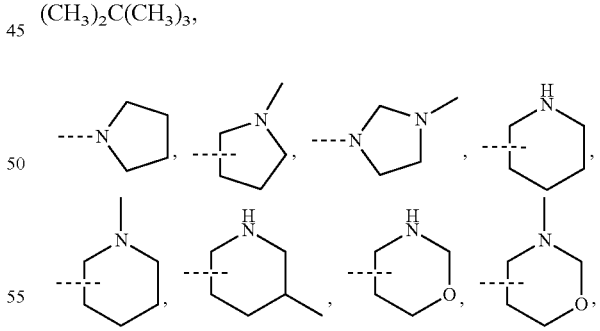

$R^{23}$-$R^{30}$ and $R^{23'}$-$R^{30'}$ represent independently of each other

—H, —F, —Cl, —OH, —CN, —NO$_2$, —CH$_3$, —C$_2$H$_5$, —C$_3$H$_7$, —CH(CH$_3$)$_2$, —CF$_3$, —OCH$_3$, —OC$_2$H$_5$, —OC$_3$H$_7$, —OCH(CH$_3$)$_2$, —OCF$_3$, —OCH$_2$OCH$_3$, —O-cyclo-C$_3$H$_5$, —OCH$_2$-cyclo-C$_3$H$_5$, —COOCH$_3$, —COOC$_2$H$_5$, —OOC—CH$_3$, —OOC—CF$_3$, —OOC—C$_2$H$_5$, —OOC—C(CH$_3$)$_3$, —NH$_2$, —NHCH$_3$, —NHC$_2$H$_5$, —NHCH(CH$_3$)$_2$, —N(CH$_3$)$_2$, —N(C$_2$H$_5$)$_2$, —CH$_2$NH$_2$, —CH$_2$NHCH$_3$, —CH$_2$NHC$_2$H$_5$, —CH$_2$N(CH$_3$)$_2$, —CH$_2$N(C$_2$H$_5$)$_2$, —NHCOCH$_3$, —NHCOCF$_3$, —CONH$_2$, —CONHCH$_3$, —CONHC$_2$H$_5$, —CON(CH$_3$)$_2$, —CON(C$_2$H$_5$)$_2$, —SO$_2$NH$_2$, —SO$_2$NHCH$_3$, —SO$_2$NHC$_2$H$_5$, —SO$_2$N(CH$_3$)$_2$, —SO$_2$N(C$_2$H$_5$)$_2$, —NHSO$_2$CH$_3$, —NHSO$_2$CF$_3$, or —NHSO$_2$C$_2$H$_5$;

$R^{N1}$, $R^{N1'}$, $R^{N2}$, and $R^{N2'}$ represent independently of each other
—H, —CH$_3$, —C$_2$H$_5$, —C$_3$H$_7$, —CH(CH$_3$)$_2$, -cyclo-C$_3$H$_5$, —COCH$_3$, —COCF$_3$, —COC(CH$_3$)$_3$, —OOC—CH$_3$, —OOC—CF$_3$, —OOC—C$_2$H$_5$, —OOC—C(CH$_3$)$_3$, —SO$_2$CH$_3$, or —SO$_2$CF$_3$;

or pharmaceutically acceptable salts thereof.

In one embodiment, the present invention is directed to the compound of the formula (I), wherein
$R^1$ represents —CH$_2$—R$^5$;
$R^2$ represents —CH$_2$—R$^6$;
$R^3$ represents —R$^7$, —CH$_2$—R$^7$, or —CH$_2$—CH$_2$—R$^7$,
$R^4$ represents —R$^8$, —CH$_2$—R$^8$, or —CH$_2$—CH$_2$—R$^8$;
$R^5$ is

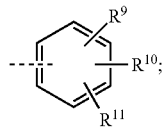

$R^6$ is

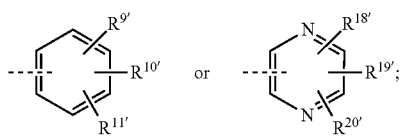

and
$R^7$-$R^8$, $R^9$-$R^{11}$, $R^{9'''}$-$R^{11'}$ and $R^{18'}$-$R^{20'}$ have the same meanings as defined above.

In one embodiment, the present invention is directed to the compound of the formula (I), wherein
$R^1$ represents —CH$_2$—R$^5$;
$R^2$ represents —CH$_2$—R$^6$;
$R^3$ represents —R$^7$, —CH$_2$—R$^7$, or —CH$_2$—CH$_2$—R$^7$,
$R^4$ represents —R$^8$, —CH$_2$—R$^8$, or —CH$_2$—CH$_2$—R$^8$;
$R^5$ is

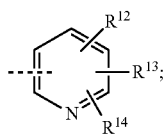

$R^6$ is

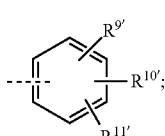

and
$R^7$-$R^8$, $R^{12}$-$R^{14}$ and $R^{9'}$-$R^{11'}$ have the same meanings as defined above.

In one embodiment, the present invention is directed to the compound of the formula (I), wherein
$R^1$ represents —CH$_2$—R$^5$;
$R^2$ represents —CH$_2$—R$^6$;
$R^3$ represents —R$^7$, —CH$_2$—R$^7$, or —CH$_2$—CH$_2$—R$^7$,
$R^4$ represents —R$^8$, —CH$_2$—R$^8$, or —CH$_2$—CH$_2$—R$^8$;
$R^5$ is

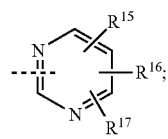

$R^6$ is

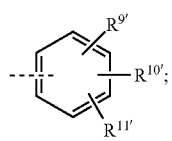

and
$R^7$-$R^8$, $R^{9'}$-$R^{11'}$ and $R^{15}$-$R^{17}$ have the same meanings as defined above.

In one embodiment, the present invention is directed to the compound of the formula (I), wherein
$R^1$ represents —CH$_2$—R$^5$;
$R^2$ represents —CH$_2$—R$^6$;
$R^3$ represents —R$^7$, —CH$_2$—R$^7$, or —CH$_2$—CH$_2$—R$^7$,
$R^4$ represents —R$^8$, —CH$_2$—R$^8$, or —CH$_2$—CH$_2$—R$^8$;
$R^5$ is

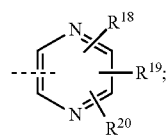

$R^6$ is

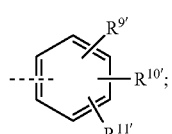

and
$R^7$-$R^8$, $R^{9'}$-$R^{11'}$ and $R^{18}$-$R^{20}$ have the same meanings as defined above.

In one embodiment, the present invention is directed to the compound of the formula (I), wherein
$R^1$ represents —CH$_2$—R$^5$;
$R^2$ represents —CH$_2$—R$^6$;
$R^3$ is —R$^7$, or —CH$_2$—R$^7$;

$R^4$ is —$R^8$; $R^7$ is

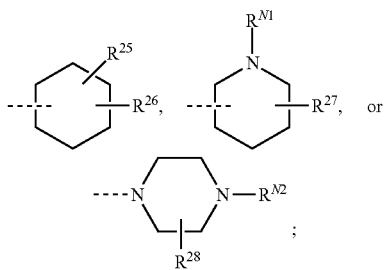

$R^8$ is

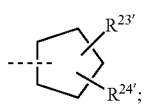

and $R^5$-$R^6$, $R^{23'}$-$R^{24'}$, $R^{25}$-$R^{28}$ and $R^{N1}$-$R^{N2}$ have the same meanings as defined above.

Preferred is the compound of the formula (II)

(II)

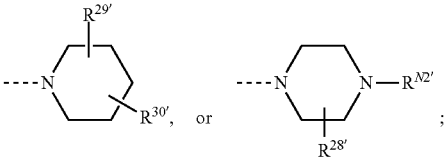

wherein
$A^1$, $B^1$, $A^2$, and $R^2$ represent independently of each other CH or N;
$R^3$ represents —$R^7$;
$R^4$ represents —$CH_2$—$R^8$, or —$CH_2$—$CH_2$—$R^8$;
$R^7$ represents

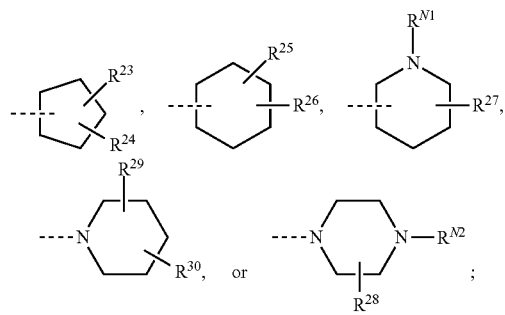

$R^8$ represents

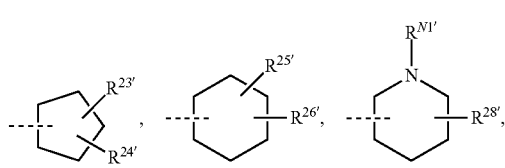

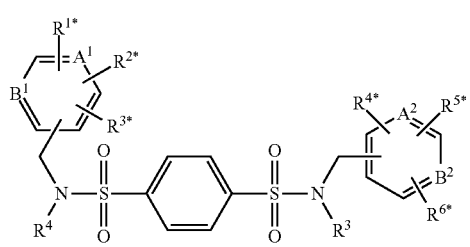

$R^{1*}$, $R^{2*}$, $R^{3*}$, $R^{4*}$, $R^{5*}$, and $R^{6*}$ represent independently of each other
—H, —F, —Cl, —Br, —I, —OH, —CN, —$NO_2$, —$CH_3$, —$C_2H_5$, —$C_3H_7$, —$CH(CH_3)_2$, —$C_4H_9$, —$CH_2$—CH($CH_3$)$_2$, —CH($CH_3$)—$C_2H_5$, —C($CH_3$)$_3$, -Cyclo-$C_3H_5$, —$CH_2$-cyclo-$C_3H_5$, —$CH_2F$, —$CHF_2$, —$CF_3$, —$CH_2Cl$, —$CH_2Br$, —$CH_2I$, —$CH_2$—$CH_2F$, —$CH_2$—$CHF_2$, —$CH_2$—$CF_3$, —$CH_2$—$CH_2Cl$, —$CH_2$—$CH_2Br$, —$CH_2$—$CH_2I$, —$OCH_3$, —$OC_2H_5$, —$OC_3H_7$, —$OCH(CH_3)_2$, —OC($CH_3$)$_3$, —$OC_4H_9$, —$OCHF_2$, —$OCF_3$, —$OCH_2CF_3$, —$OC_2F_5$, —$OCH_2OCH_3$, —O-cyclo-$C_3H_5$, —$OCH_2$-cyclo-$C_3H_5$, —O—$C_2H_4$-cyclo-$C_3H_5$, —CHO, —$COCH_3$, —$COCF_3$, —$COC_2H_5$, —$COC_3H_7$, —COCH($CH_3$)$_2$, —COC($CH_3$)$_3$, —COOH, —$COOCH_3$, —$COOC_2H_5$, —$COOC_3H_7$, —COOCH($CH_3$)$_2$, —COOC($CH_3$)$_3$, —OOC—$CH_3$, —OOC—$CF_3$, —OOC—$C_2H_5$, —OOC—$C_3H_7$, —OOC—CH($CH_3$)$_2$, —OOC—C($CH_3$)$_3$, —$NH_2$, —$NHCH_3$, —$NHC_2H_5$, —$NHC_3H_7$, —NHCH($CH_3$)$_2$, —NHC($CH_3$)$_3$, —N($CH_3$)$_2$, —N($C_2H_5$)$_2$, —N($C_3H_7$)$_2$, —N[CH($CH_3$)$_2$]$_2$, —N[C($CH_3$)$_3$]$_2$, —$CH_2NH_2$, —$CH_2NHCH_3$, —$CH_2NHC_2H_5$, —$CH_2N(CH_3)_2$, —$CH_2N$($C_2H_5$)$_2$, —$NHCOCH_3$, —$NHCOCF_3$, —$NHCOC_2H_5$, —$NHCOC_3H_7$, —NHCOCH($CH_3$)$_2$, —NHCOC($CH_3$)$_3$, —$CONH_2$, —$CONHCH_3$, —$CONHC_2H_5$, —$CONHC_3H_7$, —CONHCH($CH_3$)$_2$, —CONH-cyclo-$C_3H_5$, —CONHC($CH_3$)$_3$, —CON($CH_3$)$_2$, —CON($C_2H_5$)$_2$, —CON($C_3H_7$)$_2$, —CON[CH($CH_3$)$_2$]$_2$, —CON[C($CH_3$)$_3$]$_2$, —$SO_2NH_2$, —$SO_2NHCH_3$, —$SO_2NHC_2H_5$, —$SO_2NHC_3H_7$, —$SO_2$NHCH($CH_3$)$_2$, —$SO_2$NH-cyclo-$C_3H_5$, —$SO_2$NHC($CH_3$)$_3$, —$SO_2N(CH_3)_2$, —$SO_2N(C_2H_5)_2$, —$SO_2N(C_3H_7)_2$, —$SO_2$N[CH($CH_3$)$_2$]$_2$, —$SO_2$N[C($CH_3$)$_3$]$_2$, —$NHSO_2CH_3$, —$NHSO_2CF_3$, —$NHSO_2C_2H_5$, —$NHSO_2C_3H_7$, —$NHSO_2$CH($CH_3$)$_2$, —$NHSO_2$C($CH_3$)$_3$, —CH=$CH_2$, —$CH_2$—CH=$CH_2$, —C($CH_3$)=$CH_2$, —CH=CH—$CH_3$, —C≡CH, —C≡C—$CH_3$, —$CH_2$—C≡CH, -Ph, —O-Ph, —O—$CH_2$-Ph, —OSi($CH_3$)$_3$, —OSi($C_2H_5$)$_3$, or —OSi($CH_3$)$_2$C($CH_3$)$_3$;

$R^{23}$-$R^{30}$ and $R^{23'}$-$R^{30'}$ represent independently of each other
—H, —F, —Cl, —OH, —CN, —$NO_2$, —$CH_3$, —$C_2H_5$, —$C_3H_7$, —CH($CH_3$)$_2$, —$CF_3$, —$OCH_3$, —$OC_2H_5$, —$OC_3H_7$, —OCH($CH_3$)$_2$, —$OCF_3$, —$OCH_2OCH_3$, —O-cyclo-$C_3H_5$, —$OCH_2$-cyclo-$C_3H_5$, —$COOCH_3$, —$COOC_2H_5$, —OOC—$CH_3$, —OOC—$CF_3$, —OOC—$C_2H_5$, —OOC—C($CH_3$)$_3$, —$NH_2$, —$NHCH_3$, —$NHC_2H_5$, —NHCH($CH_3$)$_2$, —N($CH_3$)$_2$, —N($C_2H_5$)$_2$, —$CH_2NH_2$, —$CH_2NHCH_3$, —$CH_2NHC_2H_5$, —$CH_2N(CH_3)_2$, —$CH_2N$($C_2H_5$)$_2$, —$NHCOCH_3$, —$NHCOCF_3$, —$CONH_2$, —$CONHCH_3$, —$CONHC_2H_5$, —$CON(CH_3)_2$, —CON($C_2H_5$)$_2$, —$SO_2NH_2$, —$SO_2NHCH_3$, —$SO_2NHC_2H_5$, —$SO_2N(CH_3)_2$, —$SO_2N(C_2H_5)_2$, —$NHSO_2CH_3$, —$NHSO_2CF_3$, or —$NHSO_2C_2H_5$;

$R^{N1}$, $R^{N1'}$, $R^{N2}$, and $R^{N2'}$ represent independently of each other
—H, —$CH_3$, —$C_2H_5$, —$C_3H_7$, —CH($CH_3$)$_2$, -cyclo-$C_3H_5$, —$COCH_3$, —$COCF_3$, —COC($CH_3$)$_3$, —OOC—$CH_3$, —OOC—$CF_3$, —OOC—$C_2H_5$, —OOC—C($CH_3$)$_3$, —$SO_2CH_3$, or —$SO_2CF_3$.

More preferred is the compound of any one of the formulae (III-1)-(III-8)

(III-1)
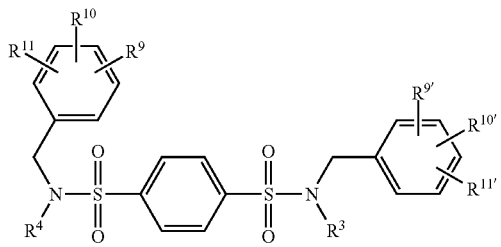
(III-2)
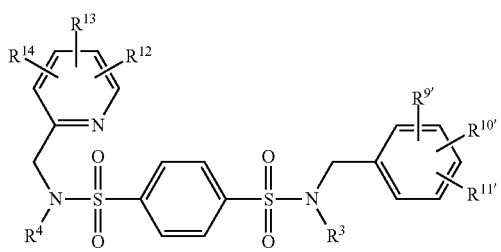
(III-3)
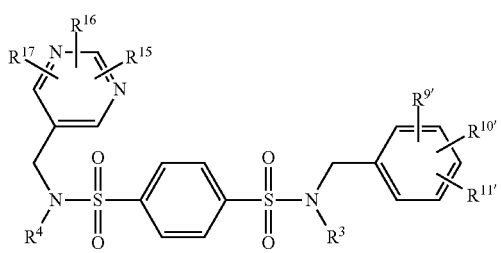
(III-4)
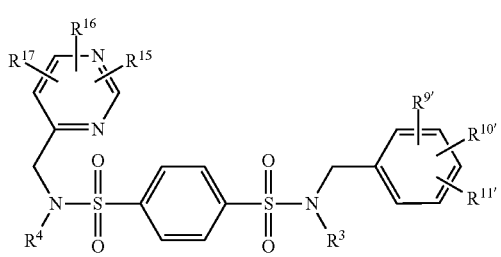
(III-5)
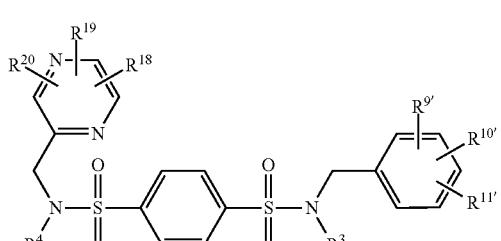
(III-6)
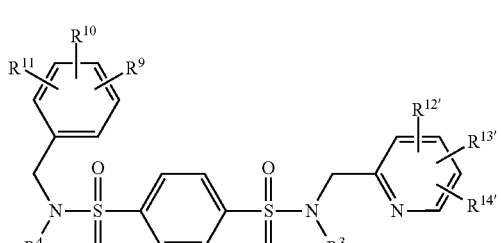
(III-7)
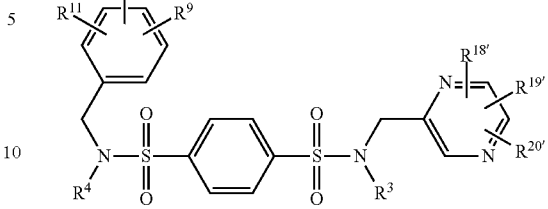
(III-8)
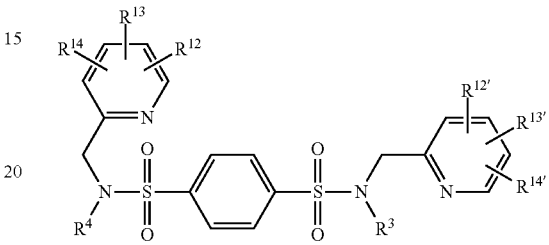
wherein
$R^3$ represents —$R^7$;
$R^4$ represents —$CH_2$—$R^8$, or —$CH_2$—$CH_2$—$R^8$;
$R^7$ represents
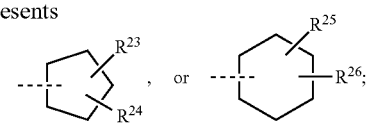
$R^8$ represents
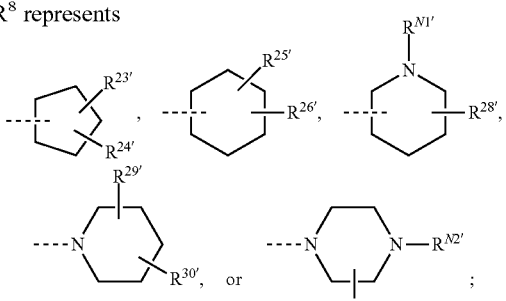
$R^9$-$R^{20}$, $R^{9'}$-$R^{20'}$, $R^{23}$-$R^{26}$, $R^{23'}$-$R^{30'}$ and $R^{N1'}$-$R^{2'}$ have the same meanings as defined above.
In one embodiment, the present invention is directed to the compound of the formula (IV)
(IV)
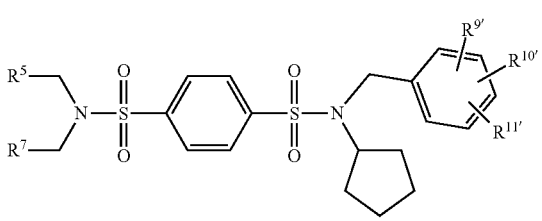
wherein
$R^5$ represents
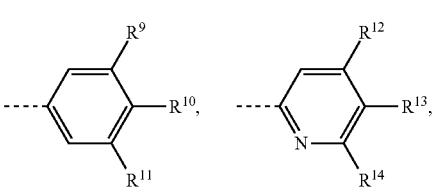

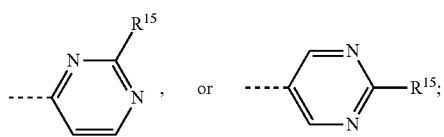

$R^7$ represents

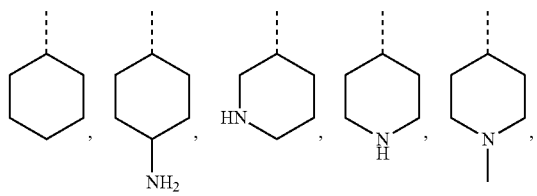

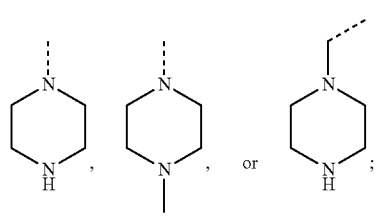

and $R^9$-$R^{15}$, and $R^{9'}$-$R^{11'}$ represent independently of each other:

—H, —F, —Cl, —Br, —CH$_3$, —CH$_2$F, —CHF$_2$, —CF$_3$, —CH$_2$Cl, —OCHF$_2$, —OCF$_3$, —COOH, —COOCH$_3$, —NH$_2$, —NHCH$_3$, —CONH$_2$, —CONHCH$_3$, —NHSO$_2$CH$_3$, —NHSO$_2$CF$_3$, —SO$_2$NH$_2$, —SO$_2$NHCH$_3$, or —NHSO$_2$CF$_3$.

More preferred, an embodiment of the present invention is directed to the compound of the formula (V)

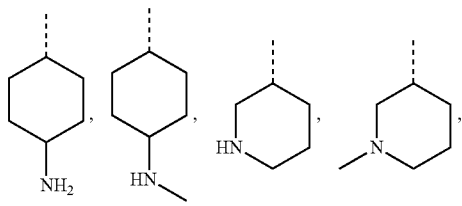

(V)

wherein
$R^4$ represents

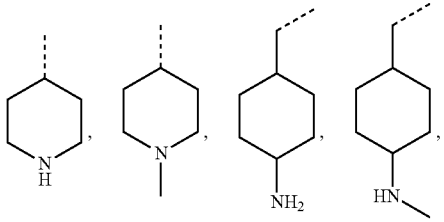

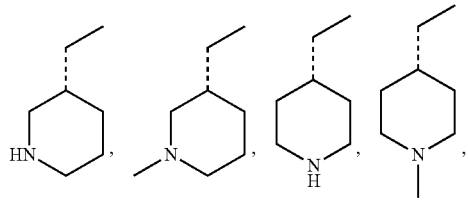

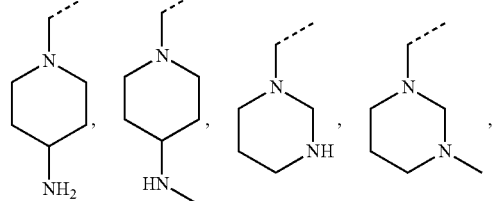

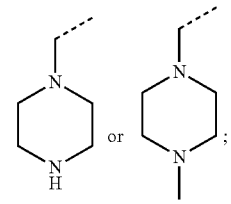

and $R^{15}$ represent —H, —F, —Cl, —Br, —CH$_3$, —CH$_2$F, —CHF$_2$, —CF$_3$, —CH$_2$Cl, —OCHF$_2$, —OCF$_3$, —COOH, —COOCH$_3$, —NH$_2$, —NHCH$_3$, —CONH$_2$, —CONHCH$_3$, —NHSO$_2$CH$_3$, —NHSO$_2$CF$_3$, —SO$_2$NH$_2$, —SO$_2$NHCH$_3$, or —NHSO$_2$CF$_3$.

Still more preferred is the compound of the formula (VI)

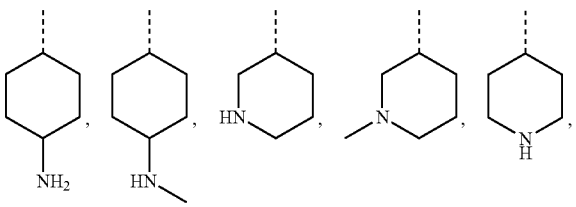

(VI)

wherein
$R^4$ presents

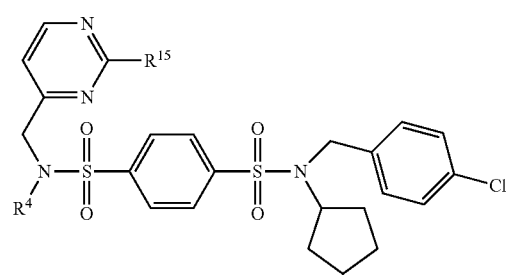

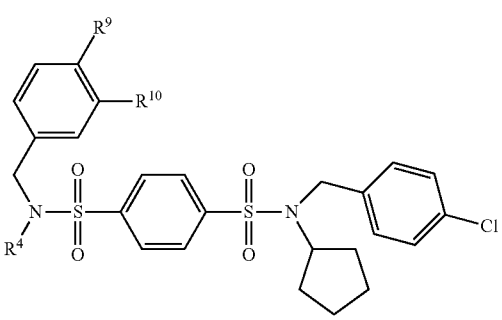

-continued

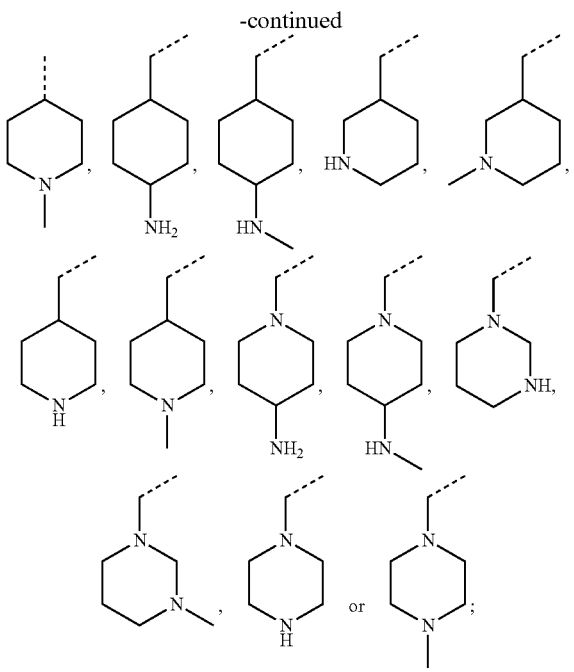

R⁹ represents —F, —Cl, —Br, —CH$_2$F, —CHF$_2$, —CF$_3$, —CH$_2$Cl, —OCHF$_2$, —OCF$_3$, —COOH, —COOCH$_3$; and R¹⁰ represents —NH$_2$, —NHCH$_3$, —N(CH$_3$)$_2$, —CONH$_2$, —CONHCH$_3$, —NHSO$_2$CH$_3$, —NHSO$_2$CF$_3$, —SO$_2$NH$_2$, —SO$_2$NHCH$_3$, or —NHSO$_2$CF$_3$.

Most preferred, the compound of the present invention is selected from the group consisting of:

Compound 02: N1-(5-amino-2-bromobenzyl)-N4-(4-chlorobenzyl)-N4-cyclopentyl-N1-(piperidin-4-ylmethyl)benzene-1,4-disulfonamide, Compound 04: tert-butyl 4-(((N-benzyl-4-(N-cyclopentyl-N-(3,5-dibromobenzyl)sulfamoyl)phenyl)sulfonamido)methyl)piperidine-1-carboxylate, Compound 05: N1-((5-bromo-2-(methylamino)pyrimidin-4-yl)methyl)-N4-(4-chlorobenzyl)-N1-(cyclohexylmethyl)-N4-cyclopentylbenzene-1,4-disulfonamide, Compound 06: N1-benzyl-N4-(4-chlorobenzyl)-N4-cyclopentyl-N1-((1-methylpiperidin-4-yl)methyl)benzene-1,4-disulfonamide, Compound 09: N1-benzyl-N4-(4-chlorobenzyl)-N1-(cyclohexylmethyl)-N4-cyclopentylbenzene-1,4-disulfonamide, Compound 10: N1-benzyl-N4-(4-chlorobenzyl)-N4-cyclopentyl-N1-(2-(piperazin-1-yl)ethyl)benzene-1,4-disulfonamide, Compound 11: N1-(4-chlorobenzyl)-N1-cyclopentyl-N4-(piperidin-4-ylmethyl)-N4-(pyrazin-2-ylmethyl)benzene-1,4-disulfonamide, Compound 12: N1-benzyl-N4-((5-chloropyrazin-2-yl)methyl)-N4-cyclopentyl-N1-(piperidin-4-ylmethyl)benzene-1,4-disulfonamide, Compound 16: N1-(4-chlorobenzyl)-N1-cyclopentyl-N4-((2-(methylamino)pyrimidin-4-yl)methyl)-N4-(piperidin-4-ylmethyl)benzene-1,4-disulfonamide, Compound 17: N1-benzyl-N4-(3-bromobenzyl)-N4-cyclopentyl-N1-(piperidin-4-ylmethyl)benzene-1,4-disulfonamide, Compound 18: N1,N4-dibenzyl-N1,N4-bis(piperidin-4-ylmethyl)benzene-1,4-disulfonamide, Compound 19: N1-(4-aminocyclohexyl)-N4-(4-chlorobenzyl)-N4-cyclopentyl-N1-((2-(methylamino)pyrimidin-4-yl)methyl)benzene-1,4-disulfonamide, Compound 20: N1-(4-chlorobenzyl)-N4-(cyclohexylmethyl)-N1-cyclopentyl-N4-((2-(methylamino)pyrimidin-4-yl)methyl)benzene-1,4-disulfonamide, Compound 21: 4-(((4-(N-(4-chlorobenzyl)-N-cyclopentylsulfamoyl)-N-(piperidin-4-ylmethyl)phenyl)sulfonamido)methyl)-2-(methylamino)benzoic acid, Compound 22: 2-amino-4-(((4-(N-(4-chlorobenzyl)-N-cyclopentylsulfamoyl)-N-(piperidin-4-ylmethyl)phenyl)sulfonamido)methyl)benzoic acid, Compound 23: methyl 2-amino-4-(((4-(N-(4-chlorobenzyl)-N-cyclopentylsulfamoyl)-N-(piperidin-4-ylmethyl)phenyl)sulfonamido)methyl)benzoate, Compound 24: N1-benzyl-N4-(3-bromo-5-(tert-butyl)benzyl)-N4-cyclopentyl-N1-(piperidin-4-ylmethyl)benzene-1,4-disulfonamide, Compound 25: N1-benzyl-N4-(3-bromo-5-(trifluoromethyl)benzyl)-N4-cyclopentyl-N1-(piperidin-4-ylmethyl)benzene-1,4-disulfonamide, Compound 26: N1-benzyl-N4-(4-chlorobenzyl)-N4-cyclopentyl-N1-(piperidin-3-ylmethyl)benzene-1,4-disulfonamide, Compound 27: N1-(4-chlorobenzyl)-N1-cyclopentyl-N4-(piperidin-4-ylmethyl)-N4-(pyrimidin-5-ylmethyl)benzene-1,4-disulfonamide, Compound 34: N1-(2-bromobenzyl)-N4-(4-chlorobenzyl)-N1-(cyclohexylmethyl)-N4-cyclopentylbenzene-1,4-disulfonamide, Compound 35: N1-(3-bromobenzyl)-N4-(4-chlorobenzyl)-N1-(cyclohexylmethyl)-N4-cyclopentylbenzene-1,4-disulfonamide, Compound 36: N1-(2-bromophenyl)-N4-(4-chlorobenzyl)-N1-(cyclohexylmethyl)-N4-cyclopentylbenzene-1,4-disulfonamide, Compound 37: N1-(2-bromo-5-(trifluoromethyl)phenyl)-N4-(4-chlorobenzyl)-N1-(cyclohexylmethyl)-N4-cyclopentylbenzene-1,4-disulfonamide, Compound 40: ethyl 2-(((4-(N-(4-chlorobenzyl)-N-cyclopentylsulfamoyl)-N-((tetrahydro-2H-pyran-4-yl)methyl)phenyl)sulfonamido)methyl)benzoate, and Compound 44: N1-benzyl-N4-(4-chlorobenzyl)-N4-cyclopentyl-N1-(piperidin-4-ylmethyl)benzene-1,4-disulfonamide.

Chemical Synthesis

Scheme 1: Retrosynthesis of disulfonamides of general formula (I).

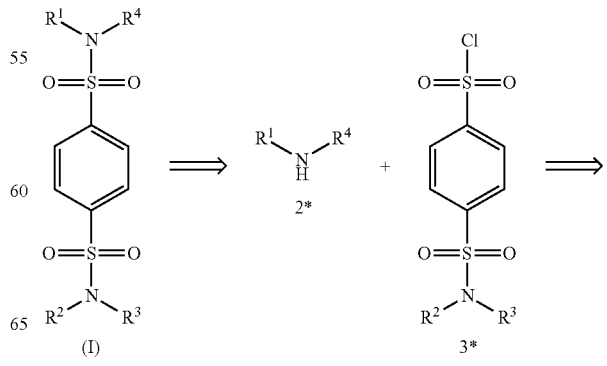

Compounds 2* and 7* can be either primary or secondary amines. Secondary amines 2* and 7* can be prepared by standard reductive amination procedures (see Scheme 3).

Scheme 3: Synthesis of amines by reductive amination

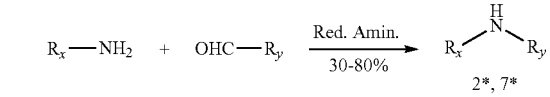

Some of the compounds of the present invention may be crystallized or recrystallized from solvents such as aqueous and organic solvents. In such cases solvates may be formed. This invention includes within its scope stoichiometric solvates including hydrates as well as compounds containing variable amounts of water that may be produced by processes such as lyophilization.

The compounds of the general formulae (I), (II), (III-1)-(III-8), (IV), (V) and (VI) may exist in the form of optical isomers, i.e. enantiomers and mixtures of said isomers in all ratios, e.g. racemic mixtures. The invention includes all such forms, in particular the pure isomeric forms or enantiomeric forms. The different isomeric forms may be separated or resolved one from the other by conventional methods, or any given isomer may be obtained by conventional synthetic methods or by stereospecific or asymmetric syntheses.

The compounds of the general formulae (I), (II), (III-1)-(III-8), (IV), (V) and (VI) may form salts with organic or inorganic acids. Examples of suitable acids for such acid addition salt formation are trifluoroacetic acid, hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

The inventive disulfonamides of general formula (I) can be prepared by methods known to one skilled in the art.

The syntheses of disulfonamides (I) commence with the treatment of commercially available 4-bromobenzenesulfonyl chloride (6*) with the amine 7*, in the presence of $Et_3N$ using DCM as solvent. A $Pd_2(dba)_3$/Xantphos catalytic system was used for the C—S cross-coupling of the phenyl bromide with benzyl thiol to provide compound 4*. Transformation of this compound into sulfonyl chloride 3* was achieved by using 2,4-dichloro-5,5-dimethylhydantoin in a mixture of acetonitrile, acetic acid and water as solvent. Finally, reaction of 3* with the correspondent amine 2* in the presence of a base allowed us to obtain disulfonamides (I) (see Scheme 2).

Scheme 2: Synthesis of disulfonamides of general formula (I).

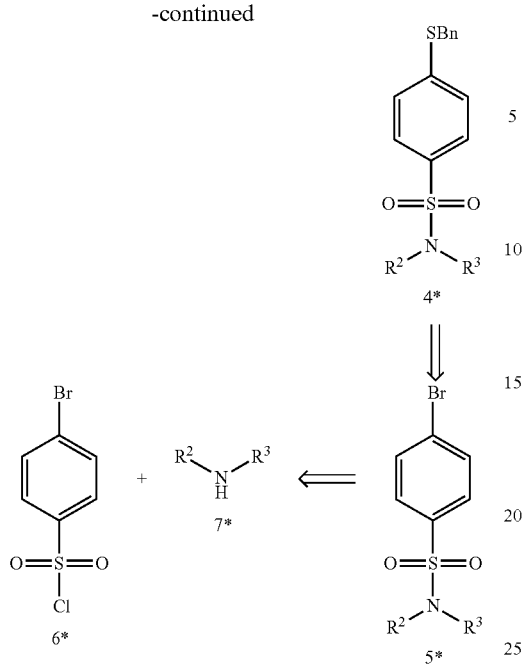

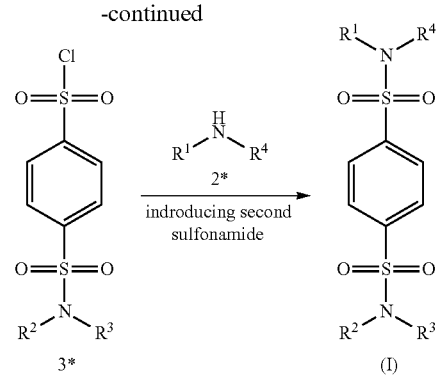

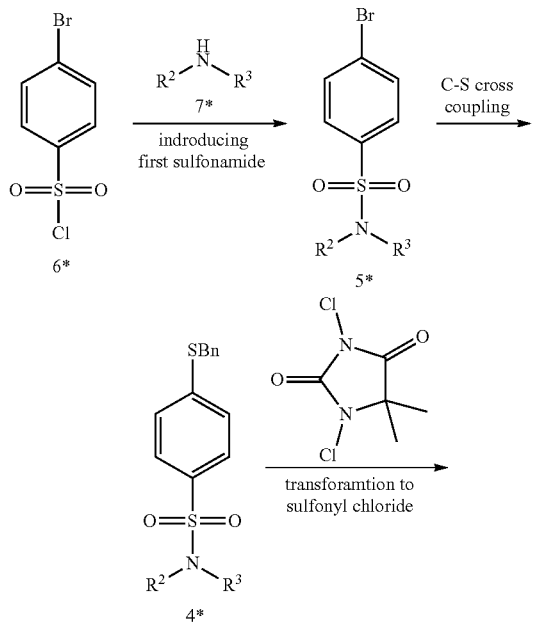

Biological Activity

According to the crystal structures of some inventive compounds as shown in FIG. 3, it was found that the inventive compound of general formula (I) are able to bind deeply in the PDE6δ binding pocket by establishing at least three H-bonds between two sulfonamide moieties of the inventive compound to Arg71, Gln78 and Tyr149 of PDE6δ and π-π interaction between backbone benzene ring and Trp90 of PDE66. Additionally, the substituents $R^5$-$R^8$ of the inventive compound of the formula (I) can form further H-bonds with Cys56, Glu88, Met118 and Gln116 and $R^3$ can have an interaction with Trp32. For example, 10 non-covalent interactions stabilize the binding of compound 16 (Deltasonamide 1) inside the PDE6δ binding pocket, including H-bonds to Arg71, Gln78, Glu88 and Tyr149 side-chains, to the carbonyl of Cys56, two water molecule-mediated H-bonds to the Glu88 side-chain and the amide proton of Met118, two aromatic-π interactions to the indole side-chains of Trp32 and Trp80, and one Met117-aryl interaction. This enhanced the in vitro potency. It was proven by affinity assay that the inventive benzene disulfonamides compound of the formula (I) have very high affinity to PDE6δ as summarized in Table 3 of Example D2.

Arl2-mediated displacement assay with the inventive compounds demonstrated that increase of the number of interactions between the inventive compound and PDE6 δ lead to a higher stabilization of the complex and higher resistance to displacement by Arl2 compared to the known PDE6δ inhibitors as described in Example D.3 and shown in FIG. 2.

In contrast to the Deltarasin and Deltazinone 1, fluorescently labeled compound 8L* (FIG. 1) could not be directly displaced from PDE6δ by 5 and even 25 eq. of Arl2 (FIG. 2B). Acceleration of release by 2.5 eq. of Arl 2 in the presence of 200-fold excess of non-fluorescent inhibitor was 45- and 25-fold slower than the release of 1L* and 2L*, respectively (FIG. 2C vs. 2D). Thus increase of the number of inhibitor-PDE6δ interactions leads to a higher stabilization of the complex and higher resistance to displacement by Arl2.

PDE6δ engagement by inhibitor 22 was proven by means of a cellular thermal shift assay (CETSA) in which the thermal stabilization of the protein of interest upon ligand binding is determined. Mass spectrometric analysis of Jurkat cell lysate treated with 1 μM compound 22 identified proteins showing a characteristic shift in melting temperature by at least 2° C., or for which the differences in the signal intensities for at least two characteristic peptides were at least 10% (FIG. 2E, F) ligand 22 only engaged PDE6δ and ribosomal protein L31 (RPL31). Thus compound 22 is a very selective inhibitor of PDE66.

Disruption of the interaction between mCherry-PDE6δ and farnesylated Ras proteins (mCitrine-RheB) in living cells was measured in MDCK cells by FLIM-FRET. The homogenous fluorescence patterns of both proteins in the absence of inhibitor indicate solubilization of mCitrine-RheB by mCherry-PDE6δ (FIG. 4A,B), which was also reflected in the high molar fraction α of interacting mCitrine-RheB and mCherry-PDE6δ as derived from global analysis of FLIM data. Treatment with increasing concentrations of compounds 16 and 19 (Deltasonamides 1 and 2) resulted in a reduced interacting fraction α of RheB-PDE66. Fitting the does-dependent measurements to an equilibrium model with a clamped compound concentration yielded an apparent "in-cell" $K_D$ of 85±18 nM for compound 16 (Deltasonamide 1) and 61±5 nM for compound 19 (Deltasonamide 2). In contrast to Deltarasin, these apparent $K_D$'s surpass the in vitro measured $K_D$'s by an order of magnitude. If the partitioning coefficient P of the compounds between cytoplasm and extracellular environment is independent of administered compound concentration, the ratio of the in vivo and in vitro $K_D$'s reflects P. This indicates that only ~02-0.6% of the extracellular Deltasonamide concentration is available in the cytoplasm to inhibit PDE66.

The inhibitors of the present invention also led to a loss of KRas plasma membrane (PM) localization as apparent from MiaPaCa-2 cells ectopically expressing mCitrine-KRas were treated with 5 μM compound 19 (Deltasonamide 2, FIG. 4C). Analysis of variance showed significance for loss of plasma membrane localization between 0 min and 30 min onwards in agreement with the effective rate of KRas PM dissociation.

It was also proven by proliferation assay of various cancer cell lines that the inventive compounds inhibit effectively proliferation of cancer cells, especially pancreatic cancer cells as demonstrated in Example D.4 and FIG. 5.

Analysis of anti-proliferative activity by means of impedance-based real time cell analyzer (RTCA) measurements revealed that treatment of the oncogenic KRas-dependent Panc-Tu-I, and MiaPaCa-2 cells with either compound 16 (Deltasonamide 1) or compound 19 (Deltasonamide 2) resulted in a strongly reduced proliferation, even at submicromolar concentrations (FIG. 5). This was most pronounced in MiaPaCa-2 cells treated with compound 19 (Deltasonamide 2) with about 50% reduction of growth rate at 750 nM (FIG. 5B). Growth of Panc Tu-I cells was reduced by ca. 50% at 1.5 μM. Thus the compounds are ca. 30-fold more potent than the known Deltazinone 1.

Analysis of anti-proliferative activity by means of impedance-based real time cell analyzer (RTCA) measurements revealed that treatment of the colorectal cancer cell lines, DiFi, HCT-116, Hke3, Hkh2, HT29 and SW480 with either compound 16 (Deltasonamide 1) or compound 19 (Deltasonamide 2) resulted in a strongly reduced proliferation, even at lower micromolar concentrations (FIG. 6).

Further, compound 19 (Deltasonamide 2) showed growth inhibitory effect and reduced cell viability at lower micromolar concentrations (1.5-3 μM) in colorectal cancer cell lines containing oncogenic KRas mutations (HCT-116, Hke3, and SW480) but also showed unspecific toxicity at concentration above 6 μM in all tested cell lines (Hkh2, DiFi, HT29) (FIGS. 7A and B).

These results confirm that PDE delta is not only essential for pancreatic ductal adenocarcinoma cancer cell lines depending on oncogenic KRas but also for colorectal cancer cell lines harboring an oncogenic KRas mutation, pointing to a general role of PDEδ in KRas-driven tumors. Therefore, the inventive compound as PDEδ inhibitor can be generally used for treatment or prophylaxis of KRas-driven cancer, tumors and proliferative diseases, It was also found by permeability assay with Caco-2 cell that the inventive compounds show the enhanced permeability as described in Example D.5. Further, cytotoxicity assay with human peripheral blood mononuclear cells (hPMPBC) revealed that the inventive compounds such as compounds 16 and 19, do not impair hPMBCs proliferation up to 30 μM concentration in contrast to the known inhibitor Deltarasin.

Indications and Pharmaceutical Compositions

Therefore, another aspect of the present invention relates to the use of the inventive substituted benzene sulfonamide of the formula (I) as drugs, i.e. as pharmaceutically active agents applicable in medicine.

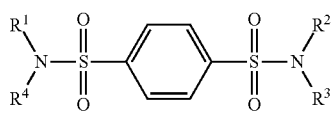

(I)

wherein $R^1$ represents —$CH_2$—$R^5$, or —$CH_2$—$CH_2$—$R^5$;

$R^2$ represents —H, —$R^A$, —$CH_2$—$R^6$;

$R^3$ represents —$R^B$, —$R^7$, —$CH_2$—$R^7$, or —$CH_2$—$CH_2$—$R^7$; or

—$NR^2R^3$ represents

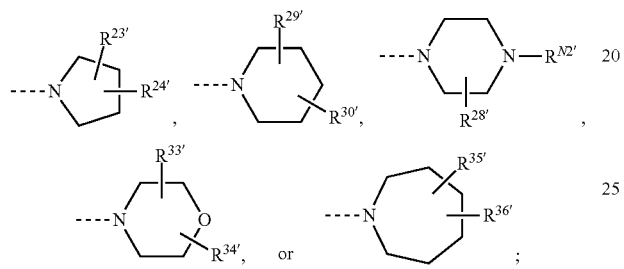

$R^4$ represents —$R^C$, —$R^8$, —$CH_2$—$R^8$, or —$CH_2$—$CH_2$—$R^8$; or $R^1$ and $R^4$ form together

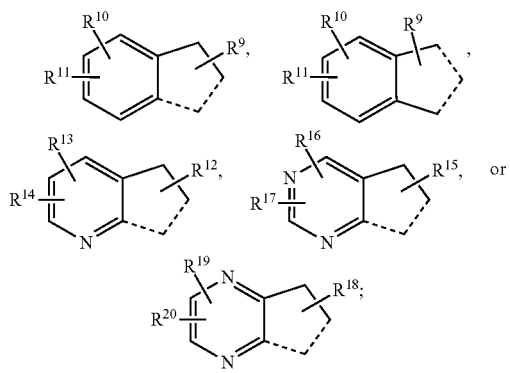

wherein $R^2$, $R^3$ and $R^4$ are not $R^A$, $R^B$, $R^C$ at the same time;

$R^5$ represents

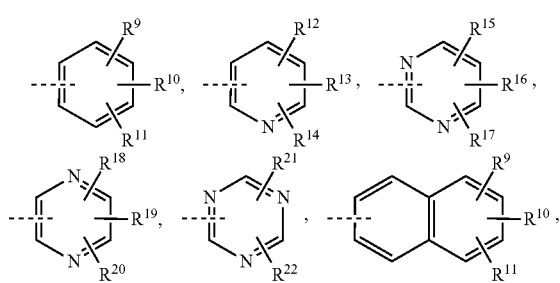

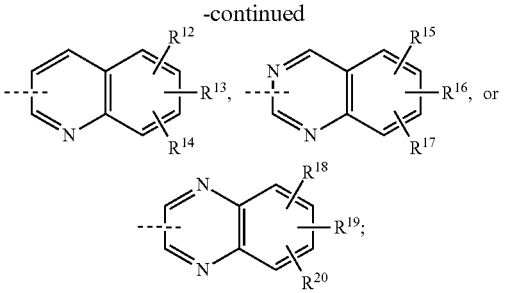

$R^6$ represent

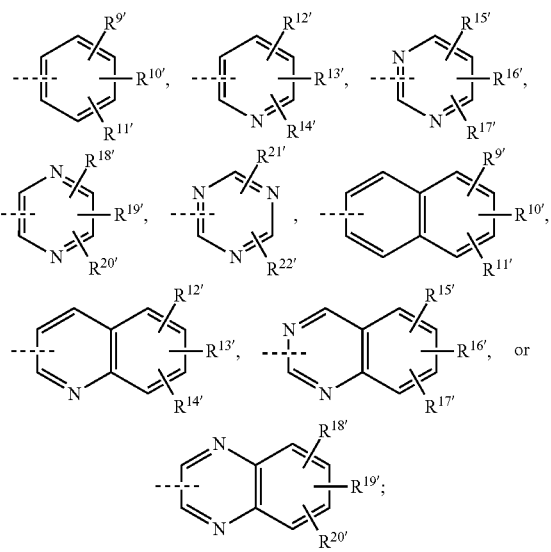

$R^7$ represents

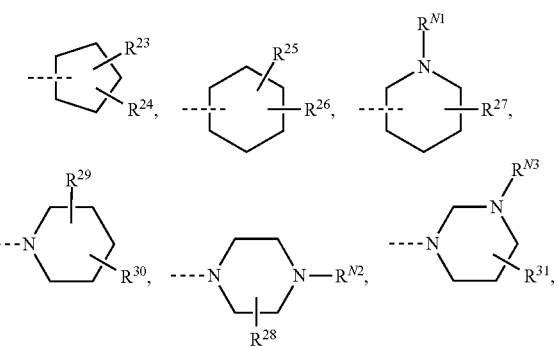

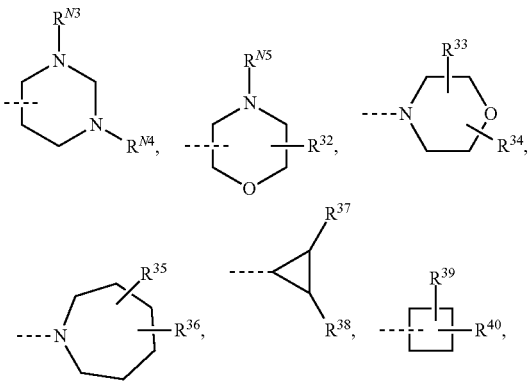

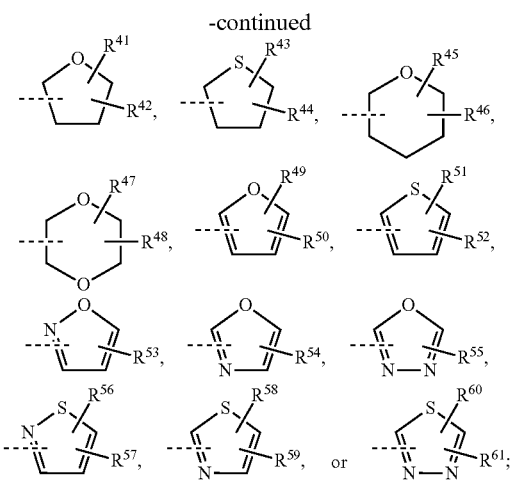

R⁸-represents

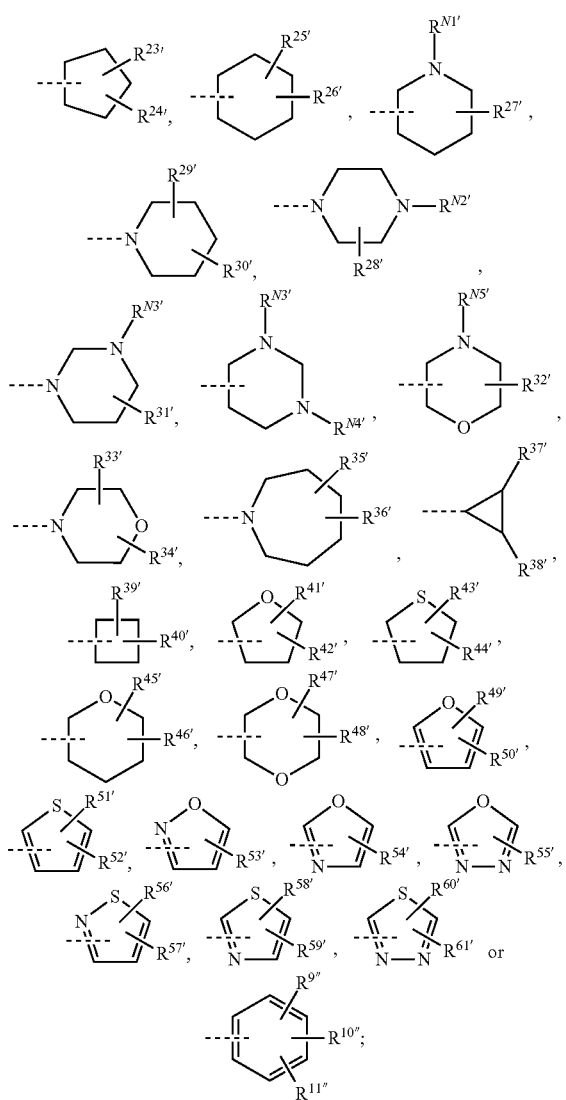

$R^A$, $R^B$, and $R^C$ represent independently of each other
—CH₃, —C₂H₅, —C₃H₇, —CH(CH₃)₂, —C₄H₉, —CH(CH₃)—CH₂CH₃, —CH₂—CH(CH₃)₂, —C(CH₃)₃, —C₅H₁₁, —C₆H₁₃, —CH(CH₃)—CH₂CH₂CH₃, —CH₂—CH(CH₃)CH₂CH₃, —CH₂—CH₂CH(CH₃)₂, —CH(CH₃)—CH(CH₃)₂, —CH₂—C(CH₃)₃, —CH₂CH₂CH₂CH(CH₃)₂, —CH₂OH, —C₂H₄OH, —C₃H₆OH, —C₄H₈OH, —C₅H₁₀OH, —C₆H₁₂OH, —CH(OH)—CH₂OH, —CH₂—CH(OH)—CH₂OH, —CH(CH₂OH)₂, —CH₂—CH(CH₂OH)₂, —CH₂OSi(CH₃)₃, —C₂H₄OSi(CH₃)₃, —C₃H₆OSi(CH₃)₃, —C₄H₈OSi(CH₃)₃, —C₅H₁₀OSi(CH₃)₃, —C₆H₁₂OSi(CH₃)₃, —CH₂OSi(C₂H₅)₃, —C₂H₄OSi(C₂H₅)₃, —C₃H₆OSi(C₂H₅)₃, —C₄H₈OSi(C₂H₅)₃, —C₅H₁₀OSi(C₂H₅)₃, —C₆H₁₂OSi(C₂H₅)₃, —CH₂OSi[CH(CH₃)₂]₃, —C₂H₄OSi[CH(CH₃)₂]₃, —C₃H₆OSi[CH(CH₃)₂]₃, —C₄H₈OSi[CH(CH₃)₂]₃, —C₅H₁₀OSi[CH(CH₃)₂]₃, —C₆H₁₂OSi[CH(CH₃)₂]₃, —CH₂OSi(CH₃)₂C(CH₃)₃, —C₂H₄OSi(CH₃)₂C(CH₃)₃, —C₃H₆OSi(CH₃)₂C(CH₃)₃, —C₄H₈OSi(CH₃)₂C(CH₃)₃, —C₅H₁₀OSi(CH₃)₂C(CH₃)₃, or —C₆H₁₂OSi(CH₃)₂C(CH₃)₃;

$R^9$-$R^{22}$, $R^{9'}$—$R^{22'}$ and $R^{9''}$-$R^{11''}$ represent independently of each other —H, —F, —Cl, —Br, —I, —OH, —CN, —NO₂, —CH₃, —C₂H₅, —C₃H₇, —CH(CH₃)₂, —C₄H₉, —CH₂—CH(CH₃)₂, —CH(CH₃)—C₂H₅, —C(CH₃)₃, -cyclo-C₃H₅, —CH₂-cyclo-C₃H₅, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, —OCH₃, —OC₂H₅, —OC₃H₇, —OCH(CH₃)₂, —OC(CH₃)₃, —OC₄H₉, —OCHF₂, —OCF₃, —OCH₂CF₃, —OC₂F₅, —OCH₂OCH₃, —O-cyclo-C₃H₅, —OCH₂-cyclo-C₃H₅, —O—C₂H₄-cyclo-C₃H₅, —CHO, —COCH₃, —COCF₃, —COC₂H₅, —COC₃H₇, —COCH(CH₃)₂, —COC(CH₃)₃, —COOH, —COOCH₃, —COOC₂H₅, —COOC₃H₇, —COOCH(CH₃)₂, —COOC(CH₃)₃, —OOC—CH₃, —OOC—CF₃, —OOC—C₂H₅, —OOC—C₃H₇, —OOC—CH(CH₃)₂, —OOC—C(CH₃)₃, —NH₂, —NHCH₃, —NHC₂H₅, —NHC₃H₇, —NHCH(CH₃)₂, —NHC(CH₃)₃, —N(CH₃)₂, —N(C₂H₅)₂, —N(C₃H₇)₂, —N[CH(CH₃)₂]₂, —N[C(CH₃)₃]₂, —CH₂NH₂, —CH₂NHCH₃, —CH₂NHC₂H₅, —CH₂N(CH₃)₂, —CH₂N(C₂H₅)₂, —NHCOCH₃, —NHCOCF₃, —NHCOC₂H₅, —NHCOC₃H₇, —NHCOCH(CH₃)₂, —NHCOC(CH₃)₃, —CONH₂, —CONHCH₃, —CONHC₂H₅, —CONHC₃H₇, —CONHCH(CH₃)₂, —CONH-cyclo-C₃H₅, —CONHC(CH₃)₃, —CON(CH₃)₂, —CON(C₂H₅)₂, —CON(C₃H₇)₂, —CON[CH(CH₃)₂]₂, —CON[C(CH₃)₃]₂, —SO₂NH₂, —SO₂NHCH₃, —SO₂NHC₂H₅, —SO₂NHC₃H₇, —SO₂NHCH(CH₃)₂, —SO₂NH-cyclo-C₃H₅, —SO₂NHC(CH₃)₃, —SO₂N(CH₃)₂, —SO₂N(C₂H₅)₂, —SO₂N(C₃H₇)₂, —SO₂N[CH(CH₃)₂]₂, —SO₂N[C(CH₃)₃]₂, —NHSO₂CH₃, —NHSO₂CF₃, —NHSO₂C₂H₅, —NHSO₂C₃H₇, —NHSO₂CH(CH₃)₂, —NHSO₂C(CH₃)₃, —CH═CH₂, —CH₂—CH═CH₂, —C(CH₃)═CH₂, —CH═CH—CH₃, —C≡CH, —C≡C—CH₃, —CH₂—C≡CH, -Ph, —O-Ph, —O—CH₂-Ph, —OSi(CH₃)₃, —OSi(C₂H₅)₃, —OSi(CH₃)₂C(CH₃)₃,

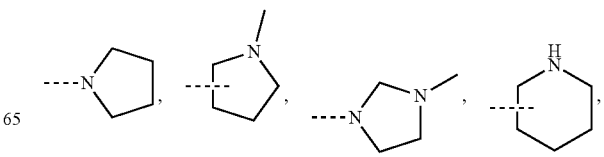

-continued

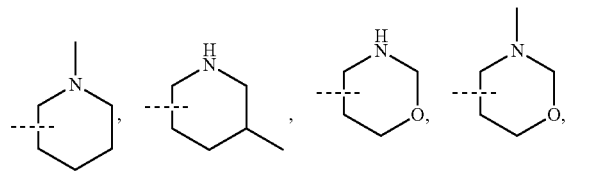

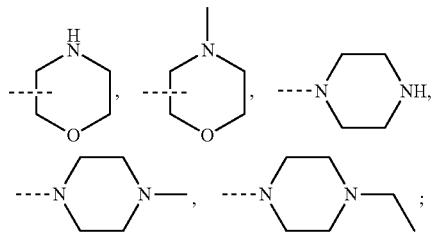

or $R^{10}$-$R^{11}$ and $R^{10'}$-$R^{11'}$ can form together any one of the following five or six rings;

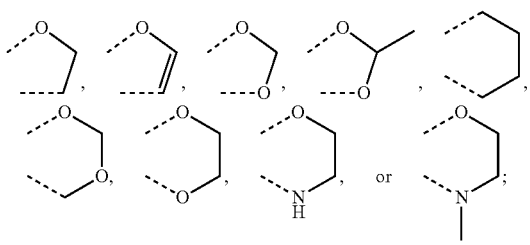

$R^{23}$-$R^{61}$ and $R^{23'}$-$R^{61'}$ represent independently of each other

—H, —F, —Cl, —OH, —CN, —NO$_2$, —CH$_3$, —C$_2$H$_5$, —C$_3$H$_7$, —CH(CH$_3$)$_2$, —CF$_3$, —OCH$_3$, —OC$_2$H$_5$, —OC$_3$H$_7$, —OCH(CH$_3$)$_2$, —OCF$_3$, —OCH$_2$OCH$_3$, —O-cyclo-C$_3$H$_5$, —OCH$_2$-cyclo-C$_3$H$_5$, —COOCH$_3$, —COOC$_2$H$_5$, —OOC—CH$_3$, —OOC—CF$_3$, —OOC—C$_2$H$_5$, —OOC—C(CH$_3$)$_3$, —NH$_2$, —NHCH$_3$, —NHC$_2$H$_5$, —NHCH(CH$_3$)$_2$, —N(CH$_3$)$_2$, —N(C$_2$H$_5$)$_2$, —CH$_2$NH$_2$, —CH$_2$NHCH$_3$, —CH$_2$NHC$_2$H$_5$, —CH$_2$N(CH$_3$)$_2$, —CH$_2$N(C$_2$H$_5$)$_2$, —NHCOCH$_3$, —NHCOCF$_3$, —CONH$_2$, —CONHCH$_3$, —CONHC$_2$H$_5$, —CON(CH$_3$)$_2$, —CON(C$_2$H$_5$)$_2$, —SO$_2$NH$_2$, —SO$_2$NHCH$_3$, —SO$_2$NHC$_2$H$_5$, —SO$_2$N(CH$_3$)$_2$, —SO$_2$N(C$_2$H$_5$)$_2$, —NHSO$_2$CH$_3$, —NHSO$_2$CF$_3$, or —NHSO$_2$C$_2$H$_5$;

$R^{N1}$-$R^{N5}$, and $R^{N1'}$-$R^{N5'}$ represent independently of each other —H, —CH$_3$, —C$_2$H$_5$, —C$_3$H$_7$, —CH(CH$_3$)$_2$, -cyclo-C$_3$H$_5$, —COCH$_3$, —COCF$_3$, —COC(CH$_3$)$_3$, —OOC—CH$_3$, —OOC—CF$_3$, —OOC—C$_2$H$_5$, —OOC—C(CH$_3$)$_3$, —SO$_2$CH$_3$, or —SO$_2$CF$_3$;

or pharmaceutically acceptable salts thereof.

Preferably, $R^5$ represents the following groups:

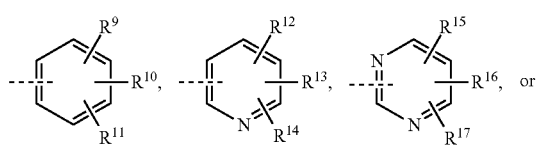

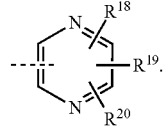

More preferably, $R^5$ represents the following groups:

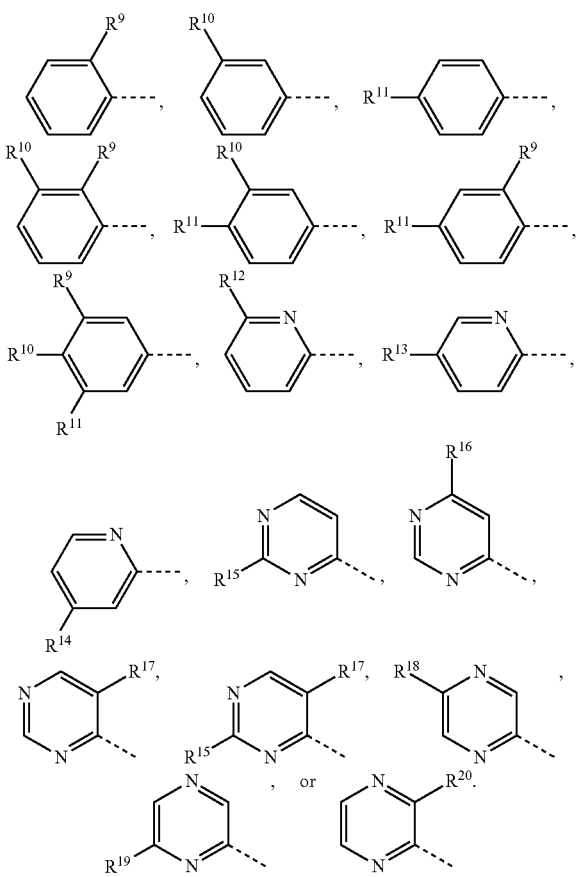

Most preferably $R^5$ represents the following groups:

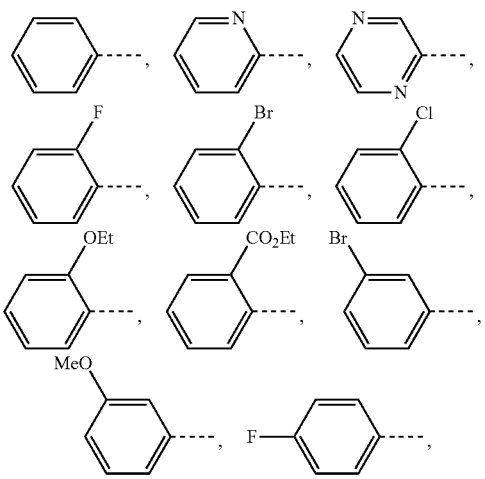

-continued
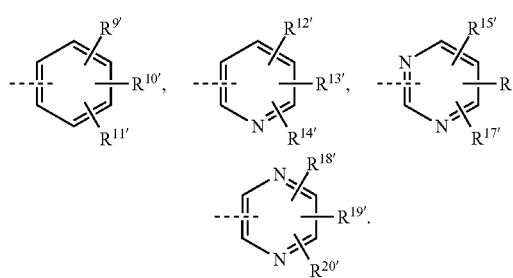
Preferably, $R^6$ represents the following groups:
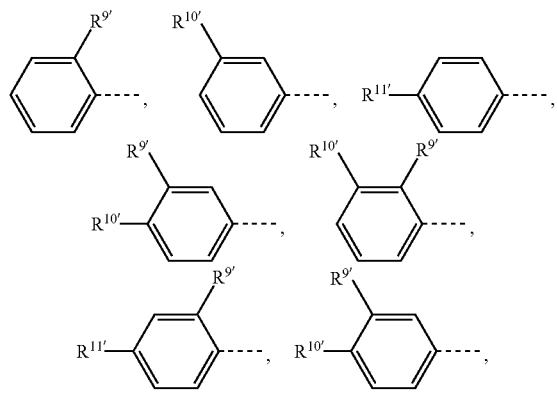
More preferably, $R^6$ represents the following groups:
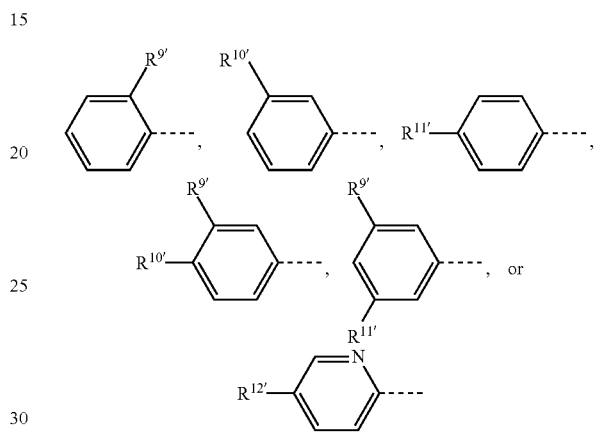
Still more preferably, $R^6$ represents the following groups:
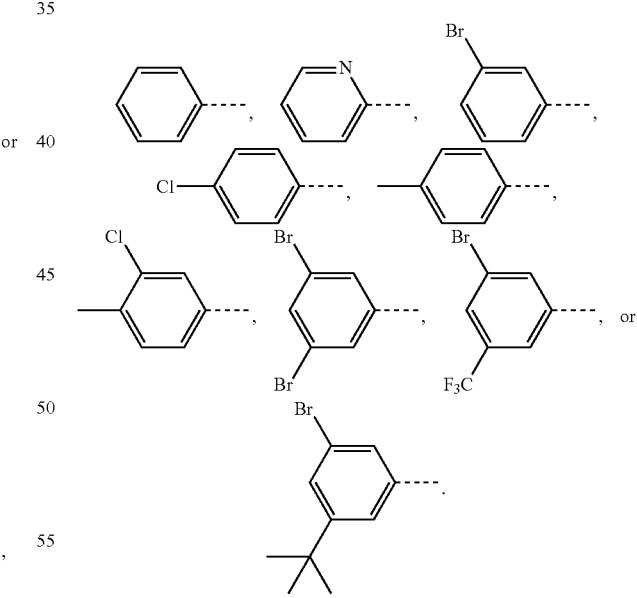
Most preferably, $R^6$ represents the following groups:
Preferably, $R^1$ and $R^4$ form together
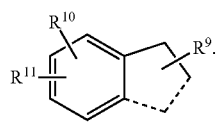

Preferably, $R^7$ represents
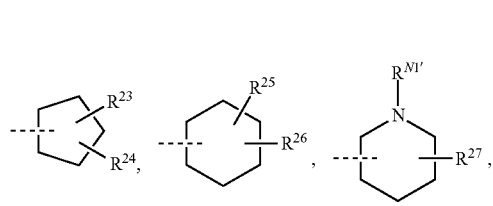
More preferably, $R^7$ represents
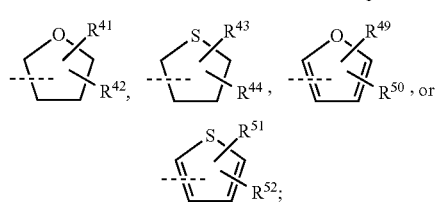
Most preferably, $R^7$ represents
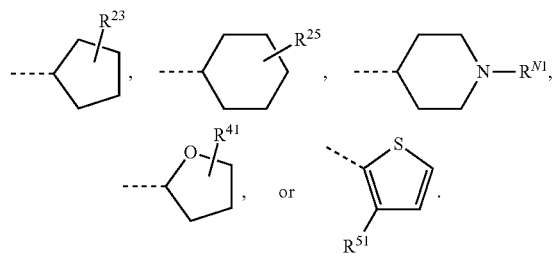
Preferably, $R^8$ represents
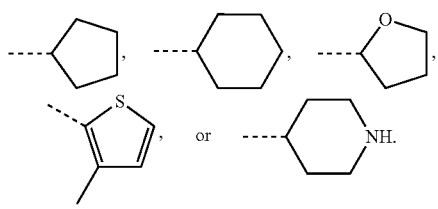
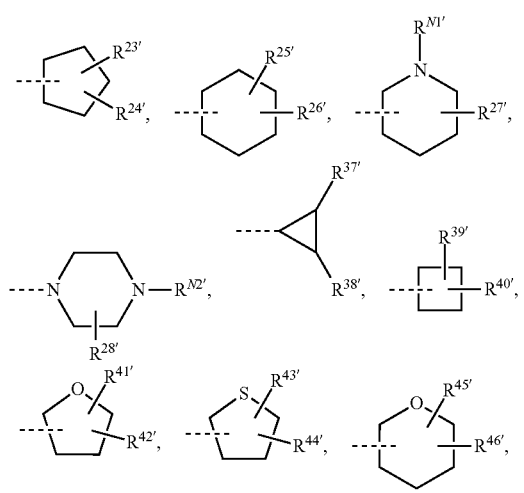
-continued
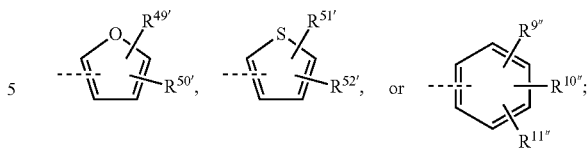
More preferably,
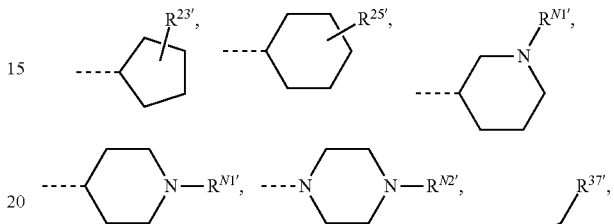
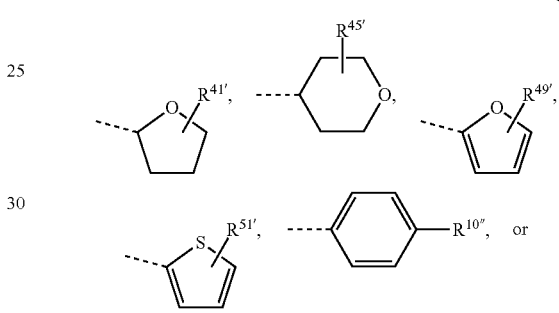
Still more preferably,
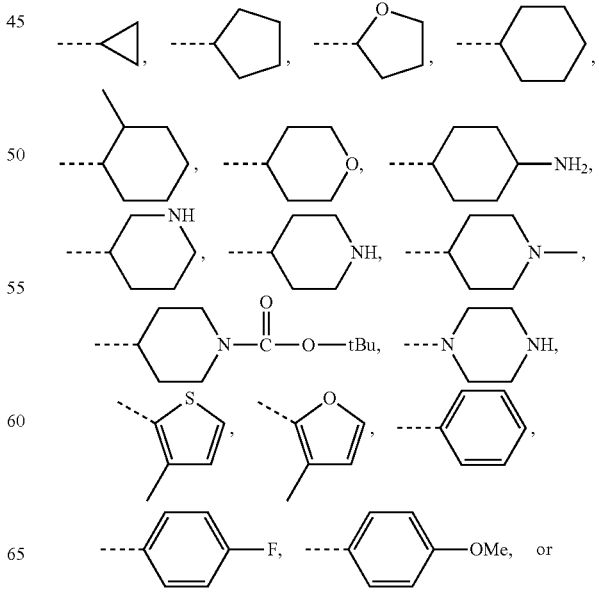

-continued

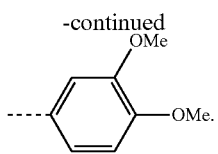

Preferably, $R^C$ represent

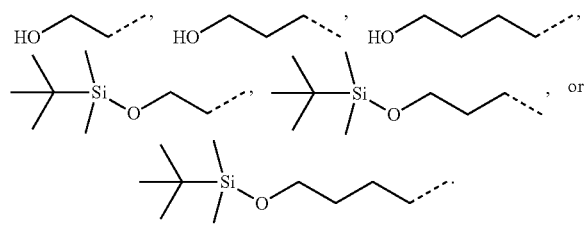

Preferably $R^9$-$R^{22}$, $R^{9'}$-$R^{22'}$ and $R^{9'''}$-$R^{11'''}$ represent independently of each other —H, —F, —Cl, —Br, —OH, —CH$_3$, —C$_2$H$_5$, —C$_3$H$_7$, —CH(CH$_3$)$_2$, —C(CH$_3$)$_3$, —CF$_3$, —OCH$_3$, —OC$_2$H$_5$, —OC$_3$H$_7$, —OCH(CH$_3$)$_2$, —OCHF$_2$, —OCF$_3$, —COOH, —COOCH$_3$, —COOC$_2$H$_5$, —NH$_2$, —NHCH$_3$, —NHC$_2$H$_5$, —N(CH$_3$)$_2$, —N(C$_2$H$_5$)$_2$, or —OSi(CH$_3$)$_2$C(CH$_3$)$_3$.

In an embodiment the present invention refers to a compound of the formula (I):

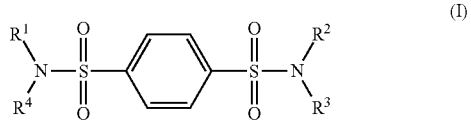

wherein
$R^1$ represents —CH$_2$—$R^5$;
$R^2$ represents —CH$_2$—$R^6$;
$R^3$ represents —$R^7$, —CH$_2$—$R^7$, or —CH$_2$—CH$_2$—$R^7$,
$R^4$ represents —$R^8$, —CH$_2$—$R^8$, or —CH$_2$—CH$_2$—$R^8$;
$R^5$ represents

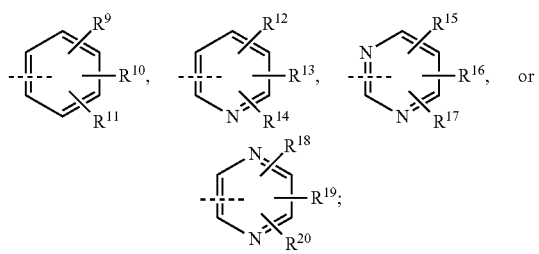

$R^6$ represents

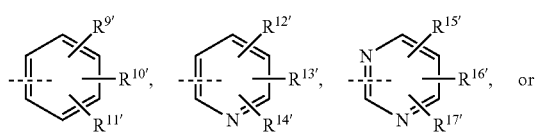

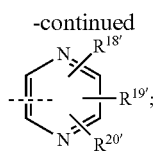

$R^7$ represents

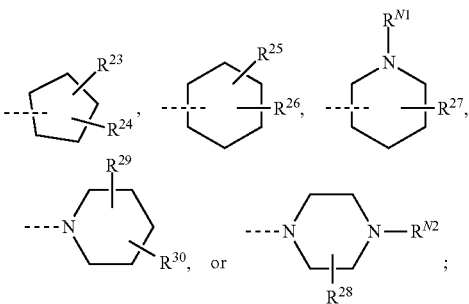

$R^8$ represents

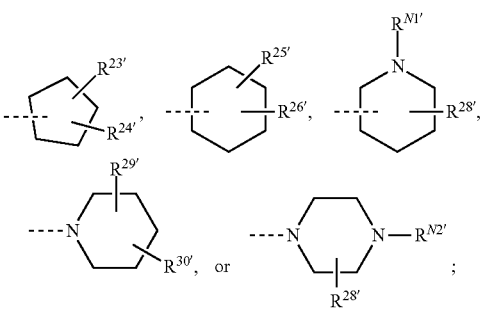

$R^9$-$R^{20}$ and $R^{9'}$-$R^{20'}$ represent independently of each other
—H, —F, —Cl, —Br, —I, —OH, —CN, —NO$_2$, —CH$_3$, —C$_2$H$_5$, —C$_3$H$_7$, —CH(CH$_3$)$_2$, —C$_4$H$_9$, —CH$_2$—CH (CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —OCH$_3$, —OC$_2$H$_5$, —OC$_3$H$_7$, —OCH(CH$_3$)$_2$, —OC(CH$_3$)$_3$, —OC$_4$H$_9$, —OCHF$_2$, —OCF$_3$, —OCH$_2$CF$_3$, —OC$_2$F$_5$, —OCH$_2$OCH$_3$, —O-cyclo-C$_3$H$_5$, —OCH$_2$-cyclo-C$_3$H$_5$, —O—C$_2$H$_4$-cyclo-C$_3$H$_5$, —CHO, —COCH$_3$, —COCF$_3$, —COC$_2$H$_5$, —COC$_3$H$_7$, —COCH(CH$_3$)$_2$, —COC(CH$_3$)$_3$, —COOH, —COOCH$_3$, —COOC$_2$H$_5$, —COOC$_3$H$_7$, —COOCH(CH$_3$)$_2$, —COOC(CH$_3$)$_3$, —OOC—CH$_3$, —OOC—CF$_3$, —OOC—C$_2$H$_5$, —OOC—C$_3$H$_7$, —OOC—CH(CH$_3$)$_2$, —OOC—C(CH$_3$)$_3$, —NH$_2$, —NHCH$_3$, —NHC$_2$H$_5$, —NHC$_3$H$_7$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N[CH(CH$_3$)$_2$]$_2$, —N[C(CH$_3$)$_3$]$_2$, —CH$_2$NH$_2$, —CH$_2$NHCH$_3$, —CH$_2$NHC$_2$H$_5$, —CH$_2$N(CH$_3$)$_2$, —CH$_2$N (C$_2$H$_5$)$_2$, —NHCOCH$_3$, —NHCOCF$_3$, —NHCOC$_2$H$_5$, —NHCOC$_3$H$_7$, —NHCOCH(CH$_3$)$_2$, —NHCOC(CH$_3$)$_3$, —CONH$_2$, —CONHCH$_3$, —CONHC$_2$H$_5$, —CONHC$_3$H$_7$, —CONHCH(CH$_3$)$_2$, —CONH-cyclo-C$_3$H$_5$, —CONHC (CH$_3$)$_3$, —CON(CH$_3$)$_2$, —CON(C$_2$H$_5$)$_2$, —CON(C$_3$H$_7$)$_2$, —CON[CH(CH$_3$)$_2$]$_2$, —CON[C(CH$_3$)$_3$]$_2$, —SO$_2$NH$_2$, —SO$_2$NHCH$_3$, —SO$_2$NHC$_2$H$_5$, —SO$_2$NHC$_3$H$_7$, —SO$_2$NHCH(CH$_3$)$_2$, —SO$_2$NH-cyclo-C$_3$H$_5$, —SO$_2$NHC —(CH₃)₃, —SO₂N(CH₃)₂, —SO₂N(C₂H₅)₂, —SO₂N(C₃H₇)₂, —SO₂N[CH(CH₃)₂]₂, —SO₂N[C(CH₃)₃]₂, —NHSO₂CH₃, —NHSO₂CF₃, —NHSO₂C₂H₅, —NHSO₂C₃H₇, —NHSO₂CH(CH₃)₂, —NHSO₂C(CH₃)₃, —CH=CH₂, —CH₂—CH=CH₂, —C(CH₃)=CH₂, —CH=CH—CH₃, —C≡CH, —C≡C—CH₃, —CH₂—C≡CH, -Ph, —O-Ph, —O—CH₂-Ph, —OSi(CH₃)₃, —OSi(C₂H₅)₃, —OSi(CH₃)₂C(CH₃)₃,

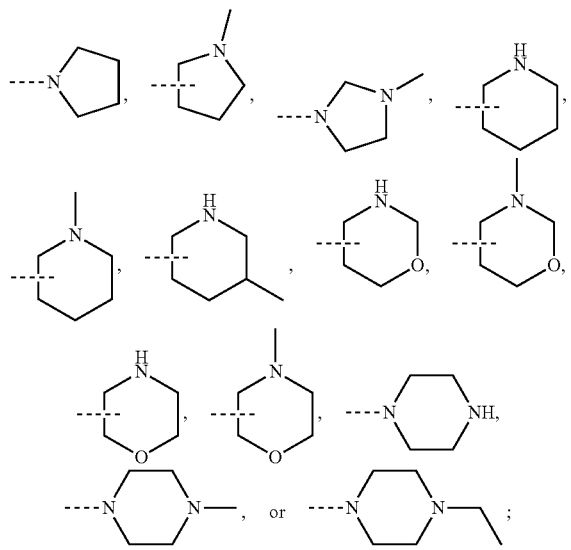

R²³-R³⁰ and R²³'-R³⁰' represent independently of each other
—H, —F, —Cl, —OH, —CN, —NO₂, —CH₃, —C₂H₅, —C₃H₇, —CH(CH₃)₂, —CF₃, —OCH₃, —OC₂H₅, —OC₃H₇, —OCH(CH₃)₂, —OCF₃, —OCH₂OCH₃, —O-cyclo-C₃H₅, —OCH₂-cyclo-C₃H₅, —COOCH₃, —COOC₂H₅, —OOC—CH₃, —OOC—CF₃, —OOC—C₂H₅, —OOC—C(CH₃)₃, —NH₂, —NHCH₃, —NHC₂H₅, —NHCH(CH₃)₂, —N(CH₃)₂, —N(C₂H₅)₂, —CH₂NH₂, —CH₂NHCH₃, —CH₂NHC₂H₅, —CH₂N(CH₃)₂, —CH₂N(C₂H₅)₂, —NHCOCH₃, —NHCOCF₃, —CONH₂, —CONHCH₃, —CONHC₂H₅, —CON(CH₃)₂, —CON(C₂H₅)₂, —SO₂NH₂, —SO₂NHCH₃, —SO₂NHC₂H₅, —SO₂N(CH₃)₂, —SO₂N(C₂H₅)₂, —NHSO₂CH₃, —NHSO₂CF₃, or —NHSO₂C₂H₅;

R^{N1}, R^{N1'}, R^{N2}, and R^{N2'} represent independently of each other
—H, —CH₃, —C₂H₅, —C₃H₇, —CH(CH₃)₂, -cyclo-C₃H₅, —COCH₃, —COCF₃, —COC(CH₃)₃, —OOC—CH₃, —OOC—CF₃, —OOC—C₂H₅, —OOC—C(CH₃)₃, —SO₂CH₃, or —SO₂CF₃;

or pharmaceutically acceptable salts thereof for use as pharmaceutically active agents applicable in medicine.

Surprisingly, it was found that the above-mentioned benzene sulfonamides of the formulae (I), (II), (III-1)-(III-8), (IV), (V) and (VI), as well as the pharmaceutical compositions comprising at least one of said benzene sulfonamides (I), (II), (III-1)-(III-8), (IV), (V) and (VI) are useful for treatment or prophylaxis of cancer, tumors and proliferative diseases, preferably cancer, tumors and proliferative diseases, especially caused by and/or associated with activating Ras mutations, and more preferably cancer, tumors and proliferative diseases caused by and/or associated with activating K-Ras mutations.

The term "mutation", as used herein, means a difference in the amino acid or nucleic acid sequence of a particular protein or nucleic acid (gene, RNA) relative to the wild-type protein or nucleic acid, respectively. A mutated protein or nucleic acid can be expressed from or found on one allele (heterozygous) or both alleles (homozygous) of a gene, and may be somatic or germ line. In the instant invention, mutations are generally somatic. Mutations include sequence rearrangements such as insertions, deletions, and point mutations.

The term "Ras mutation(s)" as used herein refers to a constitutive active form of the Ras protein caused by mutations mainly in the codons 12, 13, and 61. Most common ones are the following point mutations: G12D, G12V, G12C, G12A, G12S, G12R, G13D, G13C, Q61H.

Thus, the benzene disulfonamide compounds of the present invention can be used for prophylaxis and/or treatment of cancers, tumors and proliferative diseases or for the preparation of a pharmaceutical formulation for prophylaxis and/or treatment of cancers, tumors and proliferative diseases, preferably cancer, tumors and proliferative diseases caused by and/or associated with activating Ras mutations.

As already mentioned, K-Ras is the most frequently mutated oncogene is tumors. Cancer cell lines harboring K-Ras mutations have been classified based on K-Ras dependency for cell viability into K-Ras dependent and K-Ras independent groups (Cancer Cell 2009, 15, 489). Examples of K-Ras dependent cell lines include, but are not restricted to: PANC-1, Mia PaCa-2, Panc-Tu-I, BxPC-3. The compounds of general formula (I) are able to inhibit the proliferation of Ras dependent cells, leading to cell death.

More specifically, the cancers, tumors and proliferative diseases that can be treated and/or prevented by the inventive compounds are selected from the group comprising or consisting of: adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, non-small cell lung cancer (NSCLC), breast cancer, Burkitt's lymphoma, corpus cancer, CUP-syndrome (carcinoma of unknown primary), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, glioblastomas, gynecologic tumors, ear, nose and throat tumors, hematologic neoplasias, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's), lymphomas, stomach cancer, malignant melanoma, malignant neoplasia, malignant tumors gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, squamous cell carcinoma of the head and neck (SCCHN), prostate cancer, pharyngeal cancer, rectal carcinoma, retinoblastoma, vaginal cancer, thyroid carcinoma, Schneeberger disease, esophageal cancer, spinalioma, T-cell lymphoma (mycosis fungoides), thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma and tongue cancer.

Cancer cells often depend on the survival signaling emanating from oncogene products, particularly from oncogenic K-Ras, for their survival. The induction of programmed cell death by the loss of such survival signaling, as disclosed for the compounds of the present invention, is especially useful in the treatment of cancer by inducing the death of oncogenic Ras dependent malignant cells. Since all kinds of cancer cells are destroyable through the induction of programmed cell death, all different kinds of cancer and abnormal proliferating cells can be treated with the compounds of the present invention.

In one embodiment, the present invention is directed to a pharmaceutical composition comprising at least one compound of the present invention as active ingredient, together with at least one pharmaceutically acceptable carrier, excipient and/or diluent.

Said pharmaceutical compositions can be used for prophylaxis and/or treatment of cancers, tumors and proliferative diseases or for the preparation of a pharmaceutical formulation for prophylaxis and/or treatment of cancers, tumors and proliferative diseases, preferably cancer, tumors and proliferative diseases caused by and/or associated with activating Ras mutations.

The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes use of a compound of the formula (I) for the preparation of a pharmaceutical formulation for use in the prophylaxis, and/or treatment of cancer, tumors and proliferative diseases.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention.

The pharmaceutical compositions according to the present invention containing at least one compound according to the present invention as active ingredient will typically be administered together with suitable carrier materials selected with respect to the intended form of administration, i.e. for oral administration in the form of tablets, capsules (either solid filled, semi-solid filled or liquid filled), powders for constitution, extrudates, deposits, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like.

Moreover, suitable binders, lubricants, disintegrating agents and coloring agents may also be incorporated into the tablet or capsule. Powders and tablets may contain about 5 to about 95 weight % of the inventive benzene disulfonamde of general formula (I) as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimize the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration. Aerosol preparations suitable for inhalation may include solutions and solids in powder form, which may be present in combination with a pharmaceutically acceptable carrier such as an inert, compressed gas, e.g. nitrogen. For preparing suppositories, a low melting fat or wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methyl cellulose, polyvinyl alcohols, or denatured gelatins or starch for holding or containing compositions comprising the active ingredient(s). Capsules with hard shells are typically made of blended of relatively high gel strength gelatins from bones or pork skin. The capsule itself may contain small amounts of dyes, opaquing agents, plasticisers and/or preservatives. Under tablet a compressed or moulded solid dosage form is understood, which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilized in a hydrophilic semi-solid matrix. Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses, such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances, which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

Another aspect of this invention provides a method of treating a disease or a medical condition in a patient comprising administering to said patient one or more compound(s) of general formula (I) in an amount effective to treat or prevent said disease or condition.

In a particular embodiment, the invention provides a method of treating or preventing of a proliferative disease, a tumor and/or a cancer in a patient, which comprises administering to said patient a therapeutically effective amount of at least one compound of general formula (I).

The term "effective amount" means an amount of compound that, when administered to a patient in need of such treatment, is sufficient to
(i) treat or prevent a particular disease, condition, or disorder;
(ii) attenuate, ameliorate, or eliminate one or more symptoms of the particular disease, condition, or disorder; or
(iii) prevent or delay the onset of one or more symptoms of the particular disease, condition, or disorder described herein.

The amount of a compound of general formula (I) that will correspond to such an amount will vary depending upon factors such as the particular compound, disease condition and its severity, the identity (e.g., weight) of the patient in need of treatment, but can nevertheless be routinely determined by one skilled in the art.

A) and B) Release by Arl2 under equilibrium conditions of 1L*, 2L* and 8L*. 0.2 µM fluorescently labeled inhibitor was placed in a cuvette followed by the addition of 0.5 µM PDE6δ resulting in the increase of the polarization signal due to complex formation. The formed complex was titrated with Arl2 (1 and 5 µM) as indicated. C) and D) Kinetics of release by Arl2 under competition with an unlabeled inhibitor. A mixture of 0.5 µM Arl2 and 40 µM compound 16 was added to a preformed complex of 0.2 µM of the fluorescently labeled inhibitor and 0.5 µM PDE66. The Arl2-mediated release was monitored by the decrease of the polarization. Dissociation rate constants ($k_{off}$) were obtained by single exponential fitting of the data. E) and F) Representative melting curves for as observed in a thermal protein profiling experiment. Melting curves for the DMSO controls are shown in dotted line and melting curves after treatment with compound 22 are shown in solid line.

Figure 1:
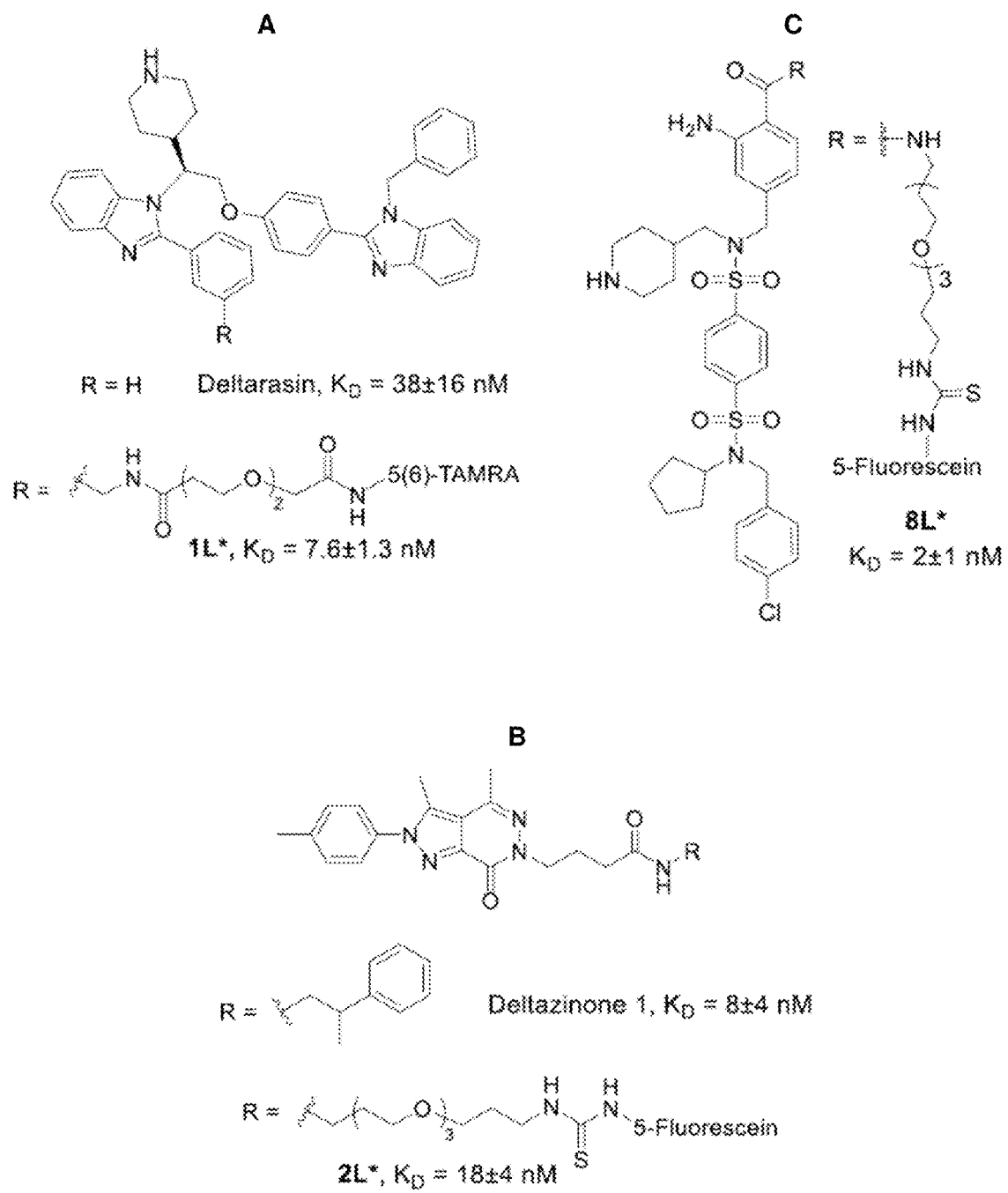
FIG. 1 shows chemical structures and binding affinities ($K_D$, determined by competitive fluorescence polarization assay as described in the biological examples) of Deltarasin and labeled Deltarasin (A, 1L*), Deltazinone 1 and labeled Deltazinone 1 (B, 2L*), and a fluorescently labeled disulfonamides derivative (C, 8L*).
Figure 2:
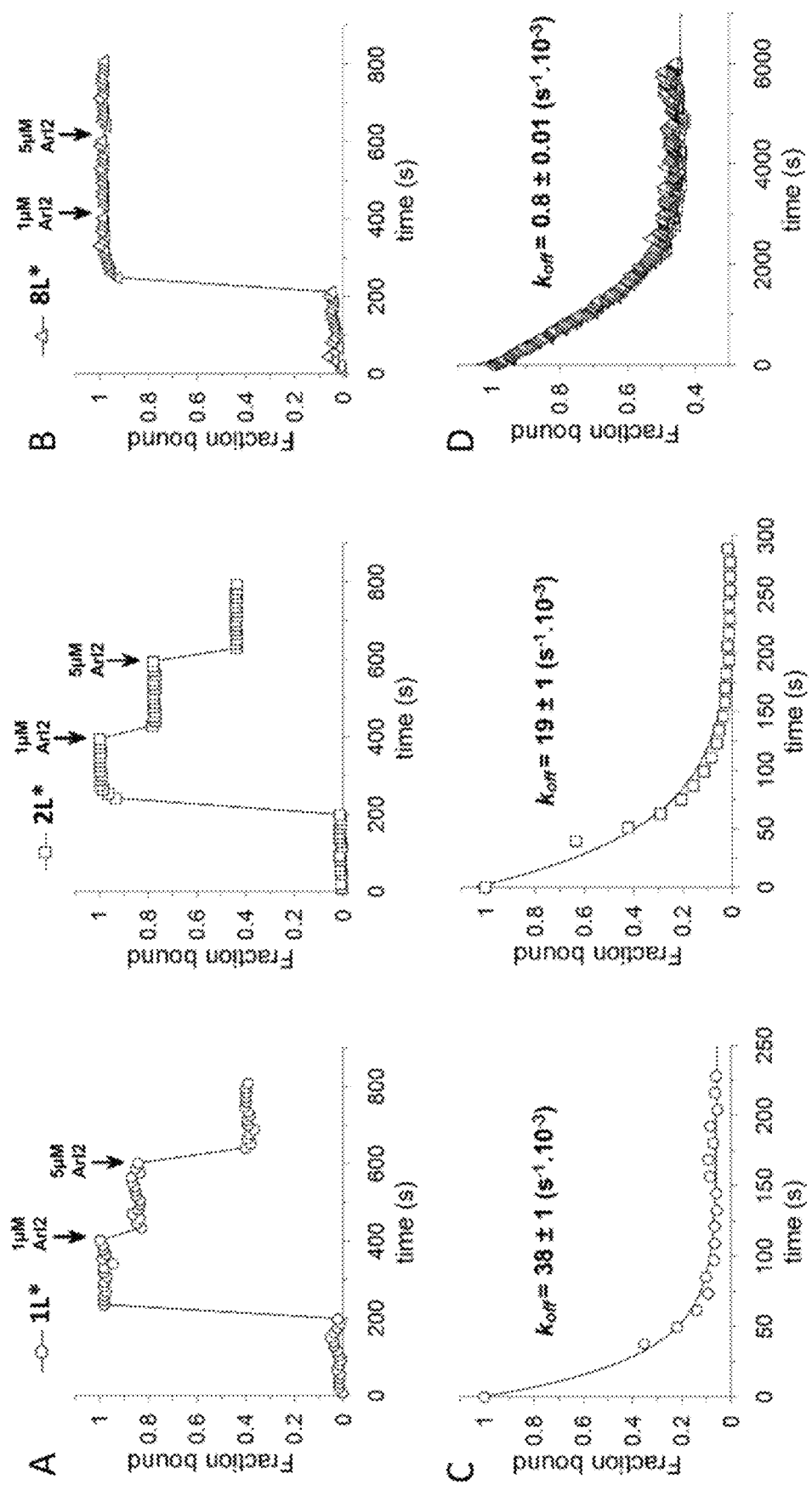
FIG. 2: Arl2-mediated displacement of the different chemotypes and CETSA melting curves.
Figure 2:
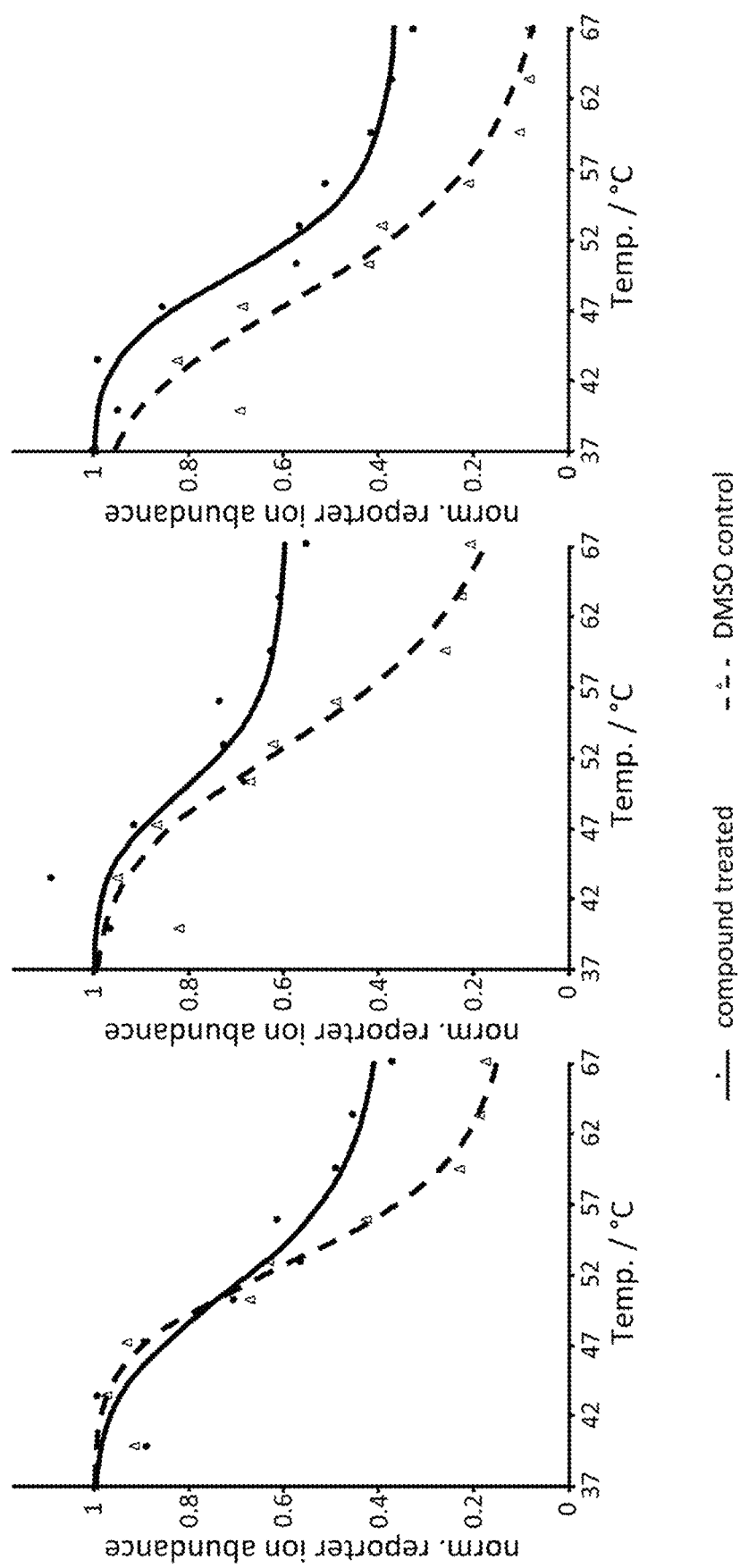
Figure 2:
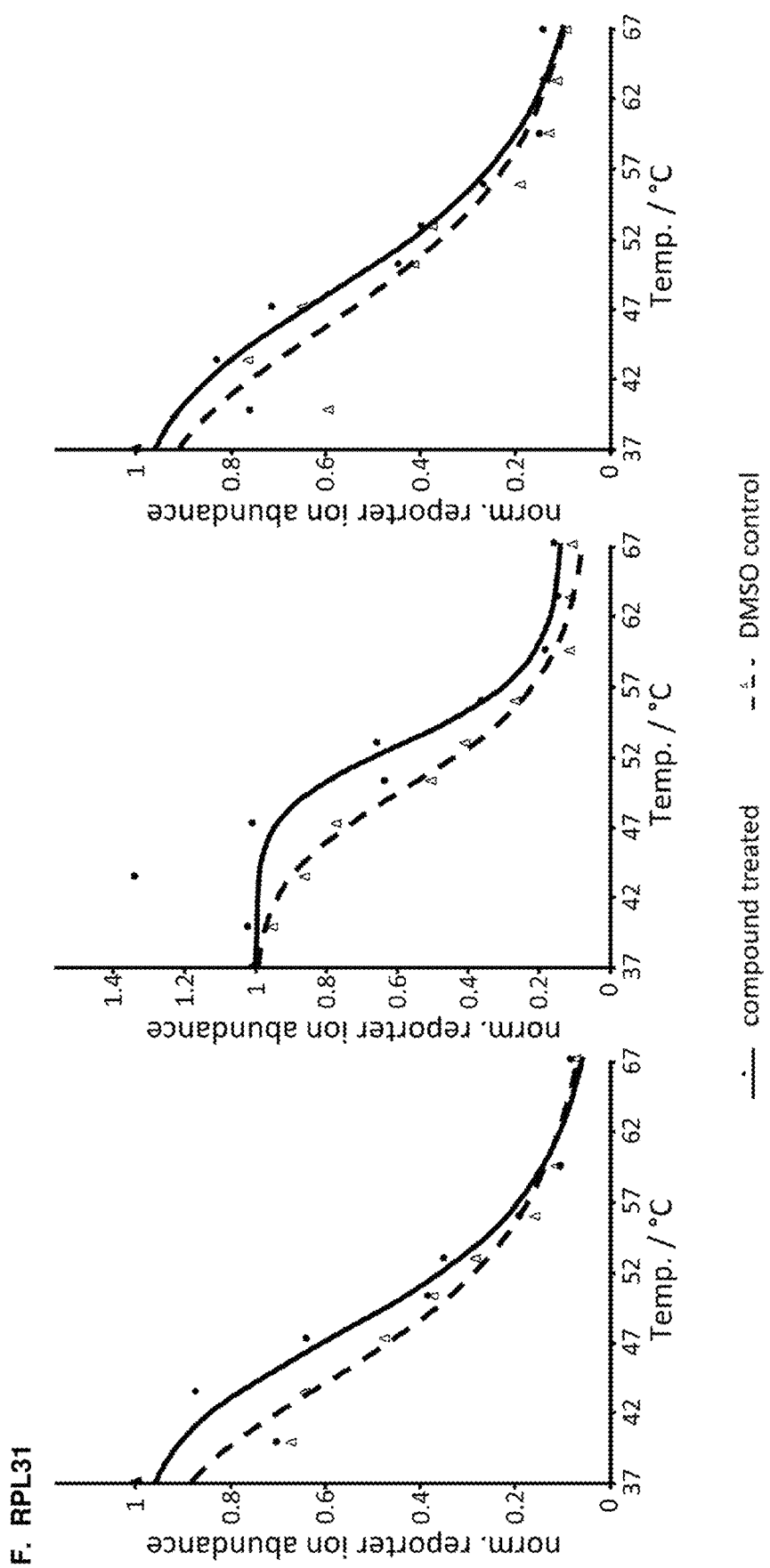
Figure 3:
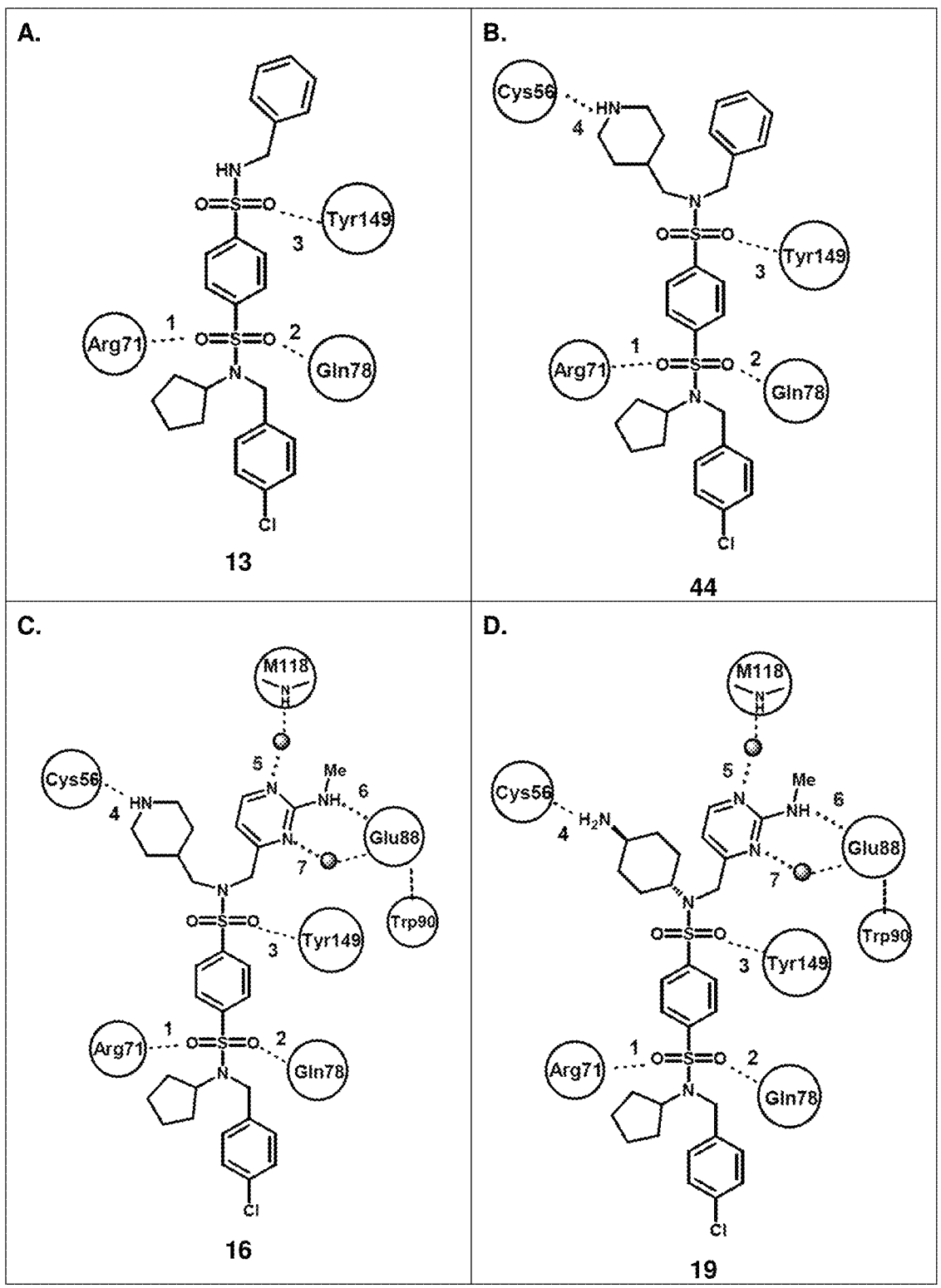
Figure 3:
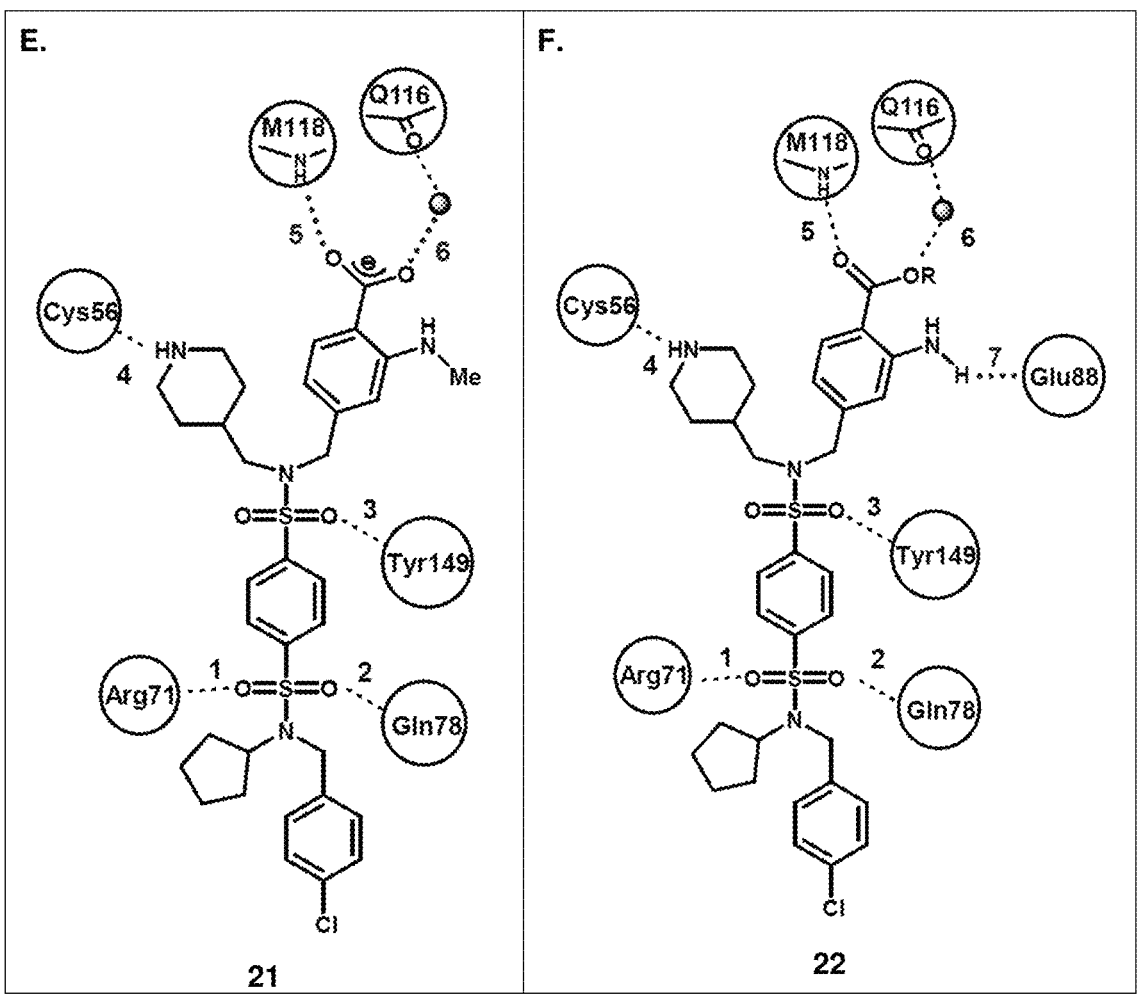

FIG. 3 shows chemical structures, schematic binding mode of compounds 13, 16, 19, 21, 22 and 44 into the prenyl binding site of PDE66. Said compounds can have up to 7H-bonding interactions (1-7) with amino acids of prenyl binding site such as Cys56, Arg71, Gln78, Glu88, Q116, M118, and Try149.

Figure 4:
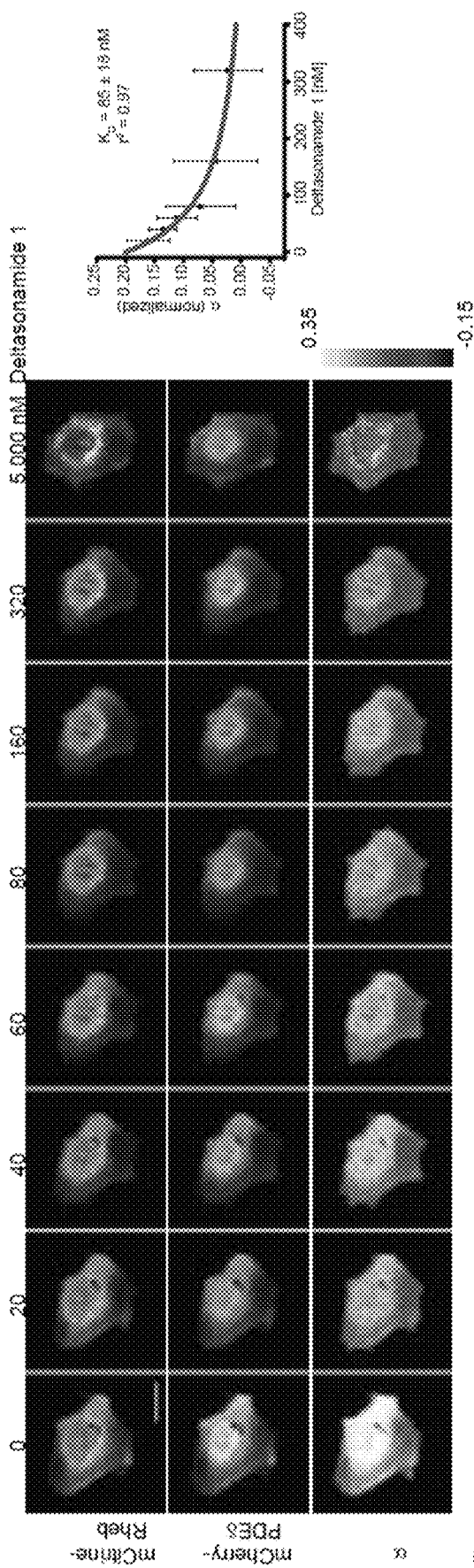
Figure 4:
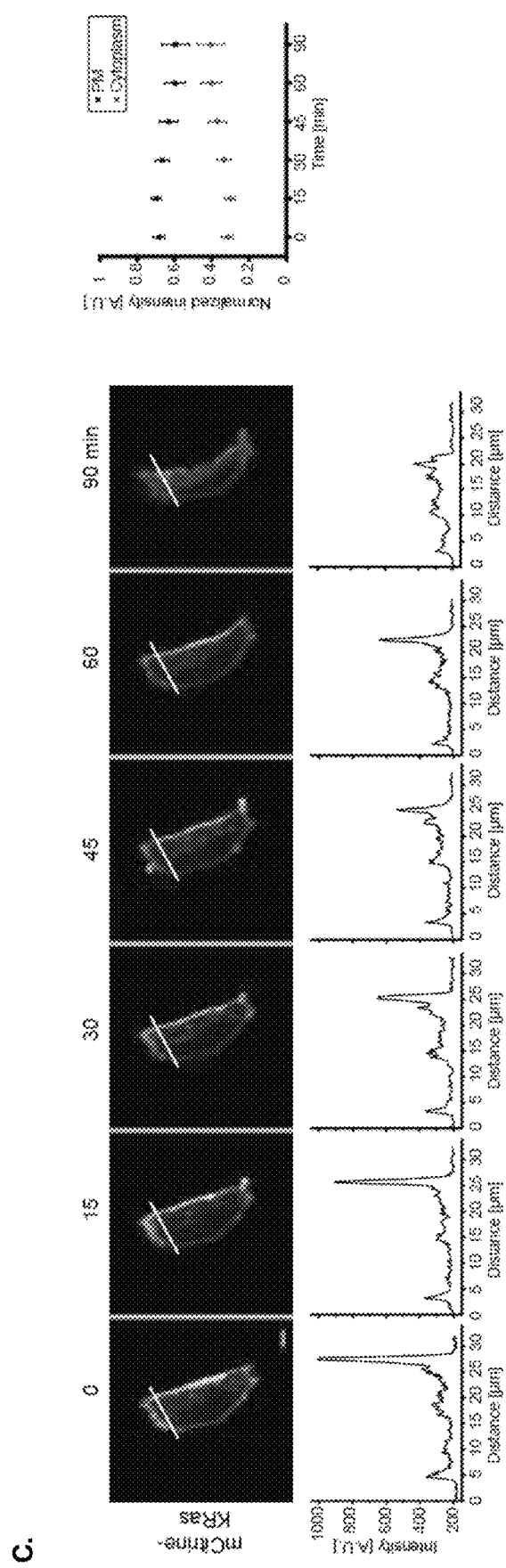

FIG. 4: Compounds 16 and 19 (Deltasonamides 1 and 2) inhibit the interaction between Ras proteins and PDE6δ in cells and result in delocalization.

A) and B) Left panels, FLIM measurements of the mCitrine-RheB and mCherry-PDE6δ interaction in dependence on Deltasonamide dose. Upper and middle rows: fluorescence intensity of mCitrine-RheB and mCherry-PDE6δ. Lower rows: molar fraction of interacting mCitrine-RheB and mCherry-PDE6δ. Inhibitor concentrations are indicated above each image in nM. Right panels, fit of averaged dose-response of five cells to a binding model (see methods) yielded an "in cell KD" of 85±18 nM (s.e.m.) for compound 16 (Deltasonamdie 1) and 61±5 nM for compound 19 (Deltasonamdie 2).

C) Time series of mCitrine-KRas redistribution upon administration of 5 µM compound 19 (Deltasonamdie 2) in MiaPaCa-2. Upper row: fluorescence intensity of mCitrine-KRas, lower row: intensity profiles of corresponding ROI in the images: Right panel, Kras mean intensity±s.d. at the plasma membrane (black) and inside the cell (red) over time (N=8).

Figure 5:
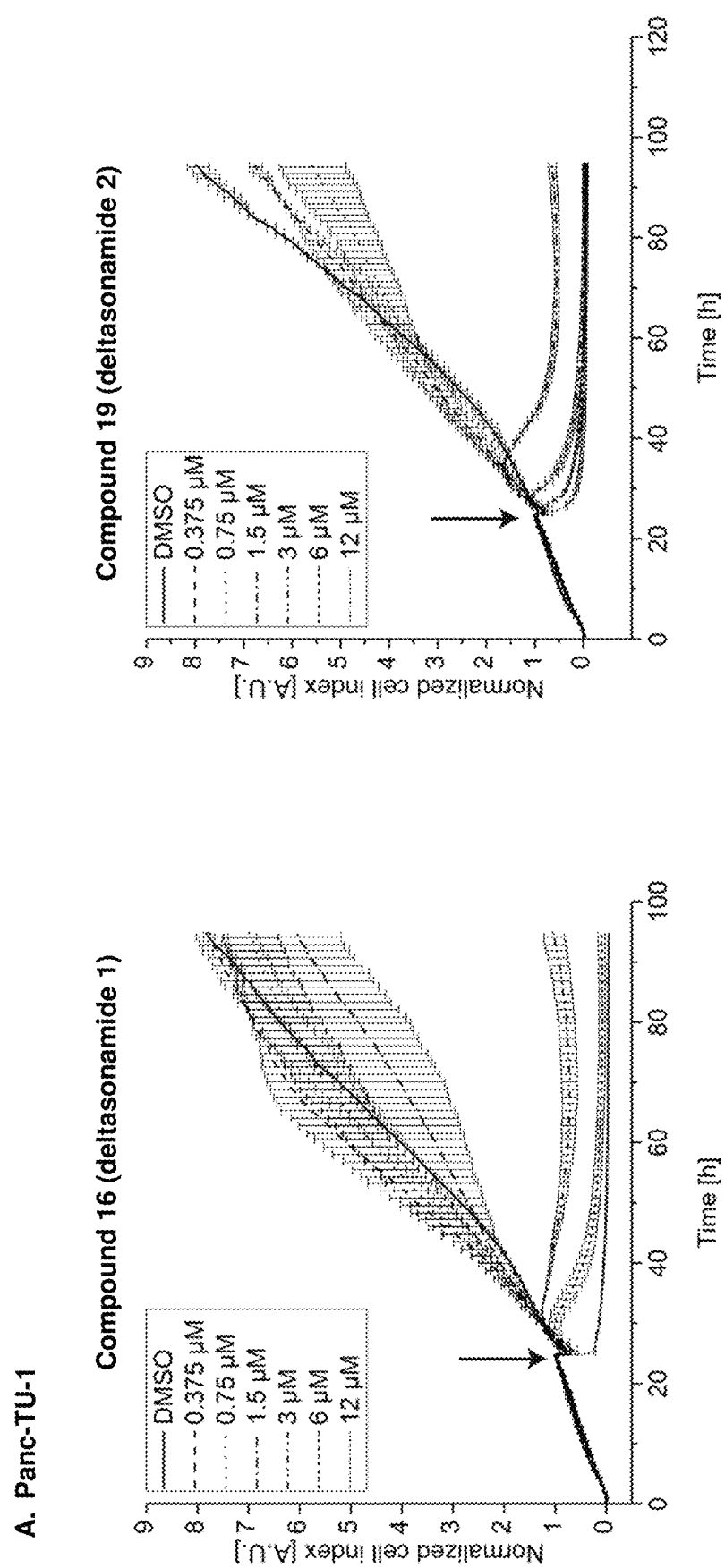
Figure 5:
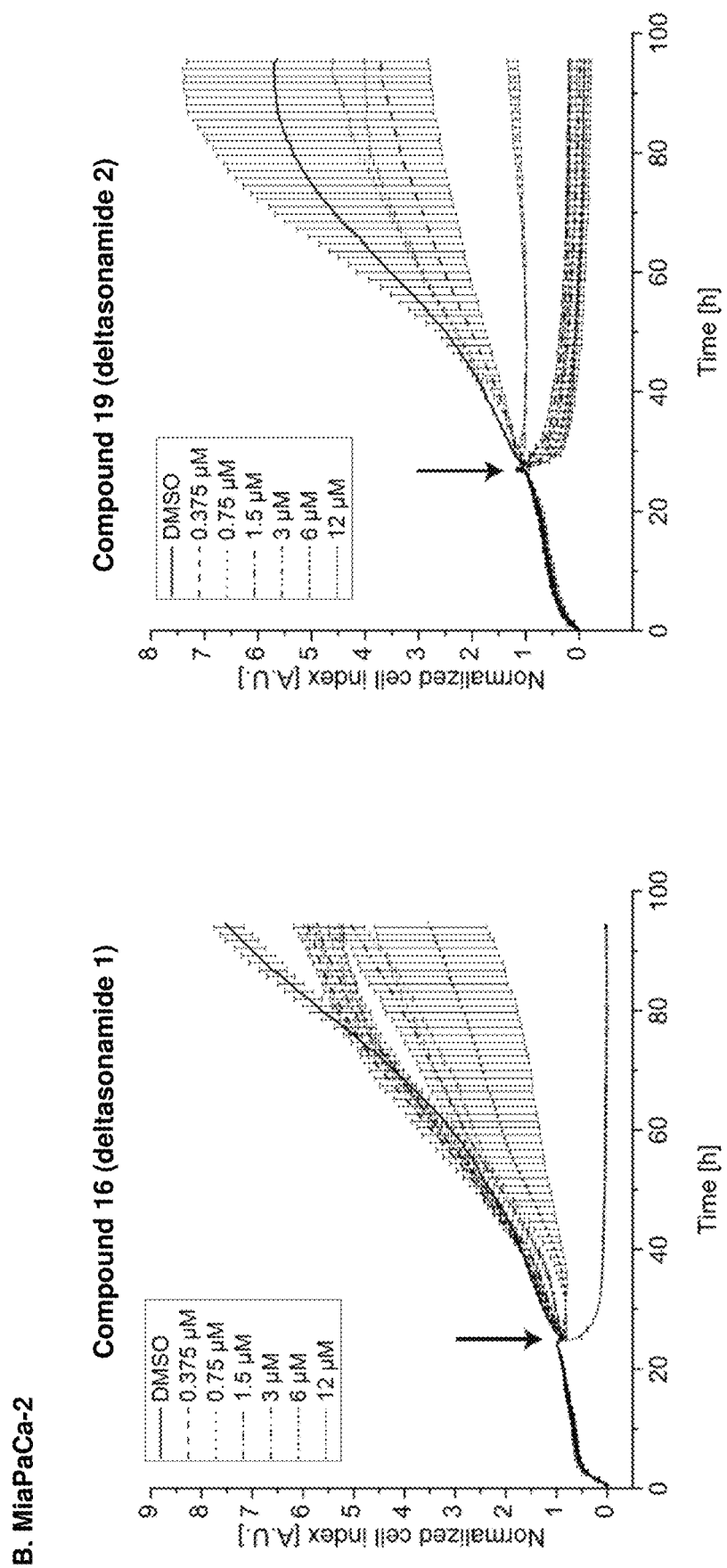
Figure 5:
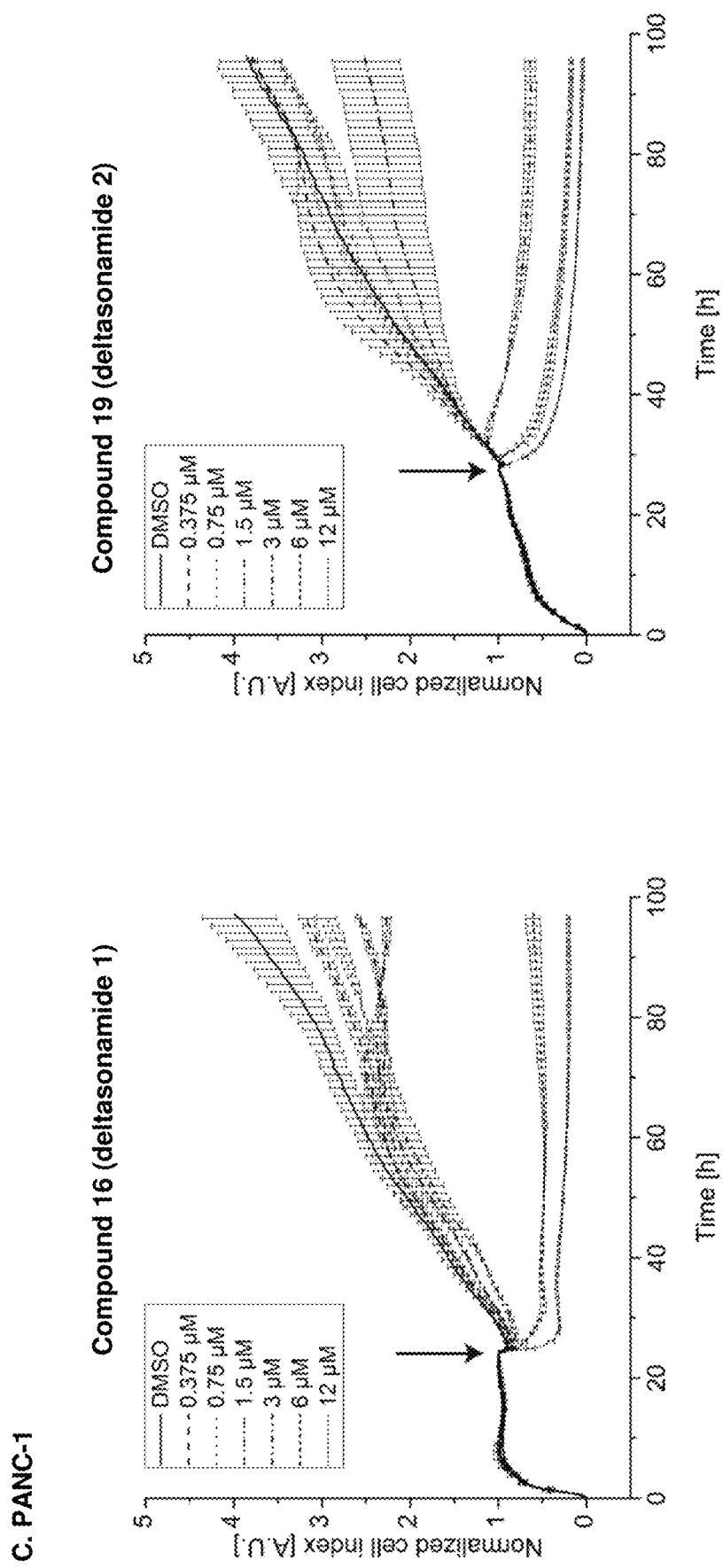
Figure 5:
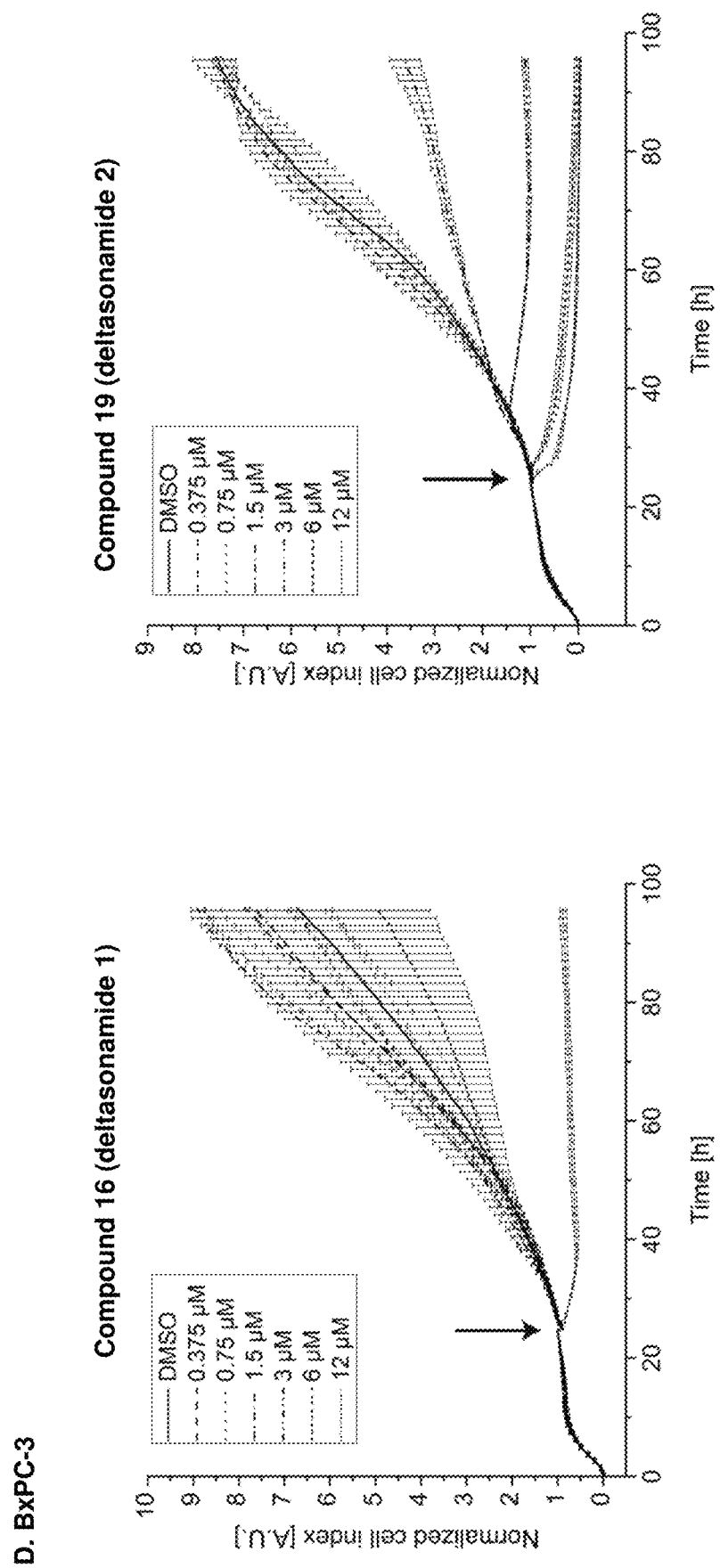
Figure 5:
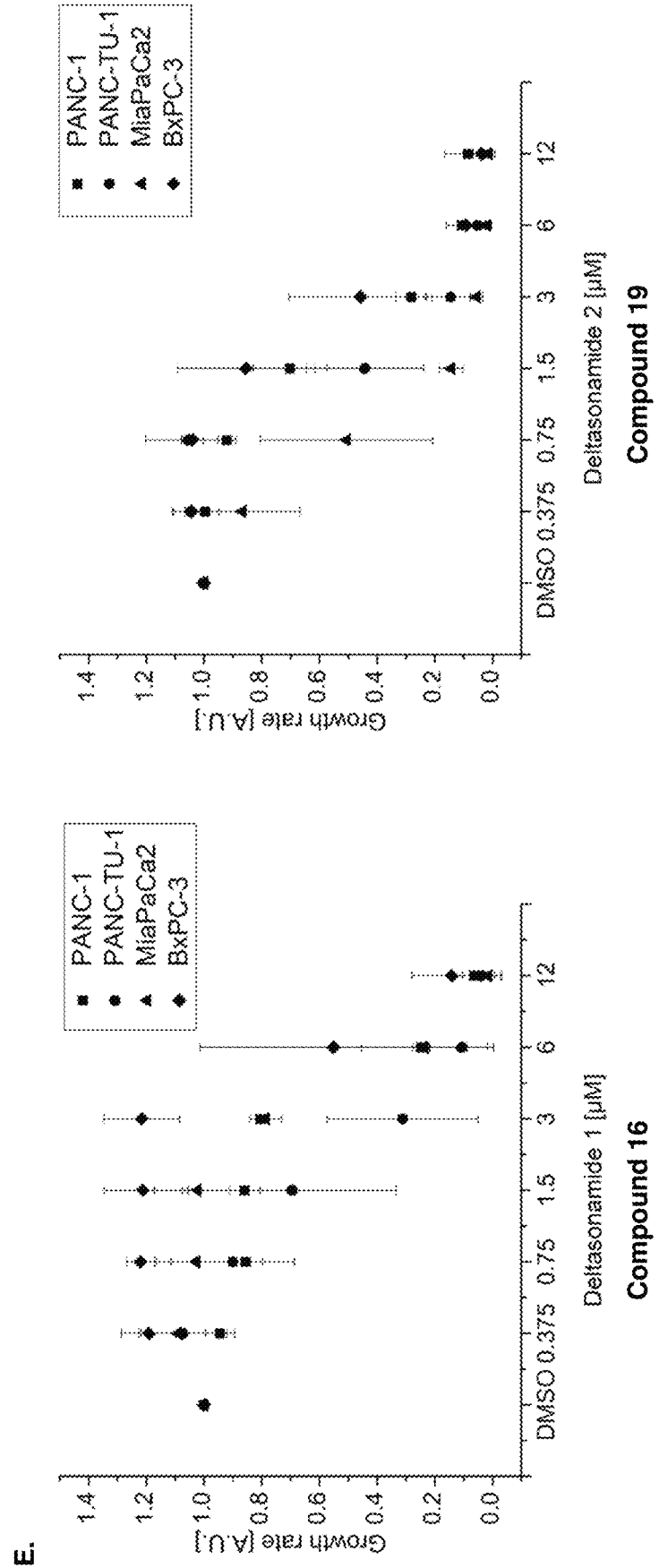

FIG. 5: Compounds 16 and 19 (Deltasonamides 1 and 2) inhibit proliferation of human pancreatic cancer cell lines:

A)-D) RTCA of hPDAC cell lines with distinct KRas dependency treated with different doses of compound 16 (Deltasonamide 1, left column) or compound 19 (Deltasonamide 2, right column). Cell indices±s.d. were measured in duplicates and normalized to the time point of drug administration.

E) Growth rate±s.d. in dependence of Deltasonamide dose. The growth rates were estimated by area under the curve integration over 60 h after drug administration and normalized to DMSO control.

Figure 6:
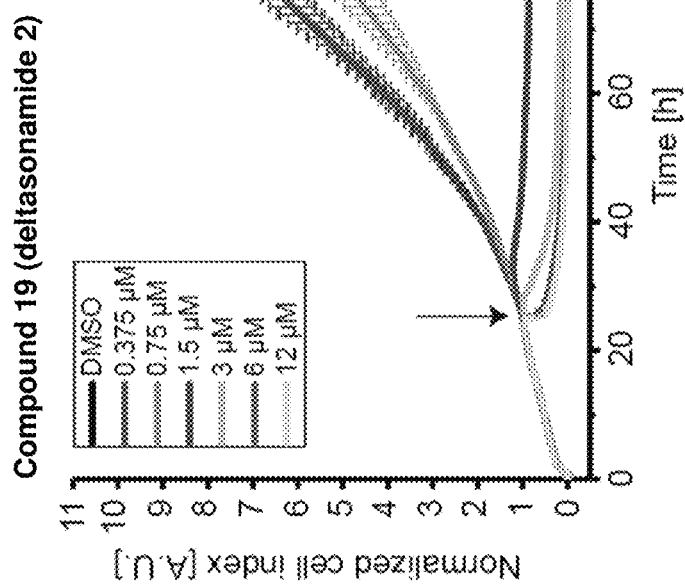
Figure 6:
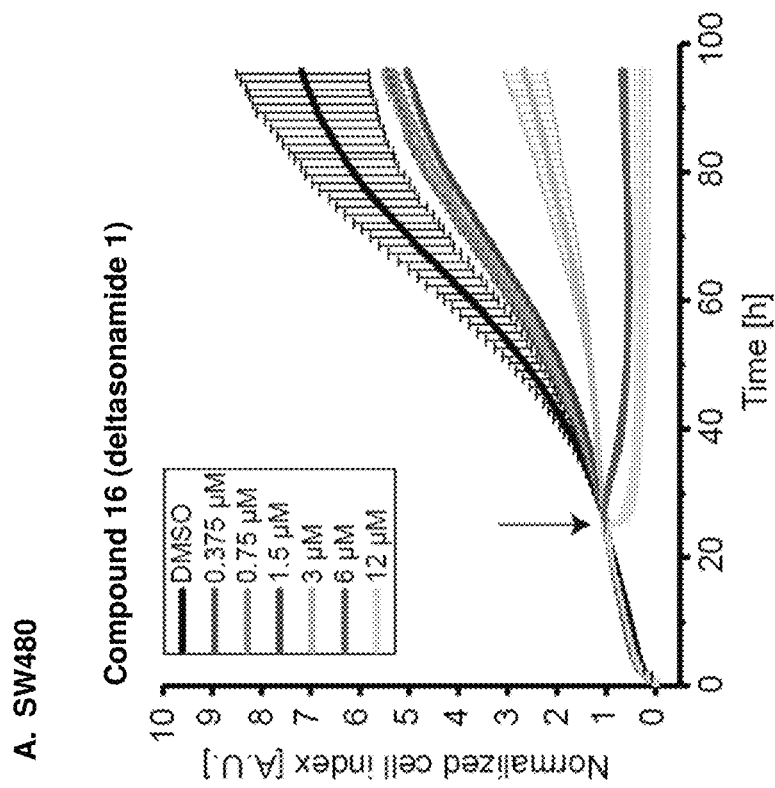
Figure 6:
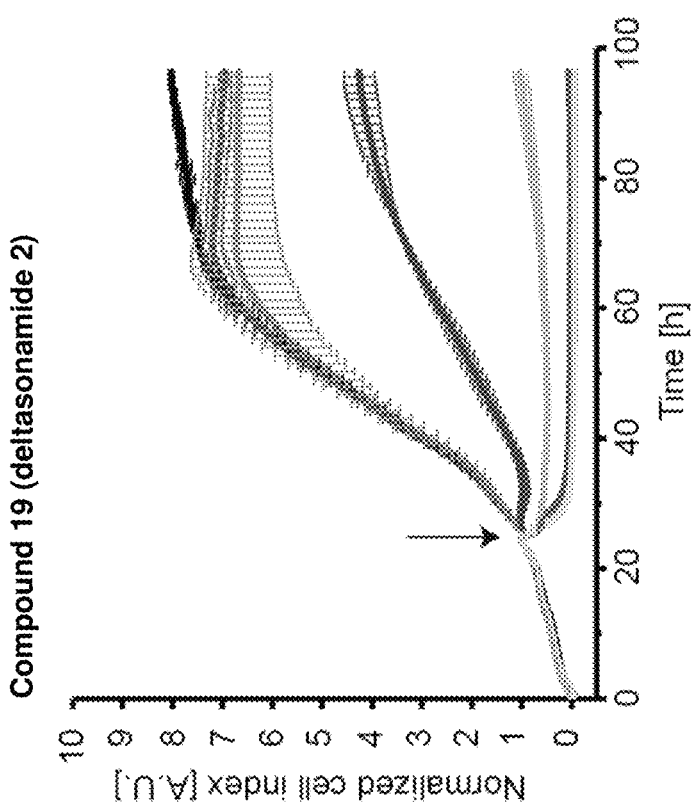
Figure 6:
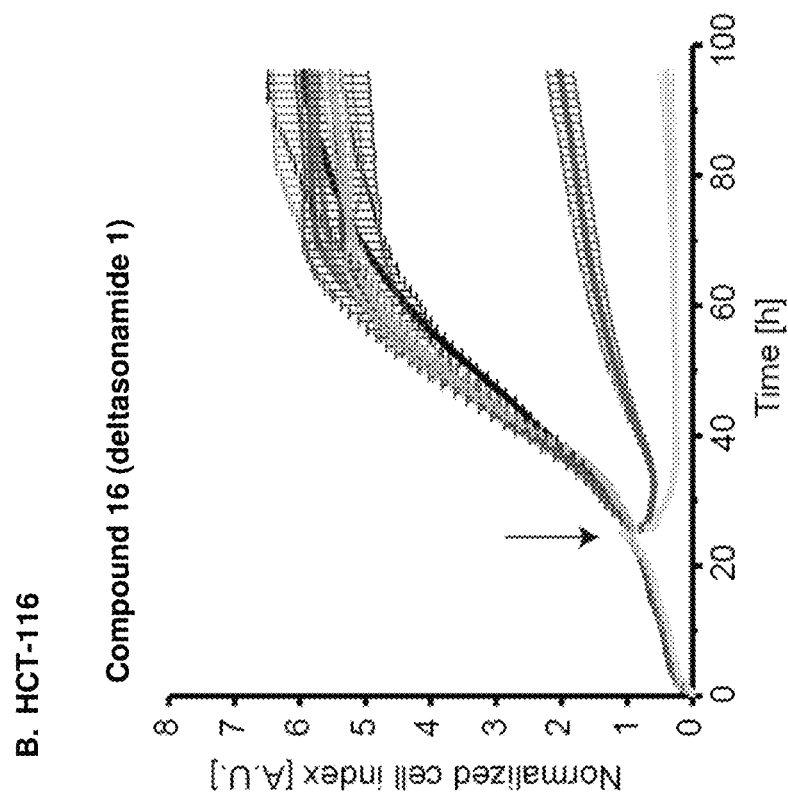
Figure 6:
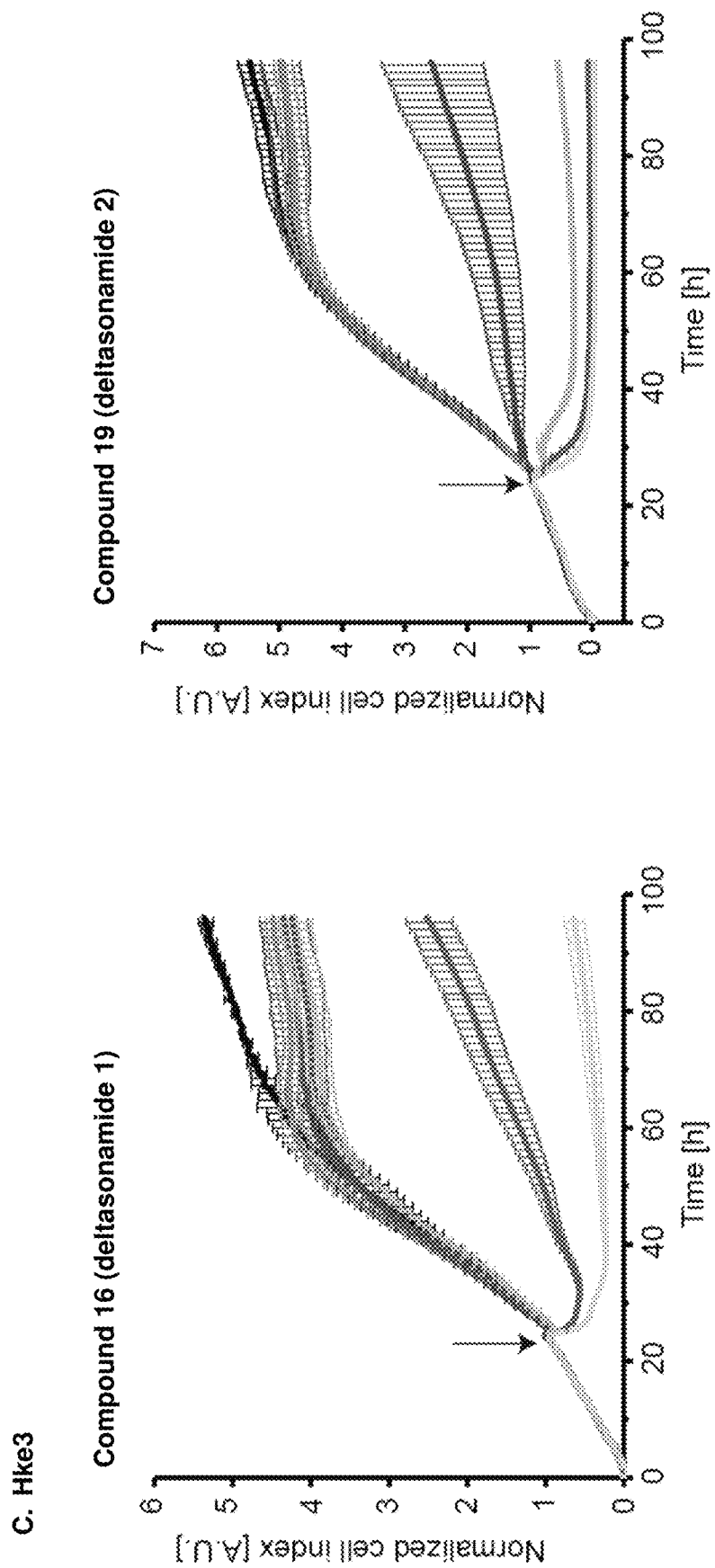
Figure 6:
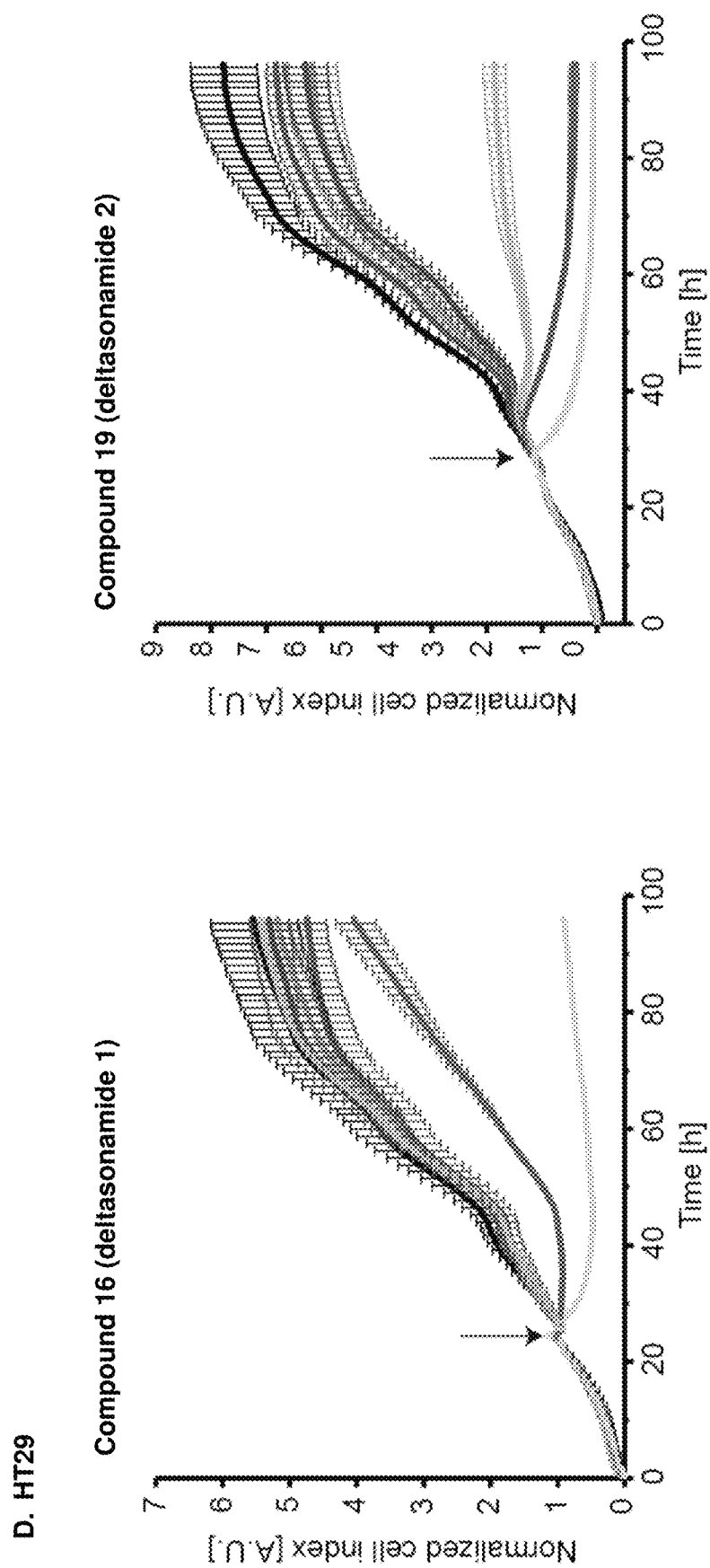
Figure 6:
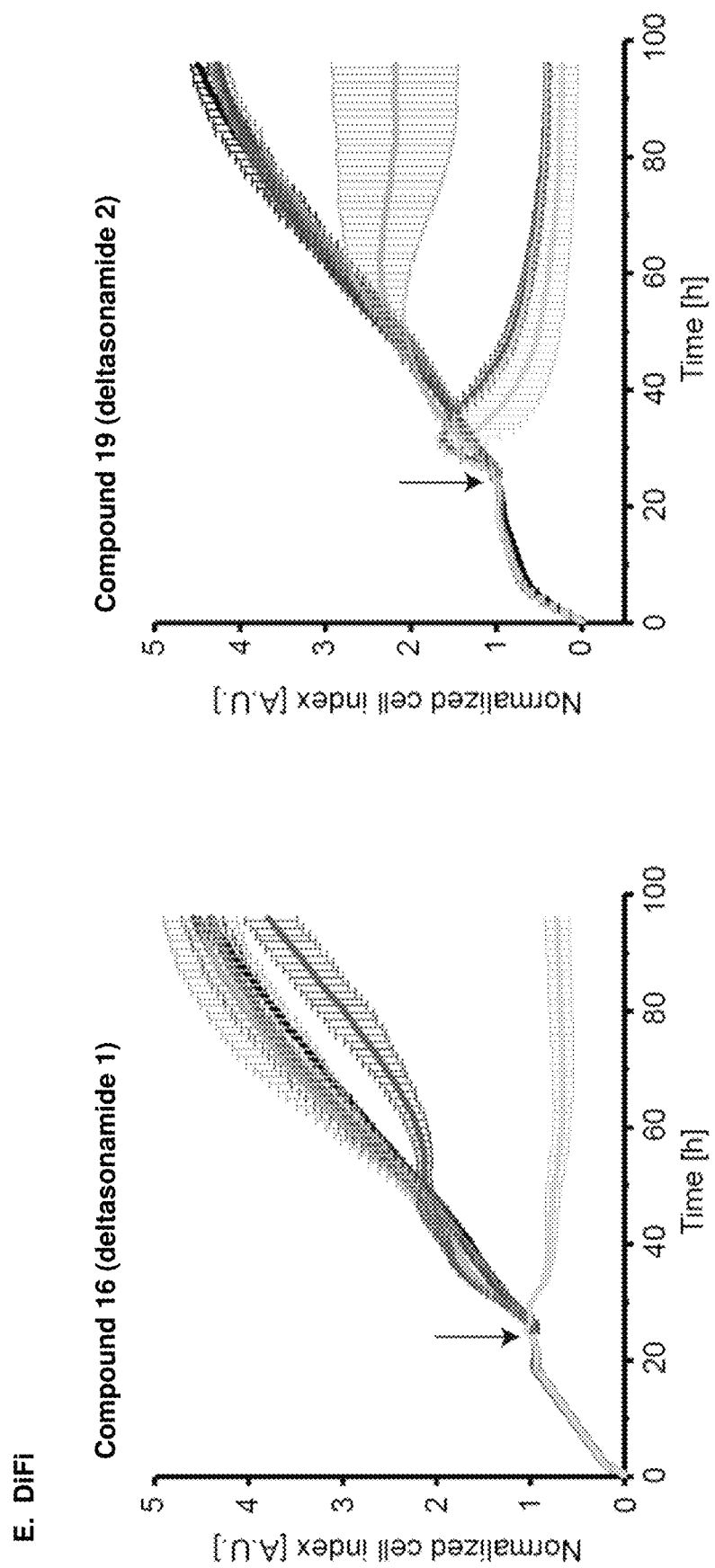
Figure 6:
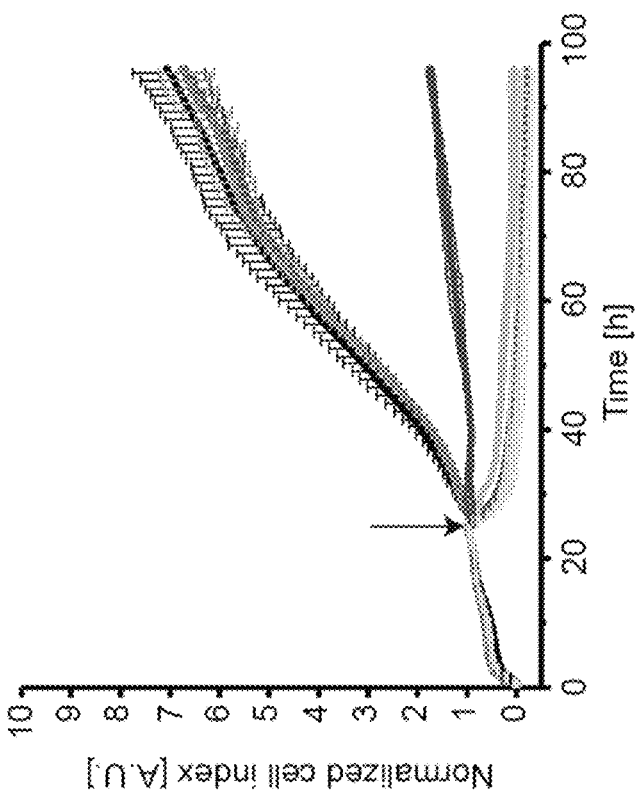
Figure 6:
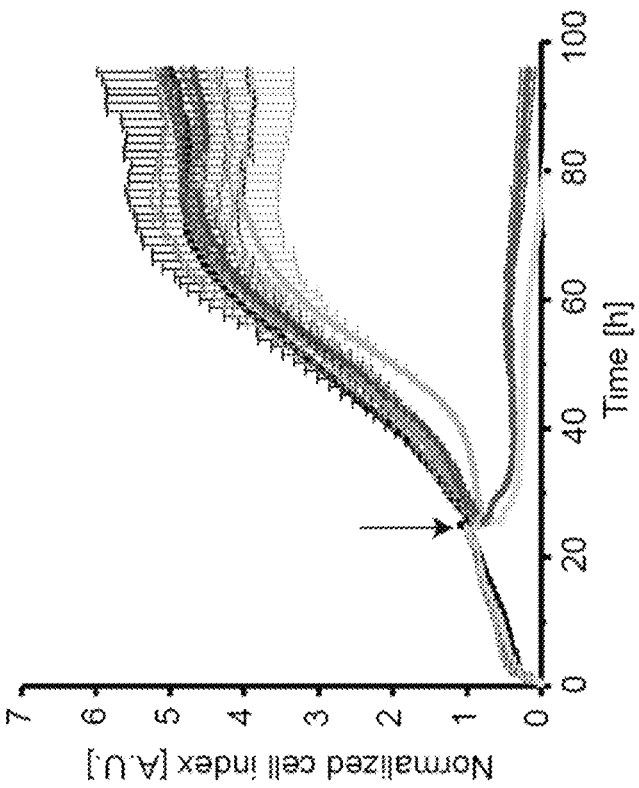
Figure 6:
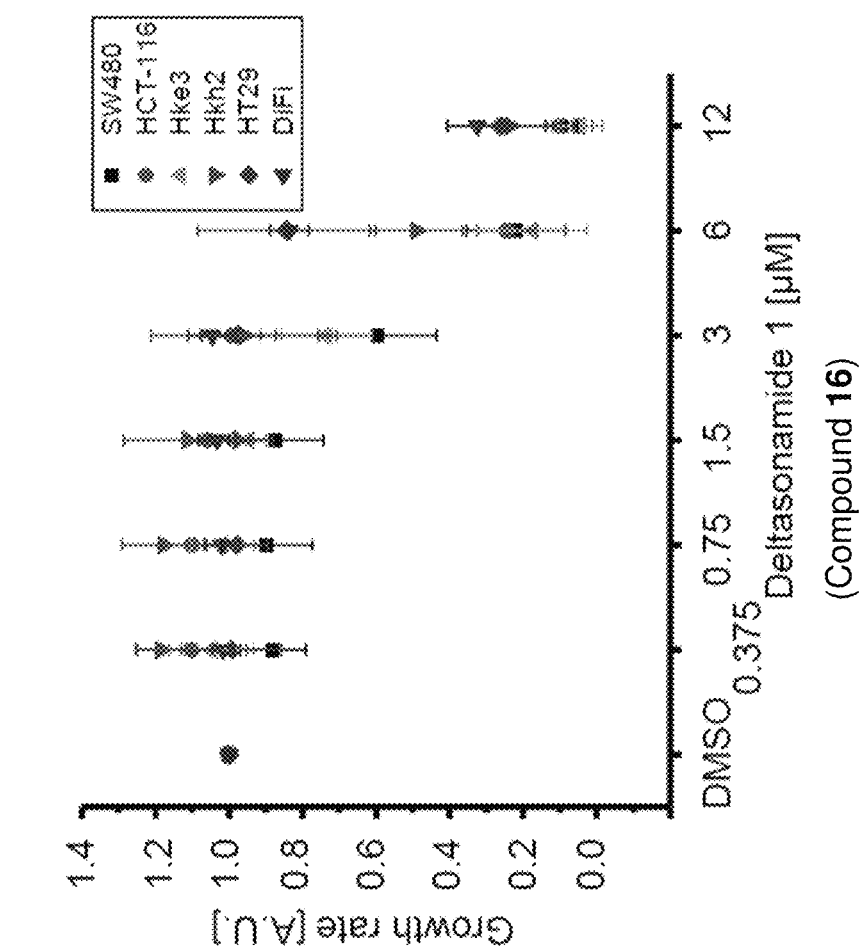

FIG. 6: Compounds 16 and 19 (Deltasonamides 1 and 2) inhibit proliferation of human colorectal cancer cell lines:

A) RTCA profiles of SW480 cell lines with distinct KRas dependency treated with different doses of compound 16 (Deltasonamide 1, left column) or compound 19 (Deltasonamide 2, right column). Cell indices±s.d. were measured in duplicates and normalized to the time point of drug administration (arrow).

B) RTCA profiles of HCT-116 cell lines with distinct KRas dependency treated with different doses of compound 16 (Deltasonamide 1, left column) or compound 19 (Deltasonamide 2, right column). Cell indices±s.d. were measured in duplicates and normalized to the time point of drug administration (arrow).

C) RTCA profiles of Hke3 cell lines with distinct KRas dependency treated with different doses of compound 16 (Deltasonamide 1, left column) or compound 19 (Deltasonamide 2, right column). Cell indices±s.d. were measured in duplicates and normalized to the time point of drug administration (arrow).

D) RTCA profiles of HT29 cell lines with distinct KRas dependency treated with different doses of compound 16 (Deltasonamide 1, left column) or compound 19 (Deltasonamide 2, right column). Cell indices±s.d. were measured in duplicates and normalized to the time point of drug administration (arrow).

E) RTCA profiles of DiFi cell lines with distinct KRas dependency treated with different doses of compound 16 (Deltasonamide 1, left column) or compound 19 (Deltasonamide 2, right column). Cell indices±s.d. were measured in duplicates and normalized to the time point of drug administration (arrow).

F) RTCA profiles of Hkh2 cell lines with distinct KRas dependency treated with different doses of compound 16 (Deltasonamide 1, left column) or compound 19 (Deltasonamide 2, right column). Cell indices±s.d. were measured in duplicates and normalized to the time point of drug administration (arrow).

G) Growth rate±s.d. in dependence on inhibitor dose of Deltasonamide 1. The growth rates were determined by integration of the area below the RTCA curves over 60 h after drug administration (arrow) and normalized to DMSO control.

Figure 7:
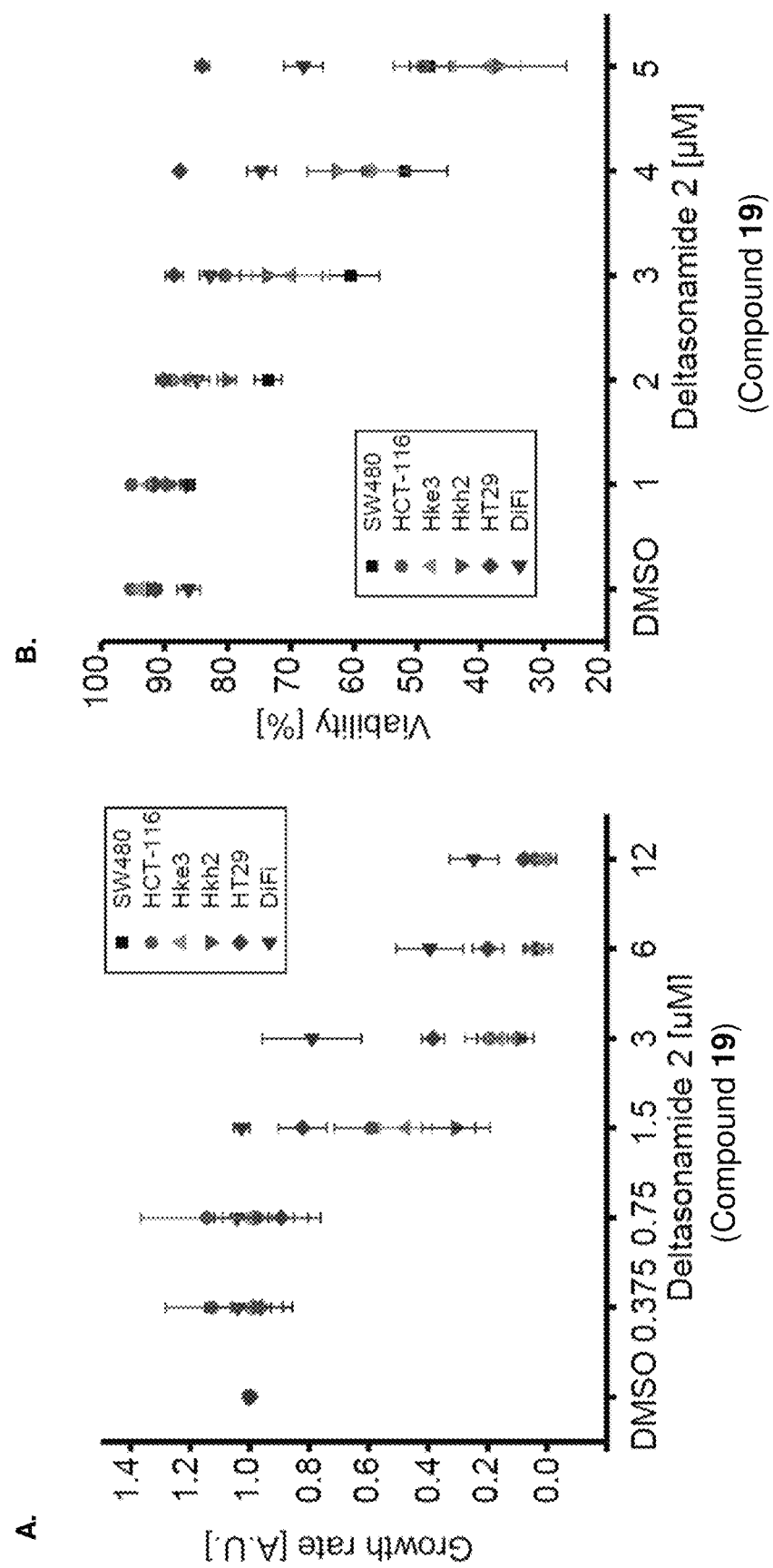
Figure 7:
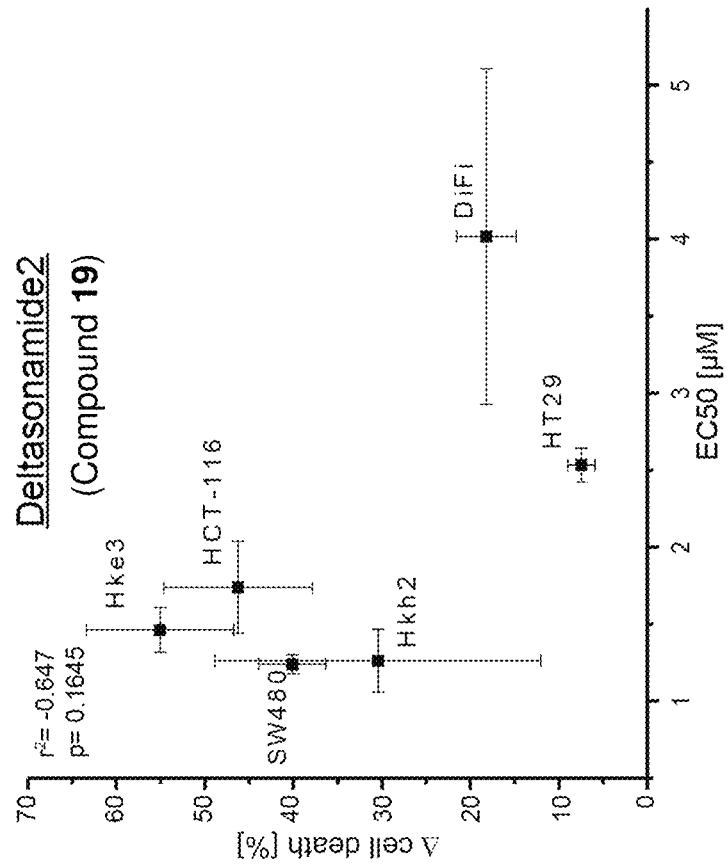

FIG. 7: Does-dependent inhibition of proliferation and apoptosis induction in human colorectal cancer cell lines by compound 19 (Deltasonamide 2):

A) Growth rate±s.d. in dependence on inhibitor dose of compound 19 (Deltasonamide 2). The growth rates were determined by integration of the area below the RTCA curves over 60 h after drug administration and normalized to DMSO control.

B) Cell viability±s.d. in dependence on inhibitor dose of compound 19 (Deltasonamide 2). In CRC cell lines after 24 h of drug administration. Cell death was determined by viability staining using 7-AAD. DMSO was used as mock control.

C) Correlation of A Cell death±s.d. versus $EC_{50}$±s.d for compound 19 (Deltasonamide 2). A Cell death was calculated between DMSO controls and the highest used inhibitor concentration, respectively. $EC_{50}$ values were determined by sigmoidal curve fit of the growth rates depicted in FIG. 7A.

D) Four-dimensional correlation of growth rate and cell viability in dependence of inhibitor does and CRC cell line for compound 19 (Deltasonamide 2). Dot size is proportional to applied inhibitor concentration.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

A. Chemical Synthesis

General Information:

All reactions involving air- or moisture-sensitive reagents or intermediates were carried out in flame dried glassware under an argon atmosphere. Dry solvents (THF, toluene, MeOH, DMF) were used as commercially available; $CH_2Cl_2$ was purified by the Solvent Purification System M-BRAUN Glovebox Technology SPS-800. Analytical thin-layer chromatography (TLC) was performed on Merck silica gel aluminium plates with F-254 indicator. Compounds were visualized by irradiation with UV light or potassium permanganate staining. Column chromatography was performed using silica gel Merck 60 (particle size 0.040-0.063 mm). $^1$H-NMR and $^{13}$C-NMR were recorded on a Bruker DRX400 (400 MHz), Bruker DRX500 (500 MHz), INOVA500 (500 MHz) and DRX600 (600 MHz) at 300 K using CDCl$_3$, CD$_3$OD or (CD$_3$)$_2$SO as solvents. All resonances are reported relative to TMS. Spectra were calibrated relative to solvent's residual proton and carbon chemical shift: CDCl$_3$ (δ=7.26 ppm for $^1$H NMR and δ=77.16 ppm for $^{13}$C NMR); CD$_3$OD (δ=3.31 ppm for $^1$H NMR and δ=49.00 ppm for $^{13}$C NMR); (CD$_3$)$_2$SO: δ=2.50 ppm for $^1$H NMR and δ=39.52 ppm for $^{13}$C NMR). Multiplicities are indicated as: br s (broadened singlet), s (singlet), d (doublet), t (triplet), q (quartet), quin (quintet), m (multiplet); and coupling constants (J) are given in Hertz (Hz). High resolution mass spectra were recorded on a LTQ Orbitrap mass spectrometer coupled to an Acceka HPLC-System (HPLC column: Hypersyl GOLD, 50 mm×1 mm, particle size 1.9 μm, ionization method: electron spray ionization). Atorvastatin was purchased from Sequoia Reseach Products. The syntheses of Deltarasine, 1L* and Deltazinone 1 were previously reported (G. Zimmermann, B. Papke, S. Ismail, N. Vartak, A. Chandra, M. Hoffmann, S. A. Hahn, G. Triola, A. Wittinghofer, P. I. H. Bastiaens, et al., *Nature* 2013, 497, 638-42; B. Papke, S. Murarka, H. A. Vogel, P. Martín-Gago, M. Kovacevic, D. C. Truxius, E. K. Fansa, S. Ismail, G. Zimmermann, K. Heinelt, et al., *Nat. Commun.* 2016, 7, 11360.). 2L* and 8L* were obtained by direct coupling of the linked fluorescein to the correspondent precursor (D. Arosio, L. Manzoni, E. M. V. Araldi, C. Scolastico, *Bioconjug. Chem.* 2011, 22, 664-672.). All other chemicals and solvents were purchased from Sigma-Aldrich, Fluka, TCI, Acros Organics, ABCR and Alfa Aesar. Unless otherwise noted, all commercially available compounds were used as received without further purifications.

General Synthetic Routes:

The disulfonamides of the formula (I) can be prepared starting from the correspondent sulfonyl chlorides. First, commercially available 4-bromobenzenesulfonyl chloride (6*) is converted into sulfonamide 5* by direct reaction with the amine 7*. This bromobenzene is converted into the sulfonylchloride 3* in a two-step strategy. Finally, 3* is transformed into benzene disulfonamide (I) by direct reaction with the amine 2* as shown in Schemes 1 and 2.

General Reductive Amination Procedures:

Reductive amination procedure I: To a solution of the aldehyde (1.0 eq) and MgSO$_4$ (4 eq, anh) in MeOH (1 mL/mmol) was added the amine (1.0 mmol). After stirring at room temperature for 12 h, the solution was cooled down to 0° C. and sodium borohydride (0.5 eq) was added portion wise. The resulting solution was stirred at room temperature for 1 h. After addition of water, methanol was removed under reduced pressure and the resulting aqueous phase was extracted with DCM. The combined extracts were washed with brine, dried over MgSO$_4$, filtered and concentrated in vacuo to give corresponding compounds. Unless otherwise specified, the secondary amines were used in the next reaction without further purification. (see scheme 3).

Reductive amination procedure II: A mixture of the aldehyde (1.0 eq), the amine (1.0 eq), sodium triacetoxyborohydride (2.0 eq), and acetic acid (2.0 eq) in 1,2-dichloroethane was stirred at room temperature overnight, diluted with CH$_2$Cl$_2$, washed with water, dried over MgSO$_4$, filtered and concentrated in vacuo to give corresponding compounds. Unless otherwise specified, the secondary amines were used in the next reaction without further purification.

Example A-01. Preparation of N-(4-chlorobenzyl)cyclopentanamine, 8*

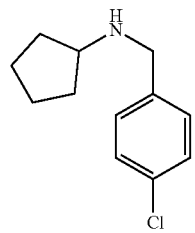 [SMILES: Clc1ccc(CNC2CCCC2)cc1]

The title compound (11.7 g, 93% yield) was prepared according to the KY reductive amination procedure I by using 4-chlorobenzaldehyde (10.0 g, 71.4 mmol), cyclopentylamine (7.5 mL, 71.4 mmol), MgSO$_4$ (26.20 g, 214 mmol) and NaBH$_4$ (1.35 g, 37.7 mmol. $^1$H NMR (400 MHz, CDCl$_3$) δ 7.26 (m, 4H, 4 CH, Ar), 3.72 (s, 2H, CH2-ArCl), 3.08 (q, J=7 Hz, 1H, CH, Cp), 1.83 (m, 2H), 1.69 (m, 2H), 1.53 (m, 2H), 1.34 (m, 2H). $^{13}$C NMR (101 MHz, CDCl$_3$) δ 139.4 (C), 132.6 (C), 129.6 (2 CH, Ar), 128.6 (2 CH, Ar), 59.3 (CH, Cp), 52.1 (CH2-ArCl), 33.3 (2 CH2), 24.2 (2 CH2). HRMS: calc. for [M+H]$^+$ C12H17ClN: 210.0971, found: 210.1044.

Example A-02. Preparation of 4-bromo-N-(4-chlorobenzyl)-N-cyclopentylbenzenesulfonamide, 9*

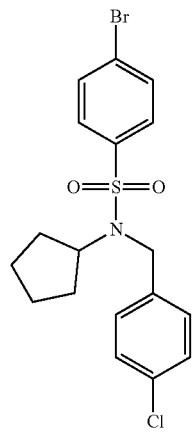 [SMILES: O=S(=O)(c1ccc(Br)cc1)N(Cc1ccc(Cl)cc1)C1CCCC1]

A solution of 4-bromobenzenesulfonyl chloride (3.5 g, 13.7 mmol) and N-(4-chlorobenzyl)cyclopentanamine (2.87 g, 13.7 mmol) in dichloromethane (18 mL/mmol) was treated with triethylamine (2.7 mL, 20.6 mmol) and stirred at room temperature for 5 h. Water was then added to the mixture and the solution was extracted with dichloromethane. The combined organic phases were washed with brine dried over magnesium sulfate, filtered and concentrated under vacuum. The crude product was purified by flash column chromatography on silica gel using 20% ethylacetate/cyclohexane as an eluent to provide analytically pure product (4.49 g, 76% yield). $^1$H NMR (400 MHz, cdcl$_3$) δ 7.64 (m, 4H, 4 CH, Ar), 7.30 (m, 4H, 4 CH, Ar), 4.31 (s, 2H, CH2-ArCl), 4.25 (dd, J=17, 9 Hz, 1H, CH, Cp), 1.61 (m, 2H), 1.51 (m, 2H), 1.42 (m, 2H), 1.25 (m, 2H). $^{13}$C NMR (101 MHz, cdcl$_3$) δ 139.8 (C), 137.4 (C), 133.2 (C), 132.5 (2 CH, Ar), 128.8 (2 CH, Ar), 128.8 (2 CH, Ar), 128.6 (2 CH, Ar), 127.6 (C), 59.7 (CH, Cp), 47.0 (CH2-ArCl), 29.5 (2 CH2), 23.5 (2 CH2). HRMS: calc. for [M+H]$^+$ C18H20BrClNO2S: 428.0008, found: 428.0081.

Example A-03. Preparation of 4-(Benzylthio)-N-(4-chlorobenzyl)-N-cyclopentylbenzenesulfonamide, 10*

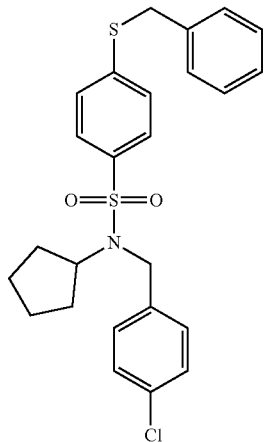 [SMILES: O=S(=O)(c1ccc(SCc2ccccc2)cc1)N(Cc1ccc(Cl)cc1)C1CCCC1]

To a round-bottom-flask were added 4-bromo-N-(4-chlorobenzyl)-N-cyclopentylbenzenesulfonamide (3.80 g, 8.9 mmol, 1 eq), i-Pr$_2$NEt (3.1 mL, 17.7 mmol, 2 eq) and dry 1,4-dioxane. The mixture was evacuated and backfilled with nitrogen (3 cycles). Catalyst Pd$_2$(dba)$_3$ (201 mg, 0.2 mmol, 0.025 eq), Xantphos (256 mg, 0.4 mmol, 0.05 eq) and the benzylthiol (1.04 mL, 8.9 mmol, 1 ea) were added and then the mixture was degassed twice more. The mixture was heated to reflux overnight. The reaction mixture was then allowed to reach ambient temperature, filtered and concentrated. The crude product was purified by flash column chromatography on silica gel using 20% ethylacetate/cyclohexane as an eluent to provide analytically pure product 19 (3.35 g, 80% yield) as a yellowish solid. $^1$H NMR (400 MHz, CDCl$_3$) δ 7.58 (m, 2H, 2 CH Ar), 7.32-7.13 (m, 11H, 11 CH Ar), 4.22 (s, 2H, CH2-ArCl), 4.17 (m, 1H, CH Cp), 4.13 (s, 2H, CH2-Ph), 1.50 (m, 2H), 1.41 (m, 2H), 1.33 (m, 2H), 1.15 (m, 2H). $^{13}$C NMR (101 MHz, CDCl$_3$) δ 143.8 (C), 137.7 (C), 137.6 (C), 136.2 (C), 133.2 (C), 129.0 (2 CH Ar), 128.9 (3 CH Ar), 128.8 (2 CH Ar), 128.6 (2 CH Ar), 127.9 (2CH Ar), 127.8 (CH Ar), 127.7 (CH Ar), 59.7 (CH, Cp), 47.1 (CH2-ArCl), 37.7 (CH2-Ph), 29.5 (2 CH2, Cp), 23.6 (2 CH2, Cp). HRMS: calc. for [M+Na]$^+$ C25H26ClNNaO2S2: 494.0991, found: 494.0986.

Example A-04. Preparation of 4-(N-(4-Chlorobenzyl)-N-cyclopentylsulfamoyl)benzenesulfonyl Chloride, 11*

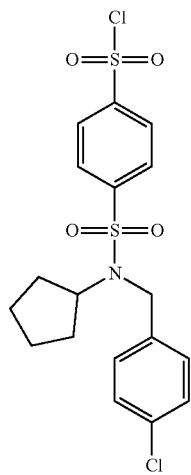 [SMILES: O=S(=O)(Cl)c1ccc(S(=O)(=O)N(Cc2ccc(Cl)cc2)C2CCCC2)cc1]

To an ice-cold solution of 4-(benzylthio)-N-(4-chlorobenzyl)-N-cyclopentylbenzenesulfonamide (1.80 g, 3.8 mmol, 1 eq) in CH$_3$CN—HOAc—H$_2$O (41 mL-2.5 mL-1.6 mL) was added portionwise 2,4-dichloro-5,5-dimethylhydantoin (1.50 g, 7.6 mmol, 2 eq). The reaction mixture was stirred at 0-5° C. for 2 hours, and concentrated to near dryness under vacuum. The crude product was diluted with CH$_2$Cl$_2$ (70 mL), and the solution cooled down to ~0° C. 5% NaHCO$_3$ aqueous solution (80 mL) was added slowly at <10° C. The mixture was stirred at 0-5° C. for 15 min, and the lower organic washed once more with 10% brine solution at <10° C. The lower organic was dried over MgSO$_4$, and filtered and concentrated to afford the product (1.64 g, 96% yield) as a white solid, which was used in the next reaction without further purification. $^1$H NMR (400 MHz, cdcl$_3$) δ 8.13 (d, J=9 Hz, 2H, 2 CH, Ar), 7.99 (d, J=9 Hz, 2H, 2 CH, Ar), 7.28 (s, 4H, 4 CH, Ar), 4.37 (s, 1H, CH2-ArCl), 4.31 (dd, J=18 Hz, 1H, CH, Cp), 1.67 (s, 2H), 1.55 (m, 2H), 1.43 (m, 2H), 1.32 (s, 2H). $^{13}$C NMR (101 MHz, cdcl$_3$) δ 147.4 (C), 147.1 (C), 136.4 (C), 133.6 (C), 128.9 (2 CH, Ar), 128.8 (2 CH, Ar), 128.5 (2 CH, Ar), 127.9 (2 CH, Ar), 60.1 (CH, Cp), 47.3 (CH2-ArCl), 29.7 (2 CH2), 23.4 (2 CH2). LC-MS (ESI): calc. for [M+H]+C18H20Cl2NO4S2: 448.01, found: 448.32.

Example A-05. Preparation of tert-Butyl 4-((benzylamino)methyl)piperidine-1-carboxylat 12*

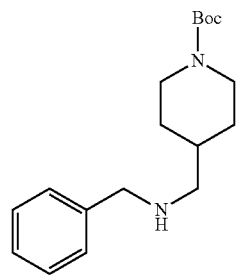 [SMILES: CC(C)(C)OC(=O)N1CCC(CNCc2ccccc2)CC1]

The title compound (2.63 g, 92% yield) was prepared according to the reductive amination procedure I by using benzaldehyde (1.00 g, 9.4 mmol), tert-butyl 4-(aminomethyl)piperidine-1-carboxylate (2.02 g, 9.4 mmol), MgSO$_4$ (3.46 g, 28.2 mmol) and NaBH$_4$ (178 mg, 4.7 mmol). $^1$H NMR (400 MHz, CDCl$_3$) δ 7.32 (m, 5H, 5 CH, Ar), 7.24 (m, 1H, CH, Ar), 4.08 (s, 2H), 3.78 (s, 2H, CH2-Ph), 2.68 (t, J=12 Hz, 2H), 2.50 (d, J=7 Hz, 2H, CH2-piperidine), 1.69 (t, J=13 Hz, 2H), 1.61 (m, 1H), 1.45 (s, 9H), 1.10 (ddd, J=24, 12, 4 Hz, 2H). $^{13}$C NMR (101 MHz, CDCl$_3$) δ 155.8 (CO), 140.4 (C), 128.6 (2 CH, Ar), 128.3 (2 CH, Ar), 127.2 (CH, Ar), 79.5 (C, Boc), 55.2 (CH2-piperidine), 54.2 (CH2-Ph), 44.0 (2 CH2), 36.7 (CH), 30.6 (2 CH2), 28.7 (3 CH3). HRMS: calc. for [M+H]+C18H29N2O2: 305.2151, found: 305.2193.

Example A-06. Preparation of N1-Benzyl-N4-(4-chlorobenzyl)-N4-cyclopentyl-N1-(piperidin-4-ylmethyl)benzene-1,4-disulfonamide, 44

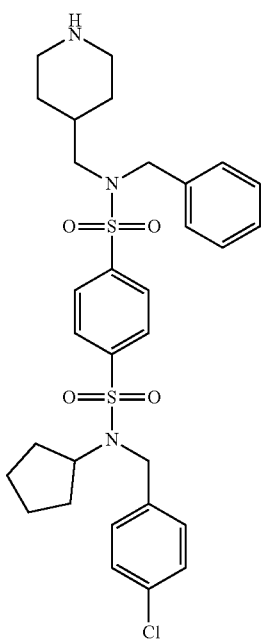 [SMILES: O=S(=O)(c1ccc(S(=O)(=O)N(Cc2ccc(Cl)cc2)C2CCCC2)cc1)N(Cc1ccccc1)CC1CCNCC1]

A solution of 4-(N-(4-chlorobenzyl)-N-cyclopentylsulfamoyl)benzenesulfonyl chloride (50 mg, 0.1 mmol) and tert-butyl 4-((benzylamino)methyl)piperidine-1-carboxylate (34 mg, 0.1 mmol) in dichloromethane (25 mL/mmol) was treated with triethylamine (23 uL, 0.2 mmol) and stirred at 0° C. for 30 min. Water was then added and the product was extracted into DCM. The combined extracts were dried over MgSO$_4$ and filtered. The solvent was reduced and Boc deprotection was then done in situ by slowly adding to the mixture TFA (10 eq), and this reaction was then stirred for 2 h at room temperature. The solvent was evaporated and purification of the resulting mixture was carried out on preparative HPLC using a reversed-phase C18 column (RP C18, flow 20.0 mL/min, solvent A: 0.1% TFA in water, solvent B: 0.1% TFA in acetonitrile, from 10% B to 100% B). Acetonitrile was removed and the remaining water was freeze dried to afford the pure product (56 mg, 70% yield) as a white solid (TFA salt).

$^1$H NMR (400 MHz, dmso) δ 8.06 (m, 4H, 4 CH Ar), 7.41 (m, 4H, 4 CH Ar), 7.29 (m, 5H, 5 CH Ar), 4.41 (s, 2H, CH2-Ar), 4.37 (s, 2H, CH2-Ar), 4.27 (m, 1H, CH Cp), 3.19 (d, J=13 Hz, 2H), 3.05 (d, J=7 Hz, 2H, CH2-piperidine), 2.63 (t, J=11 Hz, 2H), 1.70 (m, 3H, including CH piperidine), 1.58 (m, 4H), 1.48-1.34 (m, 2H), 1.14 (m, 4H). $^{13}$C NMR (126 MHz, DMSO) δ 144.0 (C), 143.2 (C), 138.9 (C), 136.7 (C), 132.0 (C), 129.1 (2 CH, Ar), 128.9 (2 CH, Ar), 128.8 (2 CH, Ar), 128.7 (2 CH, Ar), 128.7 (CH, Ar), 128.6 (CH, Ar), 128.3 (CH, Ar), 59.6 (CH, Cp), 53.7 (CH2), 52.4 (CH2), 46.6 (2 CH2), 43.2 (2 CH2), 32.4 (CH, piperidine), 29.0 (2 CH2), 26.6 (CH2), 23.4 (2 CH2). HRMS (ESI): calc. for [M+H]$^+$ C31H39ClN3O4S2: 616.2077, found: 616.2065.

Example A-07. Preparation of tert-butyl 4-(((4-(N-(4-chlorobenzyl)-N-cyclopentylsulfamoyl)phenyl)sulfonamido)methyl)piperidine-1-carboxylate, 13*

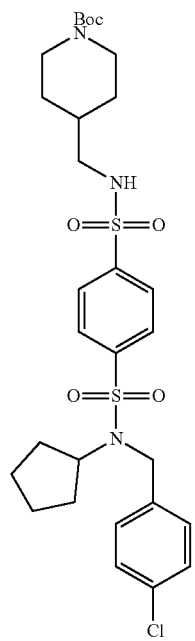 [SMILES: CC(C)(C)OC(=O)N1CCC(CNS(=O)(=O)c2ccc(S(=O)(=O)N(Cc3ccc(Cl)cc3)C3CCCC3)cc2)CC1]

A solution of 4-(N-(4-chlorobenzyl)-N-cyclopentylsulfamoyl)benzenesulfonyl chloride (6 g, 13.4 mmol) and tert-butyl 4-(aminomethyl)piperidine-1-carboxylate (3.2 g, 14.7 mmol) in dichloromethane (25 mL/mmol) was treated with triethylamine (2.3 mL, 21.0 mmol) and stirred at 0° C. for 30 min. Water was then added and the product was extracted into DCM. The combined extracts were dried over MgSO$_4$ and filtered. The solvent was concentrated under vacuum. The crude product was purified by flash column chromatography on silica gel using 30% ethylacetate/cyclohexane as an eluent to provide analytically pure product (7.6 g, 91% yield) as a white solid.

$^1$H NMR (600 MHz, CDCl$_3$) δ 7.87 (dd, J=21, 9 Hz, 4H, Ar), 7.23 (s, 4H, Ar), 4.84 (s, 1H, NH), 4.28 (s, 2H, CH2), 4.22 (p, J=9 Hz, 1H, Cp), 4.02 (d, J=13 Hz, 2H), 2.79 (s, 2H), 2.57 (dd, J=19, 7 Hz, 2H), 1.98 (m, 1H, Cy), 1.55 (m, 4H), 1.46 (m, 2H), 1.38 (m, 2H), 1.37 (s, 9H, Boc), 1.20 (m, 2H), (qd, J=12, 4 Hz, 2H). $^{13}$C NMR (151 MHz, CDCl$_3$) δ 154.9 (CO, Boc), 144.8 (C, Ar), 144.1 (C, Ar), 136.9 (C, Ar), 133.4 (C, Ar), 128.8 (2 CH, Ar), 128.6 (2 CH, Ar), 128.1 (2 CH, Ar), 127.9 (2 CH, Ar), 79.7 (C, Boc), 59.9 (CH, Cp), 48.8 (CH2), 47.1 (2 CH2), 43.5 (2 CH2), 36.7 (CH, Cy), 29.6 (2 CH2), 29.5 (2 CH2), 28.6 (3 CH3), 23.4 (CH2). HRMS: calc. for [M+H]$^+$ C29H41 ClN3O6S2: 626.2047, found: 626.2090.

Example A-08. Preparation of tert-butyl ((trans)-4-((4-(N-(4-chlorobenzyl)-N-cyclopentylsulfamoyl)phenyl)sulfonamido)cyclohexyl)carbamate, 14*

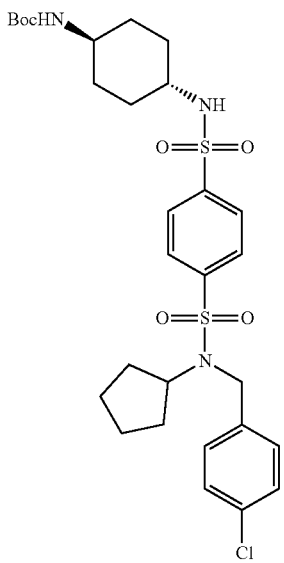 [SMILES: CC(C)(C)OC(=O)N[C@H]1CC[C@H](NS(=O)(=O)c2ccc(S(=O)(=O)N(Cc3ccc(Cl)cc3)C3CCCC3)cc2)CC1]

A solution of 4-(N-(4-chlorobenzyl)-N-cyclopentylsulfamoyl)benzenesulfonyl chloride (0.5 g, 1.1 mmol) and tert-butyl ((trans)-4-aminocyclohexyl)carbamate (0.26 g, 1.2 mmol) in dichloromethane (25 mL/mmol) was treated with triethylamine (0.18 mL, 1.3 mmol) and stirred at 0° C. for 30 min. Water was then added and the product was extracted into DCM. The combined extracts were dried over MgSO₄ and filtered. The solvent was concentrated under vacuum. The crude product was purified by flash column chromatography on silica gel using 30% ethylacetate/cyclohexane as an eluent to provide analytically pure product (0.31 g, 88% yield) as a white solid.

$^1$H NMR (500 MHz, CDCl₃) δ 7.88 (dd, J=35, 8 Hz, 4H, 4 CH, Ar), 7.26 (m, 2H, 2 CH, Ar), 7.21 (m, 2H, 2 CH, Ar), 5.20 (d, J=7 Hz, 1H, NH), 4.35 (m, 2H), 4.27 (s, 2H, CH2-Ar), 4.21 (m, 1H, Cp), 3.25 (bs, 1H, CH), 3.05 (m, 1H, CH), 1.87 (m, 2H), 1.74 (m, 2H), 1.58-1.47 (m, 2H), 1.49-1.38 (m, 2H), 1.35 (s, 9H, 3 CH3), 1.27-1.11 (m, 4H), 1.03 (m, 2H). $^{13}$C NMR (101 MHz, cdcl₃) δ 155.3 (CO), 145.6 (C, Ar), 144.6 (C, Ar), 137.1 (C, Ar), 133.5 (C, Ar), 128.9 (2 CH, Ar), 128.7 (2 CH, Ar), 128.1 (2 CH, Ar), 127.8 (2 CH, Ar), 79.7 (C, Boc), 59.93 (CH, Cp), 52.6 (CH), 48.7 (CH), 47.3 (CH2-Ar), 44.0 (CH2), 32.8 (2 CH2), 32.1 (2 CH2), 29.6 (2 CH2), 28.6 (3 CH3), 23.5 (CH2). HRMS: calc. for [M+H]⁺ C29H41ClN3O6S2: 626.2047, found: 626.2010.

Example A-09. Preparation of (2-(methylamino)pyrimidin-4-yl)methanol, 15*

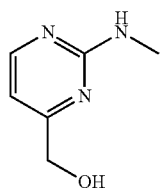

To a solution of 2-(methylamino)pyrimidine-4-carbaldehyde (100 mg, 0.73 mmol) in MeOH (1 mL/mmol) at 0° C. sodium borohydride (1 eq) was added portion wise. The resulting solution was stirred for 1 h. After addition of water, methanol was removed under reduced pressure and the resulting aqueous phase was extracted with DCM. The combined extracts were washed with brine, dried over MgSO₄, filtered and concentrated in vacuo to give (2-(methylamino)pyrimidin-4-yl)methanol (quantitative) as a brown oil, which was used in the next reactions without further purification.

$^1$H NMR (400 MHz, cdcl₃) δ 8.14 (d, J=4 Hz, 1H, CH, Ar), 6.43 (d, J=4 Hz, 1H, CH, Ar), 5.52 (bs, 1H, NH), 4.49 (s, 2H, CH2), 2.92 (d, J=5 Hz, 3H, CH3). $^{13}$C NMR (101 MHz, cdcl₃) δ 169.2 (C, Ar), 162.4 (C, Ar), 158.0 (CH, Ar), 106.5 (CH, Ar), 63.5 (CH2), 28.5 (CH3). HRMS: calc. for [M+H]⁺ C6H10N3O: 140.0746, found: 140.0741.

Example A-10. Preparation of 4-(bromomethyl)-N-methylpyrimidin-2-amine, 16*

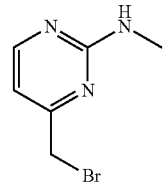

To a solution of (2-(methylamino)pyrimidin-4-yl)methanol (300 mg, 2.16 mmol) in DCM (6 mL/mmol) at 0° C., N-Bromosuccinimide (403 mg, 2.26 mmol) and triphenylphosphine (678 mg, 2.6 mmol) were added. The resulting solution was stirred for 2 h at 0° C. and then diluted with DCM. The mixture was washed with saturated NaHCO₃ followed by brine and the organic phase was dried (MgSO₄), filtered and concentrated. The crude was purified by flash column chromatography over silica gel, eluting with cyclohexane to EtOAc (2:1) to give 274 mg (63%) of the title compound as a brown solid.

$^1$H NMR (400 MHz, cdcl₃) δ 8.28 (d, J=5 Hz, 1H, CH, Ar), 6.64 (d, J=5 Hz, 1H, CH, Ar), 5.26 (s, 1H, NH), 4.23 (s, 2H, CH2), 3.00 (d, J=5 Hz, 3H, CH3). $^{13}$C NMR (101 MHz, cdcl₃) δ 165.8 (C, Ar), 163.1 (C, Ar), 159.1 (CH, Ar), 109.2 (CH, Ar), 32.5 (CH2), 28.6 (CH3). HRMS (ESI): calc. for [M+H]⁺ C6H9BrN3: 201.9902, found: 201.9884.

Example A-11. Preparation of N1-(4-Chlorobenzyl)-N1-cyclopentyl-N4-((2-(methylamino)pyrimidin-4-yl)methyl)-N4-(piperidin-4-ylmethyl)benzene-1,4-disulfonamide, 16

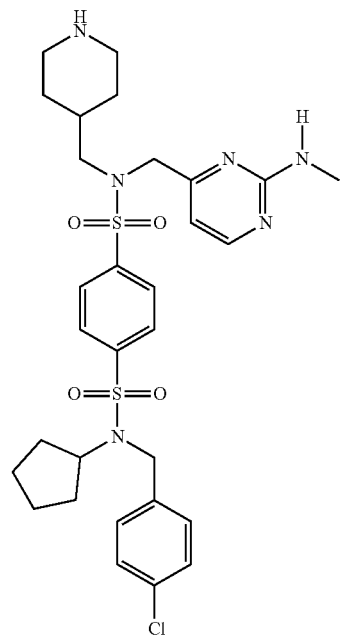 [SMILES: CNc1nccc(CN(CC2CCNCC2)S(=O)(=O)c2ccc(S(=O)(=O)N(Cc3ccc(Cl)cc3)C3CCCC3)cc2)n1]

A solution of 4-(N-(4-chlorobenzyl)-N-cyclopentylsulfamoyl)-benzenesulfonyl chloride (50 mg, 0.1 mmol) and tert-butyl 4-((((2-(methylamino)pyrimidin-4-yl)methyl)amino)methyl)piperidine-1-carboxylate (37 mg, 0.1 mmol) in dichloromethane (25 mL/mmol) was treated with triethylamine (23 uL, 0.2 mmol) and stirred at 0° C. for 30 min. Water was then added and the product was extracted into DCM. The combined extracts were dried over MgSO$_4$ and filtered. The solvent was reduced and Boc deprotection was then done in situ by slowly adding to the mixture TFA (~10 eq), and this reaction was then stirred for 2 h at room temperature. The solvent was evaporated and purification of the resulting mixture was carried out on preparative HPLC using a reversed-phase C18 column (RP C18, flow 20.0 mL/min, solvent A: 0.1% TFA in water, solvent B: 0.1% TFA in acetonitrile, from 10% B to 100% B). The solvent was freeze dried to afford the pure product (73 mg, 87% yield) as a white solid (TFA salt).

$^1$H NMR (500 MHz, DMSO) δ 8.18 (s, 1H, CH, Ar), 8.06 (s, 4H, 4 CH, Ar), 7.41 (m, 4H, 4 CH, Ar), 6.50 (d, J=5 Hz, 1H, CH, Ar), 4.38 (s, 2H, CH2), 4.31 (m, 2H, CH2), 4.27 (m, 1H, CH, Cp), 3.27 (m, 4H, 2 CH2), 2.74 (m, 5H, CH2 plus CH3), 1.90-1.75 (m, 3H, CH2 plus CH piperidine), 1.46 (s, 4H, 2 CH2), 1.35 (m, 2H, CH2), 1.36 (m, 2H, CH2), 1.14 (m, 2H, CH2). $^{13}$C NMR (126 MHz, DMSO) δ 166.2 (C, Ar), 162.3 (C, Ar), 158.1 (CH, Ar, pyrimidine), 143.9 (C, Ar), 143.1 (C, Ar), 138.9 (C, Ar), 132.0 (C, Ar), 129.1 (2 CH, Ar), 128.7 (2 CH, Ar), 128.7 (2 CH, Ar), 128.6 (2 CH, Ar), 107.8 (CH, Ar, pyrimidine), 59.6 (CH, Cp), 52.7 (CH2), 46.5 (CH2), 43.2 (3 CH2), 32.1 (CH, piperidine), 29.0 (CH2), 28.2 (CH3), 26.5 (2 CH2), 23.3 (3 CH2). HRMS (ESI): calc. for [M+H]$^+$ C30H40ClN6O4S2: 647.2163, found: 647.2120.

Example A-12. Preparation of N1-((trans)-4-aminocyclohexyl)-N4-(4-chlorobenzyl)-N4-cyclopentyl-N1-((2-(methylamino)pyrimidin-4-yl)methyl)benzene-1,4-disulfonamide, 19

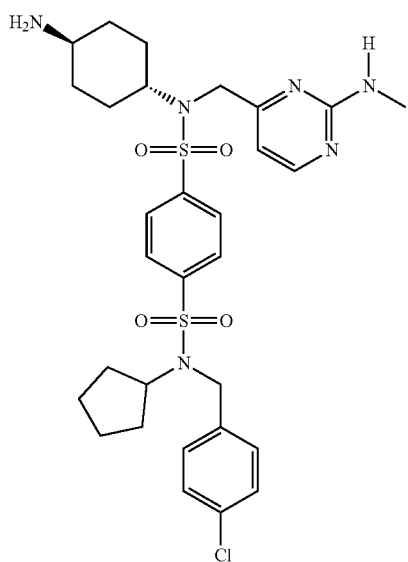 [SMILES: CNc1nccc(CN([C@H]2CC[C@H](N)CC2)S(=O)(=O)c2ccc(S(=O)(=O)N(Cc3ccc(Cl)cc3)C3CCCC3)cc2)n1]

A solution of 4-(N-(4-chlorobenzyl)-N-cyclopentylsulfamoyl)-benzenesulfonyl chloride (100 mg, 0.2 mmol) and tert-butyl (4-(((2-(methylamino)pyrimidin-4-yl)methyl)amino)cyclohexyl)-carbamate (75 mg, 0. mmol) in dichloromethane (25 mL/mmol) was treated with triethylamine (46 uL, 0.4 mmol) and stirred at room temperature for 5 h. Water was then added and the product was extracted into DCM. The combined extracts were dried over MgSO$_4$ and filtered. The solvent was reduced and Boc deprotection was then done in situ by slowly adding to the mixture TFA (10 eq), and this reaction was then stirred for 2 h at room temperature. The solvent was evaporated and purification of the resulting mixture was carried out on preparative HPLC using a reversed-phase C18 column (RP C18, flow 20.0 mL/min, solvent A: 0.1% TFA in water, solvent B: 0.1% TFA in acetonitrile, from 10% B to 100% B). The solvent was freeze dried to afford the pure product (140 mg, 84% yield) as a white solid (TFA salt).

$^1$H NMR (500 MHz, DMSO) δ 8.30 (d, J=5 Hz, 1H, CH Ar), 8.10 (m, 4H, 4 CH, Ar), 7.85 (m, 2H, NH$_2$), 7.42 (m, 4H, 4 CH, Ar), 6.71 (d, J=5 Hz, 1H, CH Ar), 4.41 (m, 4H, 2 CH2-Ar), 4.26 (m, 1H, Ch, Cp), 3.71 (ddd, J=15, 11, 5 Hz, 1H, CH, Cy), 2.86 (m, 1H, CH, Cy), 2.84 (s, 3H, CH3), 1.83 (m, 2H), 1.42 (m, 8H), 1.33 (m, 4H), 1.12 (m, 2H). $^{13}$C NMR (126 MHz, DMSO) δ 170.5 (C, Ar), 160.9 (C, Ar), 156.4 (CH, Ar, pyrimidine), 144.4 (C, Ar), 144.1 (C, Ar), 139.0 (C, Ar), 132.0 (C, Ar), 129.0 (2 CH, Ar), 128.7 (4 CH, Ar), 128.6 (2 CH, Ar), 107.2 (CH, Ar, pyrimidine), 59.5 (CH, Cp), 56.7 (CH, Cy), 48.5 (CH2), 48.1 (CH, Cp), 46.6 (CH2), 29.7 (CH2 plus CH, Cy), 28.9 (2 CH2), 28.3 (CH3), 28.0 (CH2), 23.4 (4 CH2). HRMS (ESI): calc. for [M+H]$^+$ C30H40ClN6O4S2: 647.2163, found: 647.2235.

Example A-13. Preparation of tert-Butyl 4-cyano-2-(methylamino)benzoate, 17*

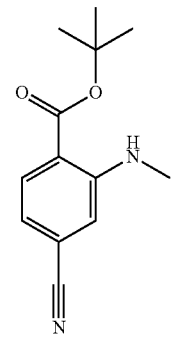 [SMILES: CNc1cc(C#N)ccc1C(=O)OC(C)(C)C]

To a solution of tert-Butyl 4-cyano-2-fluorobenzoate[12] (2.5 g, 11.3 mmol) in DMF, K$_2$CO$_3$ (4 eq) was added. Then, methyl amine N hydrochloride (1.5 eq) was added and the mixture was stirred overnight at 100° C. The reaction mixture was quenched with water and extracted with ethyl acetate. The organic layer was separated, dried and the solvent removed under vacuum. The mixture was purified by column chromatography (9:1 cyclohexane/AcOEt) concentrated to afford 2.0 g (78% yield) of the desired product.

$^1$H NMR (400 MHz, cdcl$_3$) δ 7.88 (dd, J=8, 1 Hz, 1H, CH, Ar), 6.87 (d, J=1 Hz, 1H, CH, Ar), 6.79 (dd, J=8, 1 Hz, 1H, CH, Ar), 2.90 (s, 3H, CH3), 1.57 (s, 9H, 3 CH3). $^{13}$C NMR (101 MHz, cdcl$_3$) (167.2 (CO), 151.6 (C), 132.6 (CH), 119.0 (C), 117.1 (CH), 116.8 (C), 115.0 (CH), 114.3 (C), 82.0 (C, tBu), 29.6 (CH3), 28.4 (3 CH3). HRMS (ESI): calc. for [M+H]+C13H17N2O2: 233.1212, found: 233.1293.

Example A-14. Preparation of tert-Butyl 4-formyl-2-(methylamino)benzoate, 18*

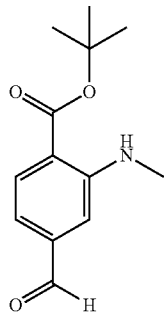 [SMILES: CNc1cc(C=O)ccc1C(=O)OC(C)(C)C]

DIBAL-H (1 M solution in toluene, 1.2 eq) was added dropwise at −40° C. to a solution of tert-butyl 4-cyano-2-(methylamino)benzoate (0.5 g, 2.15 mmol) in CH$_2$Cl$_2$ (4 mL/mmol), and stirred for 3 h. The reaction mixture was then quenched with MeOH (0.1 mL) and Rochelle's solution (4 mL). The mixture was warmed to ambient temperature, stirred for 1 h and diluted with CH$_2$Cl$_2$. The organic layer was separated, then washed with brine, dried over MgSO4, filtered and concentrated in vacuo. The mixture was used in the next step without further purification (2:1 mixture RP:SM).

$^1$H NMR (400 MHz, cdcl$_3$) δ 9.98 (s, 1H, CHO), 7.98 (d, J=8 Hz, 1H, CH, Ar), 7.11 (d, J=1 Hz, 1H, CH, Ar), 7.04 (dd, J=8, 1 Hz, 1H, CH, Ar), 2.96 (s, 3H, CH3), 1.60 (m, 9H, 3 CH3). $^{13}$C NMR (101 MHz, cdcl$_3$) δ 192.9 (C, CHO), 167.7 (CO), 152.1 (C), 140.2 (C), 132.7 (CH), 116.8 (C), 114.9 (CH), 111.5 (CH), 81.7 (C, tBu), 29.8 (CH3), 28.4 (3 CH3). HRMS (ESI): calc. for [M+H]+C13H18NO3: 236.1208, found: 236.1281.

Example A-15. Preparation of tert-Butyl 4-(((4-(tert-butoxycarbonyl)-3-methylamino)benzyl)amino)methyl)piperidine-1-carboxylate, 19*

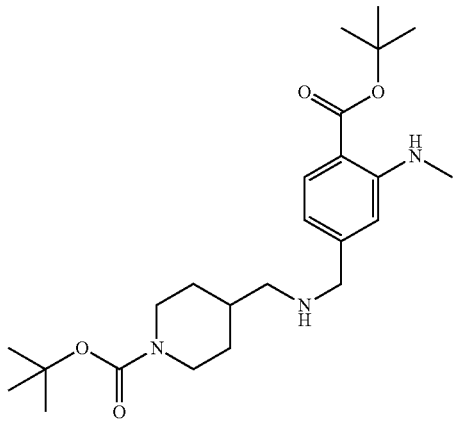 [SMILES: CNc1cc(CNCC2CCN(C(=O)OC(C)(C)C)CC2)ccc1C(=O)OC(C)(C)C]

The title compound (163 mg, 84% yield) was prepared according to the reductive amination procedure II by using tert-butyl 4-formyl-2-(methylamino)benzoate (140 mg, 0.45 mmol), tert-butyl 4-(aminomethyl)piperidine-1-carboxylate (96 mg, 0.45 mmol), sodium triacetoxyborohydride (189 mg, 0.89 mmol), and acetic acid (54 μL, 0.89 mmol).

$^1$H NMR (400 MHz, cdcl$_3$) δ 7.78 (d, J=8 Hz, 1H, CH, Ar), 6.58 (s, 1H, CH, Ar), 6.50 (d, J=8 Hz, 1H, CH, Ar), 4.04 (d, J=12 Hz, 2H), 3.85 (s, 2H, CH2-Ar), 2.85 (s, 3H, CH3), 2.73 (bs, 2H, CH2-piperidine), 2.63 (t, J=13 Hz, 2H), 1.84 (s, 1H, CH), 1.70 (d, J=13 Hz, 2H), 1.50 (s, 9H, 3 CH3), 1.42 (s, 9H, 3 CH3), 1.08 (dt, J=12, 8 Hz, 2H). $^{13}$C NMR (101 MHz, cdcl$_3$) δ 167.7 (CO), 155.0 (CO), 152.2 (C), 136.0 (C), 133.0 (CH), 115.3 (CH), 112.8 (C) 110.0 (CH), 81.4 (C, tBu), 80.4 (C, tBu), 52.1 (CH2), 51.9 (CH2), 43.3 (2 CH2), 33.8 (CH), 29.6 (2 CH2), 29.5 (CH3), 28.5 (3 CH3), 28.4 (3 CH3). HRMS (ESI): calc. for [M+H]+ C24H40N3O4: 434.2941, found: 434.3013.

Example A-16. Preparation of 4-(((4-(N-(4-chlorobenzyl)-N-cyclopentylsulfamoyl)-N-(piperidin-4-ylmethyl)phenyl)sulfonamido)methyl)-2-(methylamino)benzoic Acid, 21

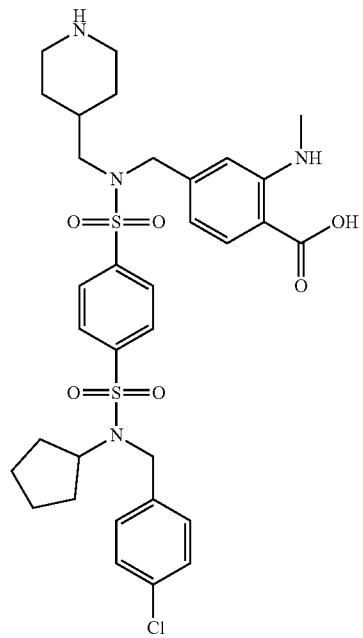 [SMILES: CNc1cc(CN(CC2CCNCC2)S(=O)(=O)c2ccc(S(=O)(=O)N(Cc3ccc(Cl)cc3)C3CCCC3)cc2)ccc1C(=O)O]

A solution of 4-(N-(4-chlorobenzyl)-N-cyclopentylsulfamoyl)benzenesulfonyl chloride (180 mg, 0.40 mmol) and tert-butyl 4-(((4-(tert-butoxycarbonyl)-3-(methylamino)benzyl)amino)methyl)piperidine-1-carboxylate (191 mg, 0.44 mmol) in dichloromethane (25 mL/mmol) was treated with triethylamine (83 uL, 0.60 mmol) and stirred at 0° C. for 30 min. Water was then added and the product was extracted into DCM. The combined extracts were dried over MgSO$_4$ and filtered. The solvent was reduced and Boc deprotection was then done in situ by slowly adding to the mixture TFA (~10 eq), and this reaction was then stirred for 2 h at room temperature. The solvent was evaporated and purification of the resulting mixture was carried out on preparative HPLC using a reversed-phase C18 column (RP C18, flow 20.0 mL/min, solvent A: 0.1% TFA in water, solvent B: 0.1% TFA in acetonitrile, from 10% B to 100% B). The solvent was freeze dried to afford the pure product (127 mg, 33% yield) as a white solid (TFA salt).

$^1$H NMR (400 MHz, CD$_3$OD) δ 8.08-7.91 (m, 4H, 4CH, Ar), 7.90 (d, J=5 Hz, 1H, CH Ar), 7.33 (dd, J=26, 9 Hz, 4H, 4CH, Ar), 6.81 (d, J=2 Hz, 1H, CH, Ar), 6.62 (dd, J=8, 2 Hz, 1H, CH, Ar), 4.41 (s, 2H, CH2-Ar), 4.31 (m, 1H, Cp), 4.13 (s, 2H, CH2-Ar), 3.81 (d, J=12 Hz, 2H), 2.94 (d, J=7 Hz, 2H), 2.89 (s, 3H, CH3), 2.34 (t, J=11 Hz, 2H), 1.87 (d, J=13 Hz, 2H), 1.75 (m, 1H, piperidine), 1.63-1.55 (m, 2H), 1.54-1.47 (m, 2H), 1.46-1.38 (m, 2H), 1.28 (m, 4H). $^{13}$C NMR (101 MHz, CD$_3$OD) δ 171.2 (CO), 153.7 (C, Ar), 146.1 (C, Ar), 141.5 (C, Ar), 139.2 (C, Ar), 138.5 (C, Ar), 134.0 (C, Ar), 134.0 (CH, Ar), 130.0 (2 CH, Ar), 129.7 (2 CH, Ar), 129.4 (2 CH, Ar), 129.3 (2 CH, Ar), 115.9 (CH, Ar), 112.9 (CH, Ar), 112.2 (C Ar—COOH), 61.2 (CH, Cp), 53.3 (CH2), 52.8 (CH2), 48.0 (CH2), 46.9 (CH2), 33.8 (CH2-piperidine), 30.3 (CH3), 30.2 (2 CH2), 29.6 (2 CH2), 24.3 (2 CH2). HRMS (ESI): calc. for [M+H]$^+$ C33H42ClN4O6S2: 689.2156, found: 689.2228.

Example A-17. Preparation of tert-Butyl 2-azido-4-cyanobenzoate, 21*

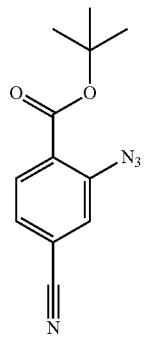 [SMILES: CC(C)(C)OC(=O)c1ccc(C#N)cc1N=[N+]=[N-]]

In a 100 mL round-bottomed flask, sodium azide (764 mg, 11.7 mmol) was dissolved in DMSO (20 mL), and tert-butyl 4-cyano-2-fluorobenzoate (2.0 g, 9.0 mmol) was added and stirred at 50° C. for 6 h. The reaction mixture was cooled and poured into water (200 mL) and extracted with DCM. The organic layers were separated, dried and the solvent removed under vacuum. and 1H NMR spectra showed the material was pure and it was used as such for reaction. Yield: 2.2 g (98%).

$^1$H NMR (400 MHz, cdcl$_3$) δ 7.82 (dd, J=8, 1 Hz, 1H, CH, Ar), 7.44 (m, 2H, 2 CH, Ar), 1.59 (s, 9H, 3 CH3). $^{13}$C NMR (101 MHz, cdcl$_3$) δ 163.4 (CO), 140.8 (C), 132.2 (CH), 128.9 (C), 127.8 (CH), 123.4 (CH), 117.3 (C), 116.2 (C), 83.6 (C, tBu), 28.2 (3 CH3). HRMS (ESI): calc. for [M+H]$^+$ C$_{12}$H$_{13}$N$_4$O$_2$: 245.0960, found: 245.0963. Caution: Azide derivatives can explode and be highly toxic. Handle with care and using a safety shield.

Example A-18. Preparation of tert-Butyl 2-amino-4-cyanobenzoate, 22*

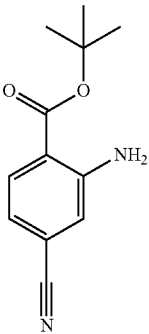 [SMILES: CC(C)(C)OC(=O)c1ccc(C#N)cc1N]

tert-Butyl 2-azido-4-cyanobenzoate (2.0 g, 8.2 mmol), NaBH$_4$ (619 mg, 16.4 mmol), and THF (3 mL/mmol) were charged to a round-bottom flask with a stir bar under argon atmosphere fitted with a reflux condenser. The reaction mixture immediately began to evolve nitrogen; once the gas evolution slowed, the reaction vessel was heated up to 65° C. and stirred for 1 h. The reaction mixture was then cooled to room temperature and concentrated to dryness. Water was added, then HCl 1 M and the mixture was extracted with DCM. The organic layer was separated, then washed with brine, dried over MgSO$_4$, filtered and concentrated in vacuo. The product (1.7 g, 99% yield) was used in the next reaction without further purification.

$^1$H NMR (400 MHz, cdcl$_3$) δ 7.87 (dd, J=8, 4 Hz, 1H, CH, Ar), 6.91 (m, 1H, CH, Ar), 6.85 (dd, J=8, 3 Hz, 1H, CH, Ar), 1.58 (s, 9H, 3 CH3). $^{13}$C NMR (101 MHz, cdcl$_3$) δ 167.9 (CO), 149.9 (C), 132.5 (CH), 120.2 (CH), 118.8 (CH), 118.5 (C), 116.7 (C), 115.9 (C), 82.2 (C, tBu), 28.4 (3 CH3). HRMS (ESI): calc. for [M+H]+C$_{12}$H$_{15}$N$_2$O$_2$: 219.1055, found: 219.1128.

Example A-19. Preparation of tert-Butyl 4-(((3-amino-4-(tert-butoxycarbonyl)benzyl)amino)methyl)piperidine-1-carboxylate, 23*

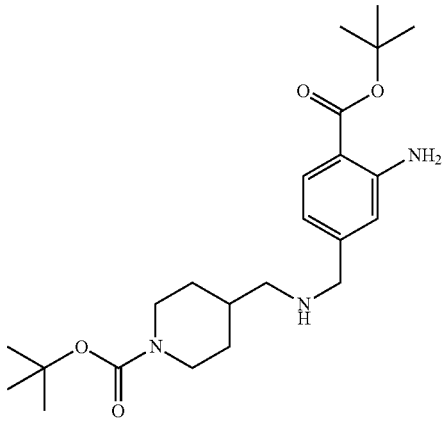 [SMILES: CC(C)(C)OC(=O)c1ccc(CNCC2CCN(C(=O)OC(C)(C)C)CC2)cc1N]

First, DIBAL-H (1 M solution in toluene, 0.82 mL, 0.82 mmol, 1.2 eq) was added dropwise at −40° C. to a solution of tert-butyl 2-amino-4-cyanobenzoate (150 mg, 0.69 mmol) in CH$_2$Cl$_2$ (4 mL/mmol), and stirred for 3 h. The reaction mixture was then quenched with MeOH (0.1 mL) and Rochelle's solution (4 mL). The mixture was warmed to ambient temperature, stirred for 1 h and diluted with CH$_2$Cl$_2$. The organic layer was separated, then washed with brine, dried over MgSO$_4$, filtered and concentrated in vacuo. The complex mixture was then subjected to the next reaction. The title compound (104 mg, 36% yield, two steps) was prepared according to the reductive amination procedure II by using crude tert-butyl 2-amino-4-formylbenzoate, tert-butyl 4-(aminomethyl)piperidine-1-carboxylate (145 mg, 0.68 mmol), sodium triacetoxyborohydride (287 mg, 1.4 mmol), and acetic acid (81 µL, 1.4 mmol). Purification of the resulting mixture was carried out on preparative HPLC using a reversed-phase C18 column (RP C18, flow 20.0 mL/min, solvent A: 0.1% TFA in water, solvent B: 0.1% TFA in acetonitrile, from 10% B to 100% B) 36% yield.

$^1$H NMR (400 MHz, cdcl$_3$) δ 7.86 (d, J=8 Hz, 1H, CH, Ar), 6.98 (s, 1H, CH, Ar), 6.80 (d, J=8 Hz, 1H, CH, Ar), 4.05 (m, 4H, including CH2-Ar), 2.83 (bs, 2H, CH2-piperidine), 2.66 (t, J=12 Hz, 2H), 1.88 (s, 1H, CH), 1.70 (m, 2H), 1.56 (s, 9H, 3 CH3), 1.42 (s, 9H, 3 CH3), 1.11 (dt, J=12, 9 Hz, 2H). $^{13}$C NMR (101 MHz, cdcl$_3$) b 166.6 (CO), 155.4 (CO), 146.2 (C), 135.5 (C), 132.8 (CH), 120.5 (CH), 120.0 (CH), 114.1 (C), 82.7 (C, tBu), 81.2 (C, tBu), 52.6 (CH2-piperidine), 51.6 (CH2-Ar), 43.3 (2 CH2), 33.7 (CH), 29.4 (2 CH2), 28.5 (3 CH3), 28.2 (3 CH3). HRMS (ESI): calc. for [M+H]$^+$ C23H38N3O4: 420.2784, found: 420.2776.

Example A-20. Preparation of 2-amino-4-(((4-(N-(4-chlorobenzyl)-N-cyclopentylsulfamoyl)-N-(piperidin-4-ylmethyl)phenyl)sulfonamido) methyl)benzoic Acid 22

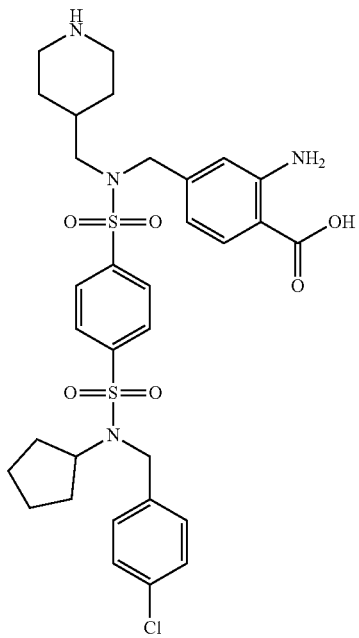 [SMILES: Nc1cc(CN(CC2CCNCC2)S(=O)(=O)c2ccc(S(=O)(=O)N(Cc3ccc(Cl)cc3)C3CCCC3)cc2)ccc1C(=O)O]

A solution of 4-(N-(4-chlorobenzyl)-N-cyclopentylsulfamoyl)-benzenesulfonyl chloride (80 mg, 0.18 mmol) and tert-butyl 4-(((3-amino-4-(tert-butoxycarbonyl)benzyl)amino)methyl)-piperidine-1-carboxylate (102 mg, 0.20 mmol) in dichloromethane (25 mL/mmol) was treated with triethylamine (30 uL, 0.21 mmol) and stirred at 0° C. for 30 min. Water was then added and the product was extracted into DCM. The combined extracts were dried over MgSO$_4$ and filtered. The solvent was reduced and Boc deprotection was then done in situ by slowly adding to the mixture TFA (~10 eq), and this reaction was then stirred for 2 h at room temperature. The solvent was evaporated and purification of the resulting mixture was carried out on preparative HPLC using a reversed-phase C18 column (RP C18, flow 20.0 mL/min, solvent A: 0.1% TFA in water, solvent B: 0.1% TFA in acetonitrile, from 10% B to 100% B). The solvent was freeze dried to afford the pure product (149 mg, 47% yield) as a white solid (TFA salt).

$^1$H NMR (500 MHz, MeOD) δ 8.04 (s, 4H, 4 CH Ar), 7.76 (d, J=8 Hz, 1H, CH Ar), 7.37 (dd, J=35, 9 Hz, 4H, 4 CH Ar), 6.73 (s, 1H, CH Ar), 6.47 (dd, J=8, 2 Hz, 1H, CH Ar), 4.43 (s, 2H, CH2), 4.38 (m, 1H, CH Cp), 4.31 (s, 2H, CH2), 3.37 (s, 2H, CH2), 3.19 (d, J=7 Hz, 2H, CH2), 2.81 (dd, J=13, 10 Hz, 2H), 1.91 (d, J=13 Hz, 2H), 1.80 (m, 1H, CH piperidine), 1.65 (m, 2H), 1.57 (m, 2H), 1.45 (m, 2H), 1.31 (m, 4H). $^{13}$C NMR (126 MHz, MeOD) δ 170.1 (CO), 152.0 (C, Ar), 145.0 (C, Ar), 143.4 (C, Ar), 142.51 (C, Ar), 138.2 (C, Ar), 133.0 (C, Ar), 132.2 (CH, Ar), 129.0 (2 CH, Ar), 128.5 (2 CH, Ar), 128.3 (2 CH, Ar), 128.3 (2 CH, Ar), 116.6 (CH, Ar), 115.5 (CH, Ar), 110.2 (C Ar—COOH), 60.2 (CH, Cp), 54.2 (CH2), 53.0 (CH2), 47.0 (CH2), 43.8 (2 CH2), 33.0 (CH2, piperidine), 29.4 (2 CH2), 26.6 (2 CH2), 23.4 (2 CH2). HRMS (ESI): calc. for [M+H]$^+$ C32H40ClN4O6S2: 675.2000, found: 675.2072.

The compounds in the following table were prepared similar to the procedure described in the previous example. The purification of the crude product was performed by flash silica gel column chromatography with MeOH and CH$_2$Cl$_2$ as eluents, by reverse phase RP-HPLC (column: Cl18), using H$_2$O (0.1% TFA) and ACN (0.1% TFA) as eluents or by precipitation.

| No. | Structure | MW | [M + H]$^+$ |
|---|---|---|---|
| 1 | 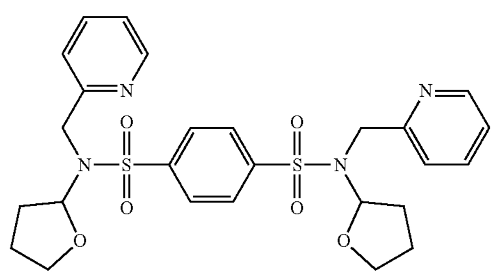 [SMILES: O=S(=O)(c1ccc(S(=O)(=O)N(Cc2ccccn2)C2CCCO2)cc1)N(Cc1ccccn1)C1CCCO1] | 558 | 559 |
| 2 | 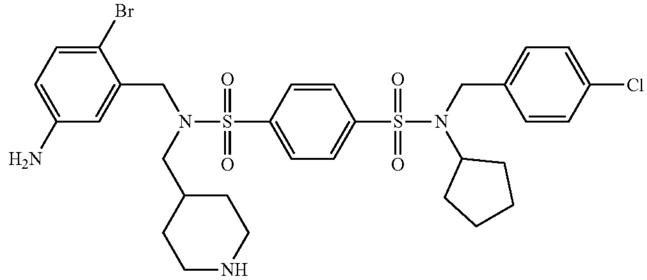 [SMILES: Nc1ccc(Br)c(CN(CC2CCNCC2)S(=O)(=O)c2ccc(S(=O)(=O)N(Cc3ccc(Cl)cc3)C3CCCC3)cc2)c1] | 710 | 711 |

| No. | Structure | MW | [M + H]+ |
|---|---|---|---|
| 3 | 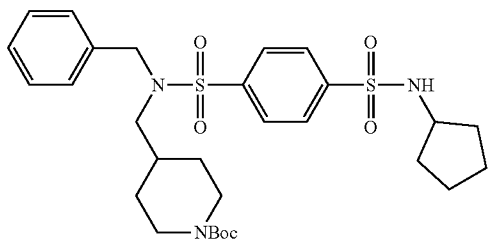 [SMILES: CC(C)(C)OC(=O)N1CCC(CN(Cc2ccccc2)S(=O)(=O)c2ccc(S(=O)(=O)NC3CCCC3)cc2)CC1] | 591 | 592 |
| 4 | 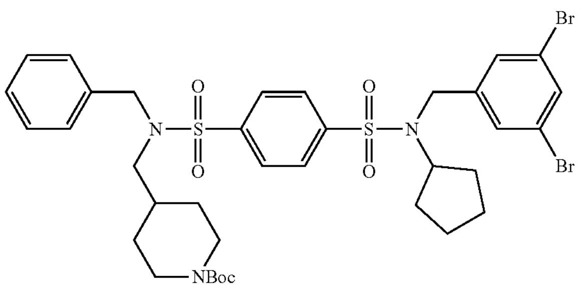 [SMILES: CC(C)(C)OC(=O)N1CCC(CN(Cc2ccccc2)S(=O)(=O)c2ccc(S(=O)(=O)N(Cc3cc(Br)cc(Br)c3)C3CCCC3)cc2)CC1] | 839 | 840 |
| 5 | 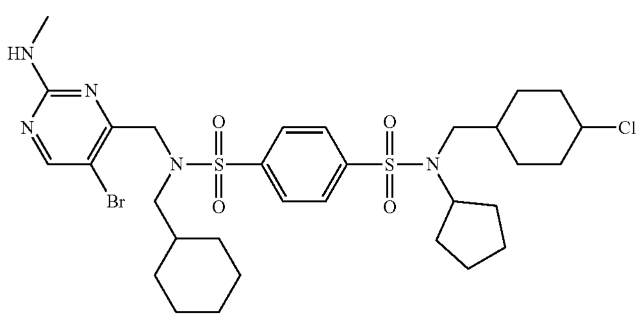 [SMILES: CNc1ncc(Br)c(CN(CC2CCCCC2)S(=O)(=O)c2ccc(S(=O)(=O)N(CC3CCC(Cl)CC3)C3CCCC3)cc2)n1] | 725 | 726 |
| 6 | 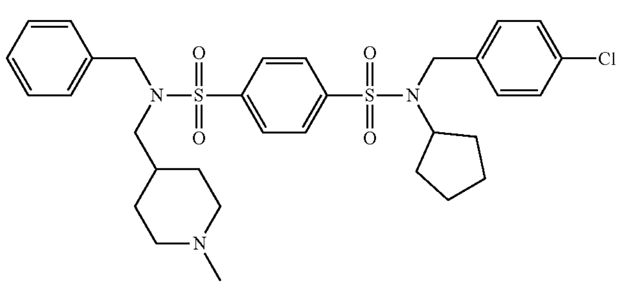 [SMILES: CN1CCC(CN(Cc2ccccc2)S(=O)(=O)c2ccc(S(=O)(=O)N(Cc3ccc(Cl)cc3)C3CCCC3)cc2)CC1] | 630 | 631 |

-continued
| No. | Structure | MW | [M + H]+ |
|---|---|---|---|
| 7 | 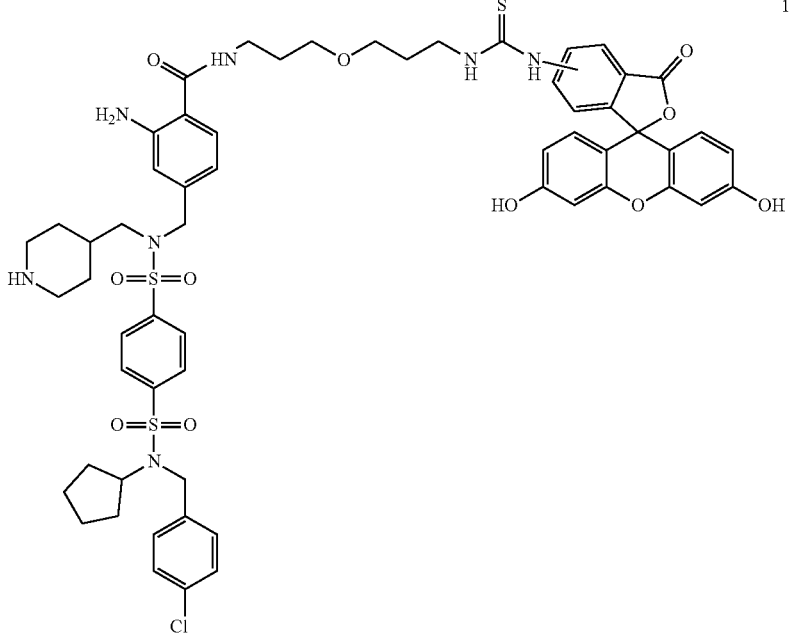 | 1194 | 1195 |
| 8 | 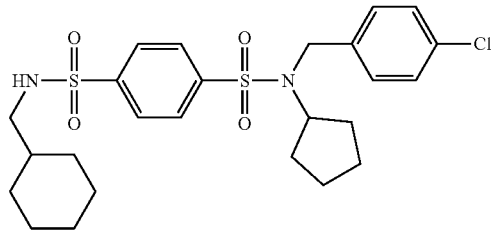 [SMILES: O=S(=O)(NCC1CCCCC1)c1ccc(S(=O)(=O)N(Cc2ccc(Cl)cc2)C2CCCC2)cc1] | 525 | 526 |
| 9 | 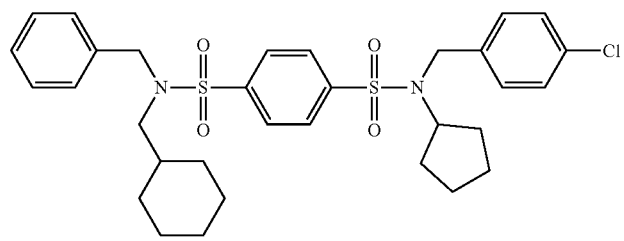 [SMILES: O=S(=O)(c1ccc(S(=O)(=O)N(Cc2ccc(Cl)cc2)C2CCCC2)cc1)N(Cc1ccccc1)CC1CCCCC1] | 615 | 616 |
| 10 | 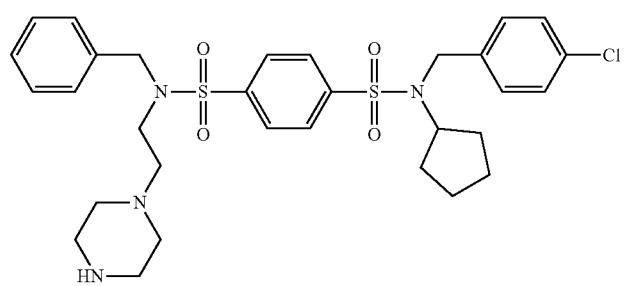 [SMILES: O=S(=O)(c1ccc(S(=O)(=O)N(Cc2ccc(Cl)cc2)C2CCCC2)cc1)N(CCN1CCNCC1)Cc1ccccc1] | 631 | 632 |

-continued

| No. | Structure | MW | [M + H]+ |
|---|---|---|---|
| 11 | 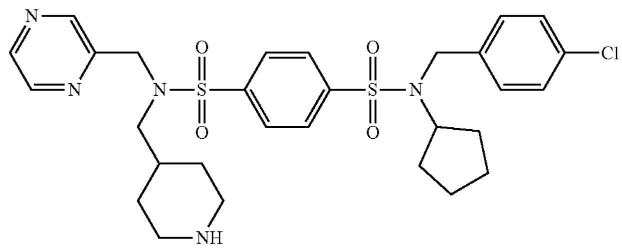 [SMILES: O=S(=O)(c1ccc(S(=O)(=O)N(Cc2ccc(Cl)cc2)C2CCCC2)cc1)N(Cc1cnccn1)CC1CCNCC1] | 618 | 619 |
| 12 | 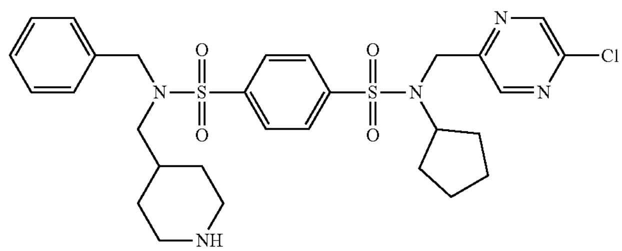 [SMILES: O=S(=O)(c1ccc(S(=O)(=O)N(Cc2cnc(Cl)cn2)C2CCCC2)cc1)N(Cc1ccccc1)CC1CCNCC1] | 618 | 619 |
| 13 | 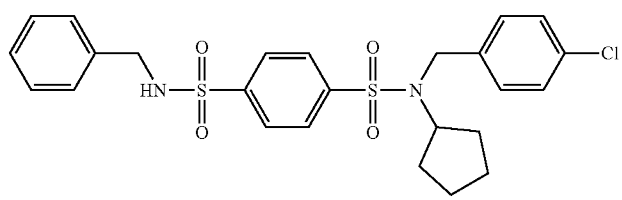 [SMILES: O=S(=O)(NCc1ccccc1)c1ccc(S(=O)(=O)N(Cc2ccc(Cl)cc2)C2CCCC2)cc1] | 519 | 520 |
| 14 | 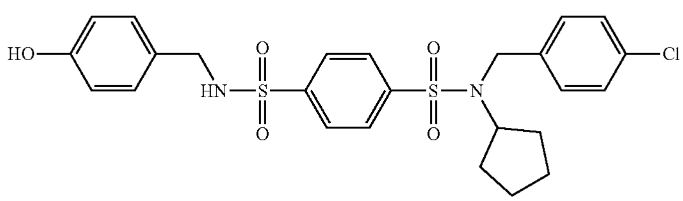 [SMILES: O=S(=O)(NCc1ccc(O)cc1)c1ccc(S(=O)(=O)N(Cc2ccc(Cl)cc2)C2CCCC2)cc1] | 535 | 536 |
| 15 | 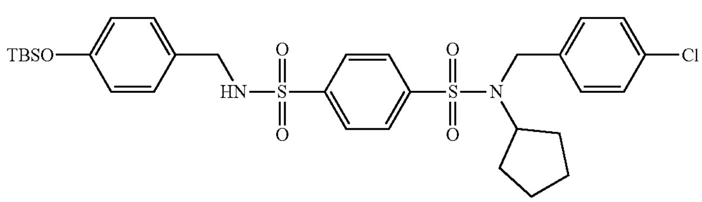 [SMILES: CC(C)(C)[Si](C)(C)Oc1ccc(CNS(=O)(=O)c2ccc(S(=O)(=O)N(Cc3ccc(Cl)cc3)C3CCCC3)cc2)cc1] | 649 | 650 |
| 16 | 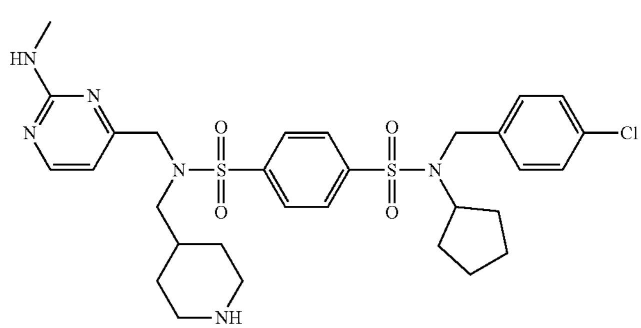 [SMILES: CNc1nccc(CN(CC2CCNCC2)S(=O)(=O)c2ccc(S(=O)(=O)N(Cc3ccc(Cl)cc3)C3CCCC3)cc2)n1] | 647 | 648 |

-continued

| No. | Structure | MW | [M + H]+ |
|---|---|---|---|
| 17 | 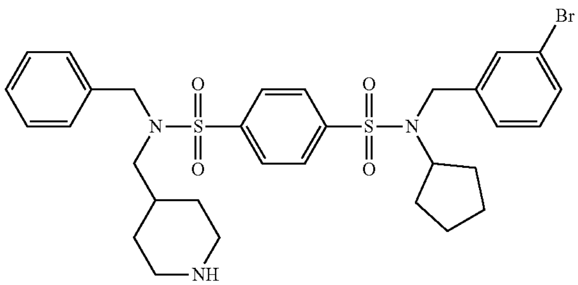 [SMILES: O=S(=O)(c1ccc(S(=O)(=O)N(Cc2cccc(Br)c2)C2CCCC2)cc1)N(Cc1ccccc1)CC1CCNCC1] | 660 | 661 |
| 18 | 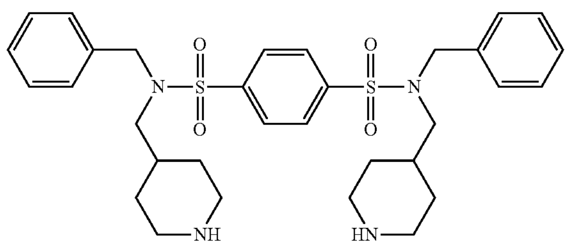 [SMILES: O=S(=O)(c1ccc(S(=O)(=O)N(Cc2ccccc2)CC2CCNCC2)cc1)N(Cc1ccccc1)CC1CCNCC1] | 611 | 612 |
| 19 | 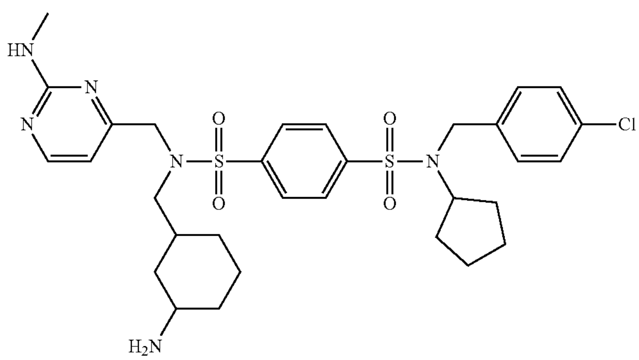 [SMILES: CNc1nccc(CN(CC2CCCC(N)C2)S(=O)(=O)c2ccc(S(=O)(=O)N(Cc3ccc(Cl)cc3)C3CCCC3)cc2)n1] | 647 | 648 |
| 20 | 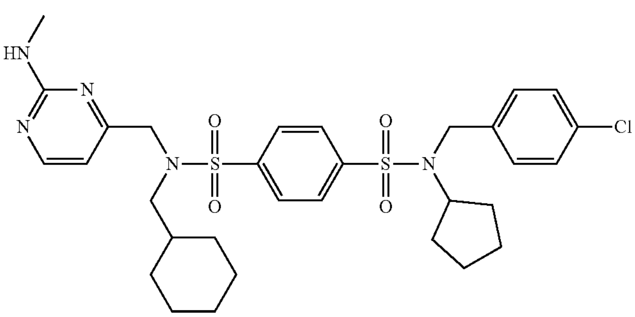 [SMILES: CNc1nccc(CN(CC2CCCCC2)S(=O)(=O)c2ccc(S(=O)(=O)N(Cc3ccc(Cl)cc3)C3CCCC3)cc2)n1] | 646 | 647 |
| 21 | 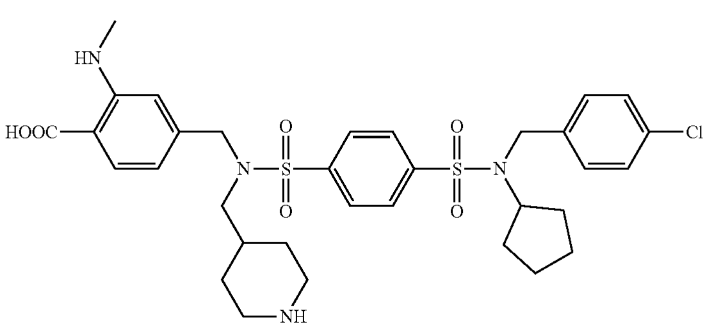 [SMILES: CNc1cc(CN(CC2CCNCC2)S(=O)(=O)c2ccc(S(=O)(=O)N(Cc3ccc(Cl)cc3)C3CCCC3)cc2)ccc1C(=O)O] | 689 | 690 |

| No. | Structure | MW | [M + H]+ |
|---|---|---|---|
| 22 | 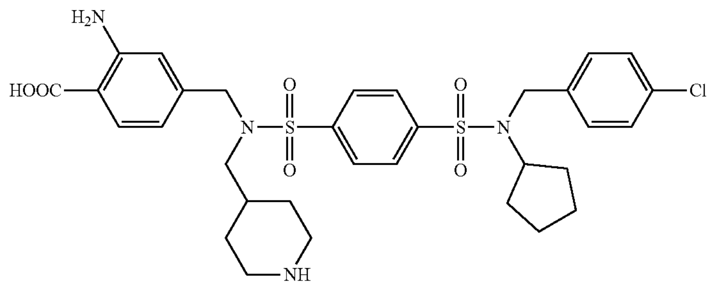 [SMILES: Nc1cc(CN(CC2CCNCC2)S(=O)(=O)c2ccc(S(=O)(=O)N(Cc3ccc(Cl)cc3)C3CCCC3)cc2)ccc1C(=O)O] | 675 | 676 |
| 23 | 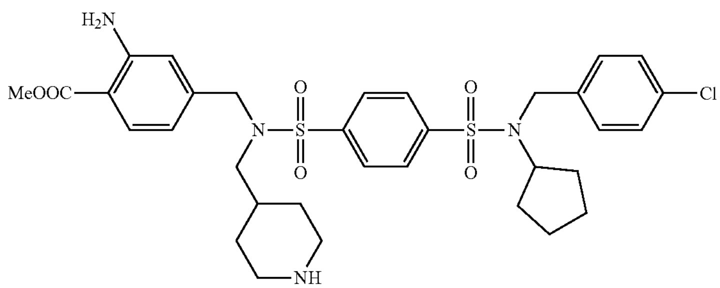 [SMILES: COC(=O)c1ccc(CN(CC2CCNCC2)S(=O)(=O)c2ccc(S(=O)(=O)N(Cc3ccc(Cl)cc3)C3CCCC3)cc2)cc1N] | 689 | 690 |
| 24 | 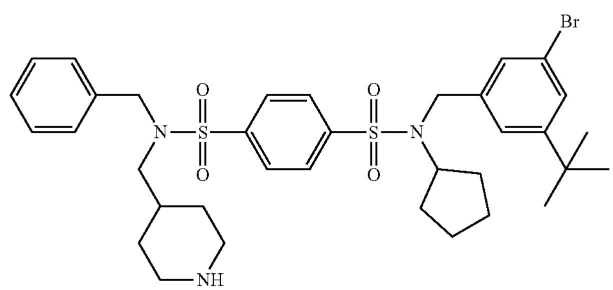 [SMILES: CC(C)(C)c1cc(Br)cc(CN(C2CCCC2)S(=O)(=O)c2ccc(S(=O)(=O)N(Cc3ccccc3)CC3CCNCC3)cc2)c1] | 717 | 718 |
| 25 | 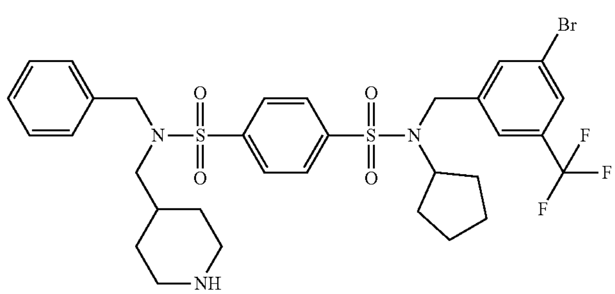 [SMILES: O=S(=O)(c1ccc(S(=O)(=O)N(Cc2cc(Br)cc(C(F)(F)F)c2)C2CCCC2)cc1)N(Cc1ccccc1)CC1CCNCC1] | 729 | 730 |
| 26 | 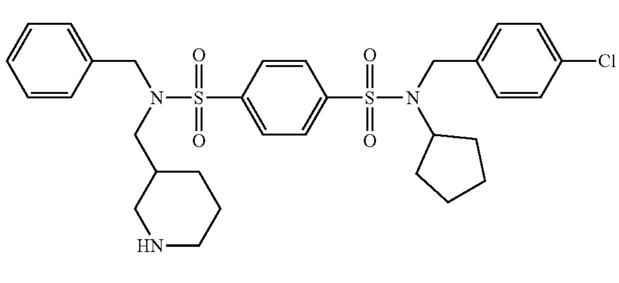 [SMILES: O=S(=O)(c1ccc(S(=O)(=O)N(Cc2ccc(Cl)cc2)C2CCCC2)cc1)N(Cc1ccccc1)CC1CCCNC1] | 616 | 617 |

-continued

| No. | Structure | MW | [M + H]+ |
|---|---|---|---|
| 27 | 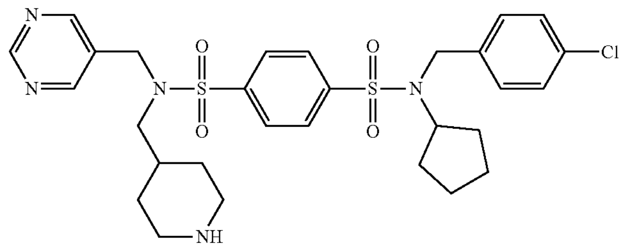 [SMILES: O=S(=O)(c1ccc(S(=O)(=O)N(Cc2ccc(Cl)cc2)C2CCCC2)cc1)N(Cc1cncnc1)CC1CCNCC1] | 618 | 619 |
| 28 | 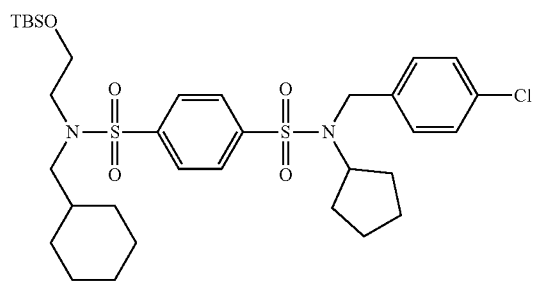 [SMILES: CC(C)(C)[Si](C)(C)OCCN(CC1CCCCC1)S(=O)(=O)c1ccc(S(=O)(=O)N(Cc2ccc(Cl)cc2)C2CCCC2)cc1] | 683 | 684 |
| 29 | 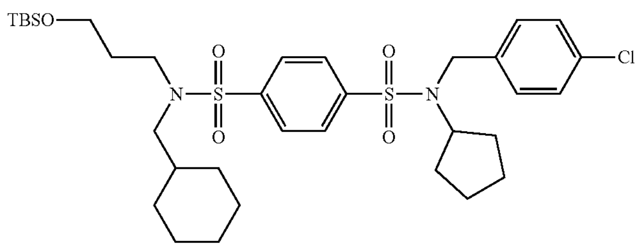 [SMILES: CC(C)(C)[Si](C)(C)OCCCN(CC1CCCCC1)S(=O)(=O)c1ccc(S(=O)(=O)N(Cc2ccc(Cl)cc2)C2CCCC2)cc1] | 697 | 698 |
| 30 | 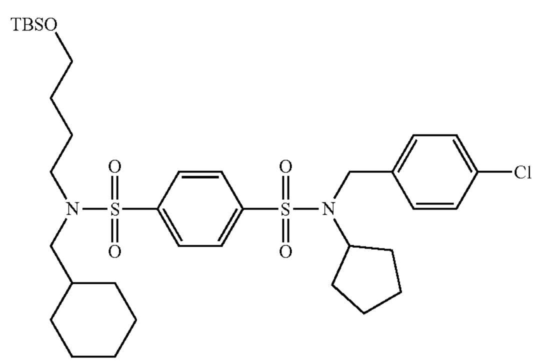 [SMILES: CC(C)(C)[Si](C)(C)OCCCCN(CC1CCCCC1)S(=O)(=O)c1ccc(S(=O)(=O)N(Cc2ccc(Cl)cc2)C2CCCC2)cc1] | 711 | 712 |
| 31 | 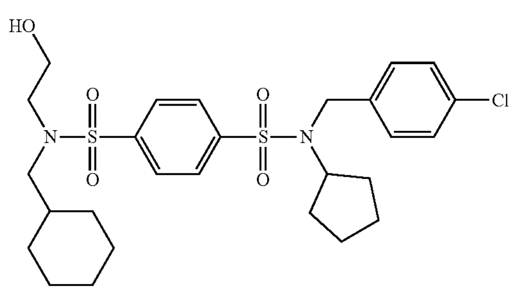 [SMILES: O=S(=O)(c1ccc(S(=O)(=O)N(Cc2ccc(Cl)cc2)C2CCCC2)cc1)N(CCO)CC1CCCCC1] | 569 | 570 |

-continued

| No. | Structure | MW | [M + H]+ |
|---|---|---|---|
| 32 | 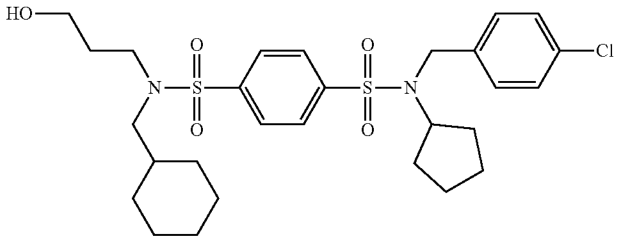 [SMILES: O=S(=O)(c1ccc(S(=O)(=O)N(Cc2ccc(Cl)cc2)C2CCCC2)cc1)N(CCCO)CC1CCCCC1] | 583 | 584 |
| 33 | 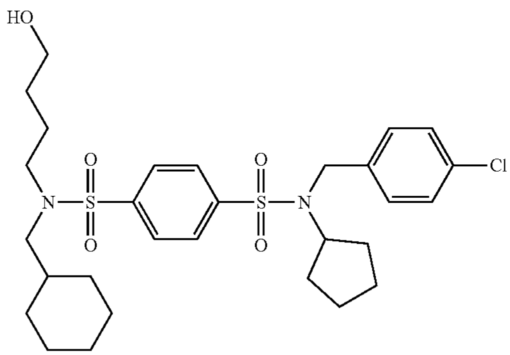 [SMILES: O=S(=O)(c1ccc(S(=O)(=O)N(Cc2ccc(Cl)cc2)C2CCCC2)cc1)N(CCCCO)CC1CCCCC1] | 597 | 598 |
| 34 | 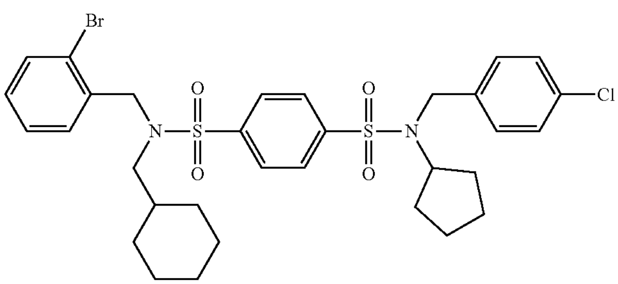 [SMILES: O=S(=O)(c1ccc(S(=O)(=O)N(Cc2ccc(Cl)cc2)C2CCCC2)cc1)N(Cc1ccccc1Br)CC1CCCCC1] | 694 | 695 |
| 35 | 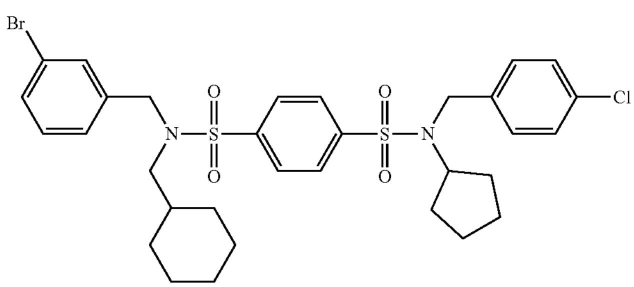 [SMILES: O=S(=O)(c1ccc(S(=O)(=O)N(Cc2ccc(Cl)cc2)C2CCCC2)cc1)N(Cc1cccc(Br)c1)CC1CCCCC1] | 694 | 695 |
| 36 | 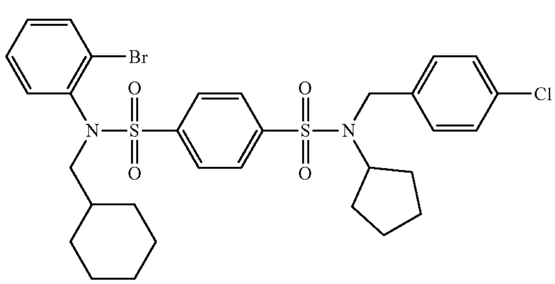 [SMILES: O=S(=O)(c1ccc(S(=O)(=O)N(Cc2ccc(Cl)cc2)C2CCCC2)cc1)N(CC1CCCCC1)c1ccccc1Br] | 680 | 6811 |

-continued

| No. | Structure | MW | [M + H]+ |
|---|---|---|---|
| 37 | 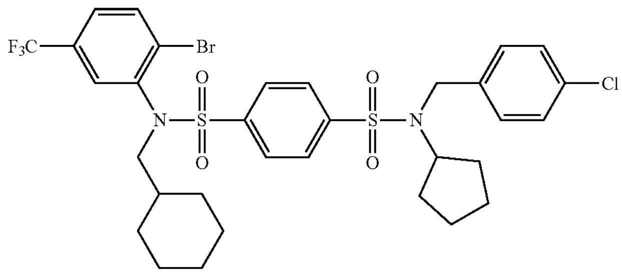 [SMILES: O=S(=O)(c1ccc(S(=O)(=O)N(Cc2ccc(Cl)cc2)C2CCCC2)cc1)N(CC1CCCCC1)c1cc(C(F)(F)F)ccc1Br] | 748 | 749 |
| 38 | 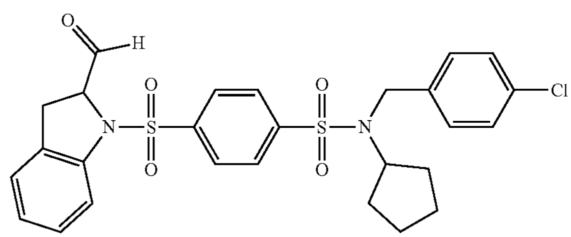 [SMILES: O=CC1Cc2ccccc2N1S(=O)(=O)c1ccc(S(=O)(=O)N(Cc2ccc(Cl)cc2)C2CCCC2)cc1] | 559 | 560 |
| 39 | 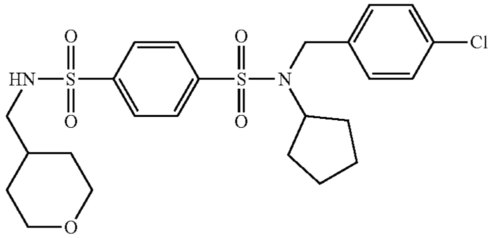 [SMILES: O=S(=O)(NCC1CCOCC1)c1ccc(S(=O)(=O)N(Cc2ccc(Cl)cc2)C2CCCC2)cc1] | 527 | 528 |
| 40 | 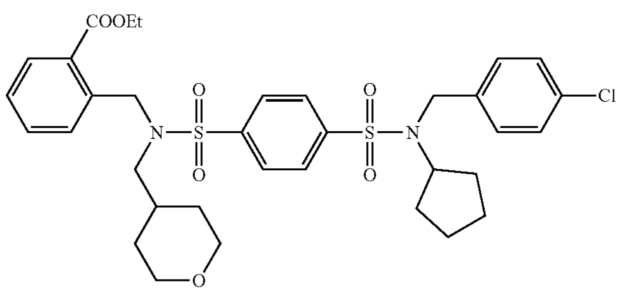 [SMILES: CCOC(=O)c1ccccc1CN(CC1CCOCC1)S(=O)(=O)c1ccc(S(=O)(=O)N(Cc2ccc(Cl)cc2)C2CCCC2)cc1] | 689 | 690 |
| 41 | 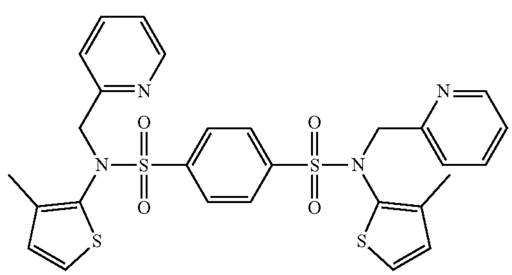 [SMILES: Cc1ccsc1N(Cc1ccccn1)S(=O)(=O)c1ccc(S(=O)(=O)N(Cc2ccccn2)c2sccc2C)cc1] | 611 | 612 |
| 42 | 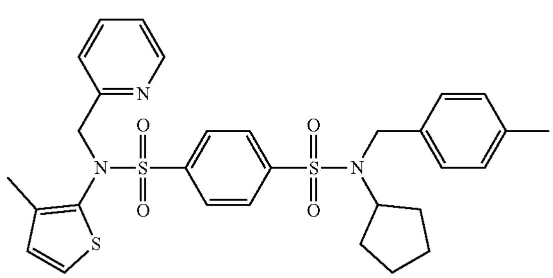 | 596 | 597 |

-continued

| No. | Structure | MW | [M + H]⁺ |
|---|---|---|---|
| 43 | 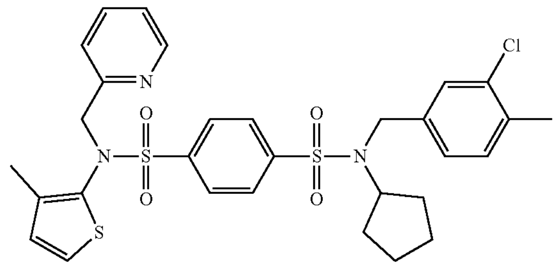 | 630 | 631 |
| 44 | 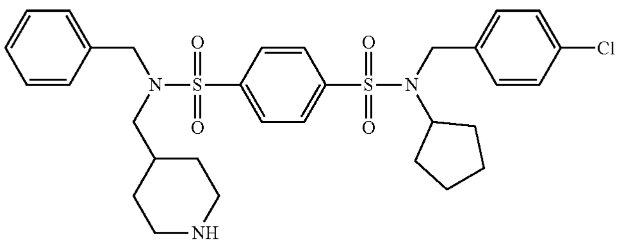 [SMILES: O=S(=O)(c1ccc(S(=O)(=O)N(Cc2ccc(Cl)cc2)C2CCCC2)cc1)N(Cc1ccccc1)CC1CCNCC1] | 616 | 617 |

In the present invention, the biological activity, especially inhibitory activity against PDEδ of the following compounds are also measured.

| No. | Structure | Nomenclature |
|---|---|---|
| 45 | 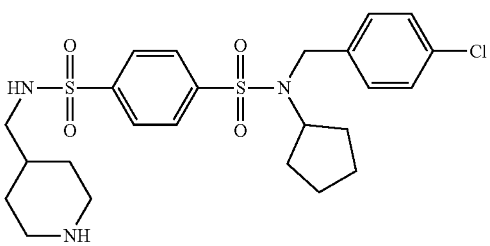 [SMILES: O=S(=O)(NCC1CCNCC1)c1ccc(S(=O)(=O)N(Cc2ccc(Cl)cc2)C2CCCC2)cc1] | N1-(4-chlorobenzyl)-N1-cyclopentyl-N4-(piperidin-4-ylmethyl)benzene-1,4-disulfonamide |
| 46 | 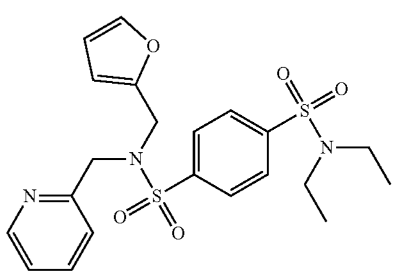 [SMILES: CCN(CC)S(=O)(=O)c1ccc(S(=O)(=O)N(Cc2ccccn2)Cc2ccco2)cc1] | N1,N1-diethyl-N4-(furan-2-ylmethyl)-N4-(pyridin-2-ylmethyl)benzene-1,4-disulfonamide |
| 47 | 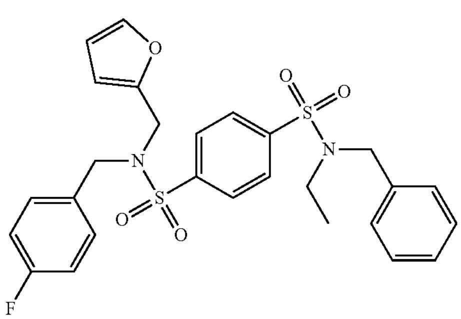 [SMILES: CCN(Cc1ccccc1)S(=O)(=O)c1ccc(S(=O)(=O)N(Cc2ccc(F)cc2)Cc2ccco2)cc1] | N1-benzyl-N1-ethyl-N4-(4-fluorobenzyl)-N4-(furan-2-ylmethyl)benzene-1,4-disulfonamide |

| No. | Structure | Nomenclature |
| --- | --- | --- |
| 48 | 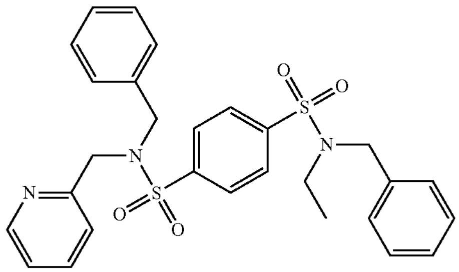 [SMILES: CCN(Cc1ccccc1)S(=O)(=O)c1ccc(S(=O)(=O)N(Cc2ccccc2)Cc2ccccn2)cc1] | N1,N4-dibenzyl-N1-ethyl-N4-(pyridin-2-ylmethyl)benzene-1,4-disulfonamide |
| 49 | 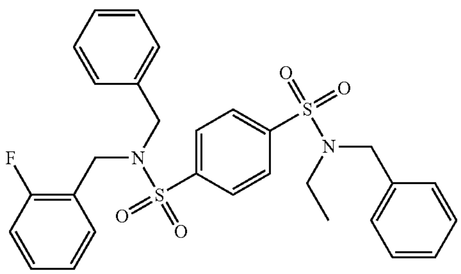 [SMILES: CCN(Cc1ccccc1)S(=O)(=O)c1ccc(S(=O)(=O)N(Cc2ccccc2)Cc2ccccc2F)cc1] | N1,N4-dibenzyl-N1-ethyl-N4-(2-fluorobenzyl)benzene-1,4-disulfonamide |
| 50 | 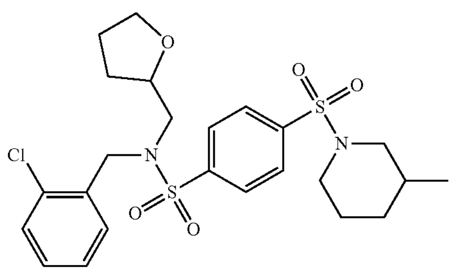 [SMILES: CC1CCCN(S(=O)(=O)c2ccc(S(=O)(=O)N(Cc3ccccc3Cl)CC3CCCO3)cc2)C1] | N-(2-chlorobenzyl)-4-((3-methylpiperidin-1-yl)sulfonyl)-N-((tetrahydrofuran-2-yl)methyl)benzenesulfonamide |
| 51 | 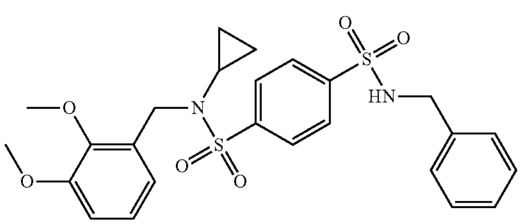 [SMILES: COc1cccc(CN(C2CC2)S(=O)(=O)c2ccc(S(=O)(=O)NCc3ccccc3)cc2)c1OC] | N1-benzyl-N4-cyclopropyl-N4-(2,3-dimethoxybenzyl)benzene-1,4-disulfonamide |
| 52 | 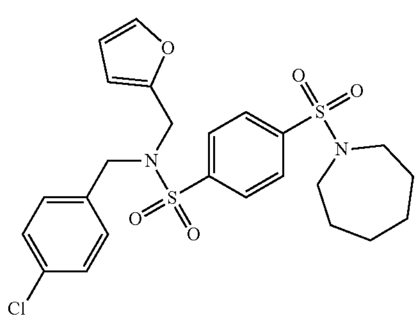 [SMILES: O=S(=O)(c1ccc(S(=O)(=O)N(Cc2ccc(Cl)cc2)Cc2ccco2)cc1)N1CCCCCC1] | 4-(azepan-1-ylsulfonyl)-N-(4-chlorobenzyl)-N-(furan-2-ylmethyl)benzenesulfonamide |

-continued

| No. | Structure | Nomenclature |
|---|---|---|
| 53 | 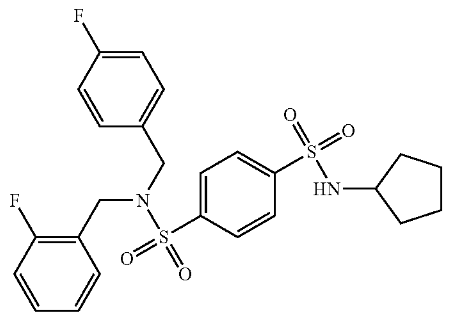 [SMILES: O=S(=O)(NC1CCCC1)c1ccc(S(=O)(=O)N(Cc2ccc(F)cc2)Cc2ccccc2F)cc1] | N1-cyclopentyl-N4-(2-fluorobenzyl)-N4-(4-fluorobenzyl)benzene-1,4-disulfonamide |
| 54 | 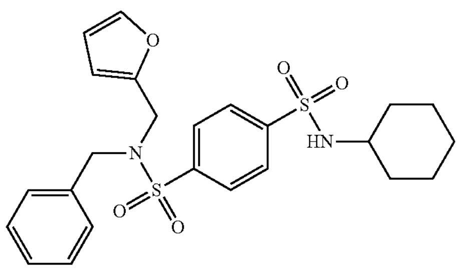 [SMILES: O=S(=O)(NC1CCCCC1)c1ccc(S(=O)(=O)N(Cc2ccccc2)Cc2ccco2)cc1] | N1-benzyl-N4-cyclohexyl-N1-(furan-2-ylmethyl)benzene-1,4-disulfonamide |
| 55 | 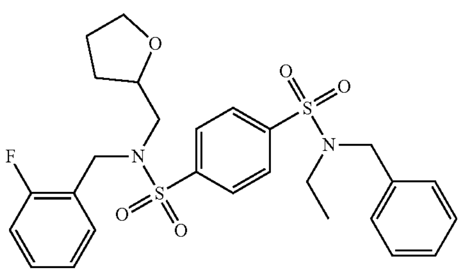 [SMILES: CCN(Cc1ccccc1)S(=O)(=O)c1ccc(S(=O)(=O)N(Cc2ccccc2F)CC2CCCO2)cc1] | N1-benzyl-N1-ethyl-N4-(2-fluorobenzyl)-N4-((tetrahydrofuran-2-yl)methyl)benzene-1,4-disulfonamide |
| 56 | 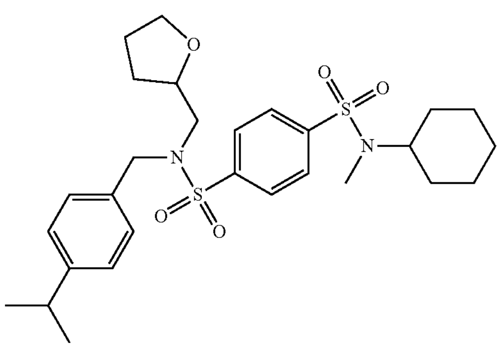 [SMILES: CC(C)c1ccc(CN(CC2CCCO2)S(=O)(=O)c2ccc(S(=O)(=O)N(C)C3CCCCC3)cc2)cc1] | N1-cyclohexyl-N4-(4-isopropylbenzyl)-N1-methyl-N4-((tetrahydrofuran-2-yl)methyl)benzene-1,4-disulfonamide |
| 57 | 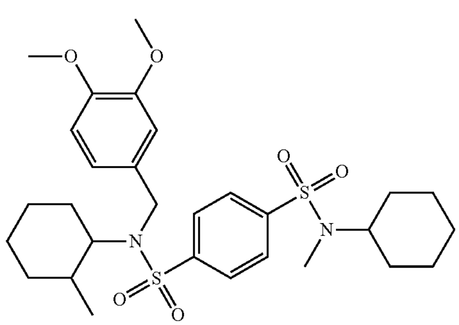 [SMILES: COc1ccc(CN(C2CCCCC2C)S(=O)(=O)c2ccc(S(=O)(=O)N(C)C3CCCCC3)cc2)cc1OC] | N1-cyclohexyl-N4-(3,4-dimethoxybenzyl)-N1-methyl-N4-(2-methylcyclohexyl)benzene-1,4-disulfonamide |

-continued

| No. | Structure | Nomenclature |
|---|---|---|
| 58 | 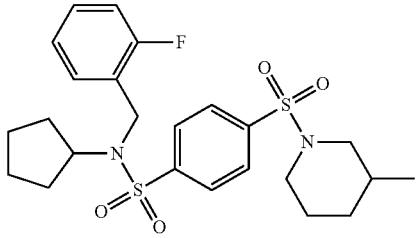 [SMILES: CC1CCCN(S(=O)(=O)c2ccc(S(=O)(=O)N(Cc3ccccc3F)C3CCCC3)cc2)C1] | N-cyclopentyl-N-(2-fluorobenzyl)-4-((3-methylpiperidin-1-yl)sulfonyl)benzenesulfonamide |
| 59 | 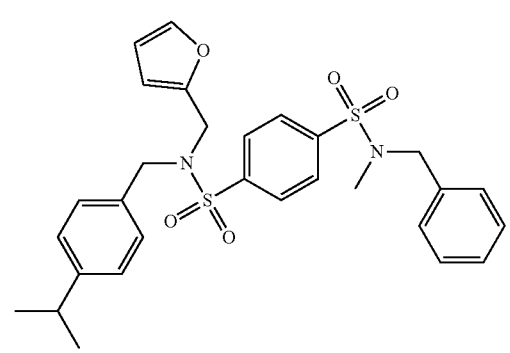 [SMILES: CC(C)c1ccc(CN(Cc2ccco2)S(=O)(=O)c2ccc(S(=O)(=O)N(C)Cc3ccccc3)cc2)cc1] | N1-benzyl-N4-(furan-2-ylmethyl)-N4-(4-isopropylbenzyl)-N1-methylbenzene-1,4-disulfonamide |
| 60 | 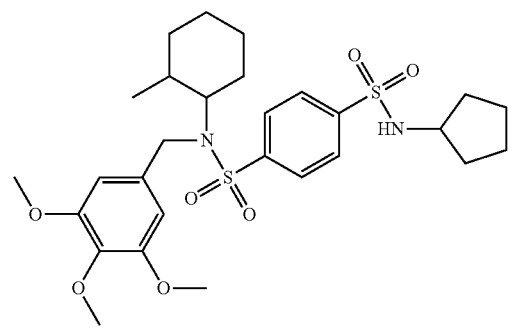 [SMILES: COc1cc(CN(C2CCCCC2C)S(=O)(=O)c2ccc(S(=O)(=O)NC3CCCC3)cc2)cc(OC)c1OC] | N1-cyclopentyl-N4-(2-methylcyclohexyl)-N4-(3,4,5-trimethoxybenzyl)benzene-1,4-disulfonamide |
| 61 | 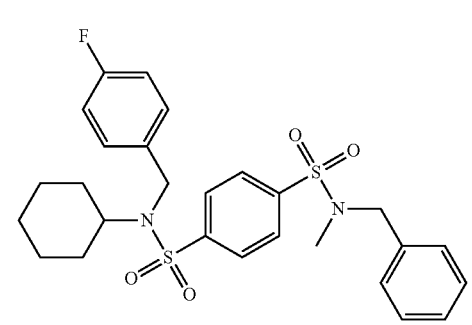 [SMILES: CN(Cc1ccccc1)S(=O)(=O)c1ccc(S(=O)(=O)N(Cc2ccc(F)cc2)C2CCCCC2)cc1] | N1-benzyl-N4-cyclohexyl-N4-(4-fluorobenzyl)-N1-methylbenzene-1,4-disulfonamide |
| 62 | 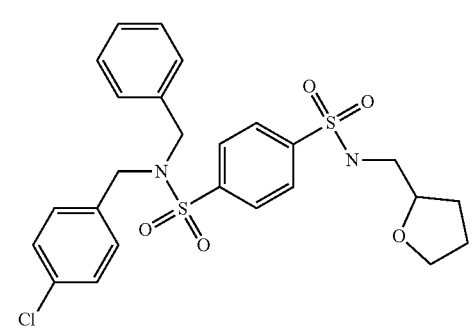 [SMILES: O=S(=O)(NCC1CCCO1)c1ccc(S(=O)(=O)N(Cc2ccccc2)Cc2ccc(Cl)cc2)cc1] | N1-benzyl-N1-(4-chlorobenzyl)-N4-((tetrahydrofuran-2-yl)methyl)benzene-1,4-disulfonamide |

-continued

| No. | Structure | Nomenclature |
|---|---|---|
| 63 | 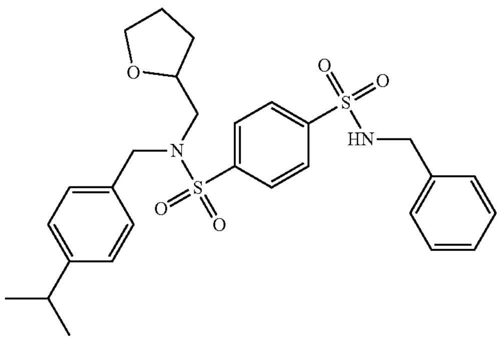 [SMILES: CC(C)c1ccc(CN(CC2CCCO2)S(=O)(=O)c2ccc(S(=O)(=O)NCc3ccccc3)cc2)cc1] | N1-benzyl-N4-(4-isopropylbenzyl)-N4-((tetrahydrofuran-2-yl)methyl)benzene-1,4-disulfonamide |
| 64 | 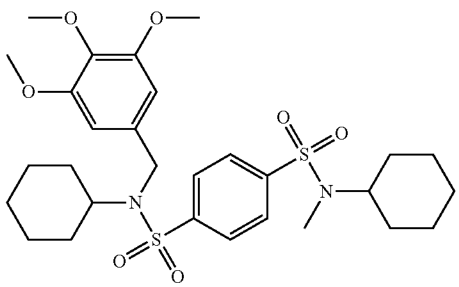 [SMILES: COc1cc(CN(C2CCCCC2)S(=O)(=O)c2ccc(S(=O)(=O)N(C)C3CCCCC3)cc2)cc(OC)c1OC] | N1,N4-dicyclohexyl-N1-methyl-N4-(3,4,5-trimethoxybenzyl)benzene-1,4-disulfonamide |
| 65 | 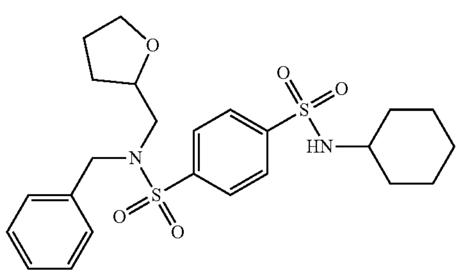 [SMILES: O=S(=O)(NC1CCCCC1)c1ccc(S(=O)(=O)N(Cc2ccccc2)CC2CCCO2)cc1] | N1-benzyl-N4-cyclohexyl-N1-((tetrahydrofuran-2-yl)methyl)benzene-1,4-disulfonamide |
| 66 | 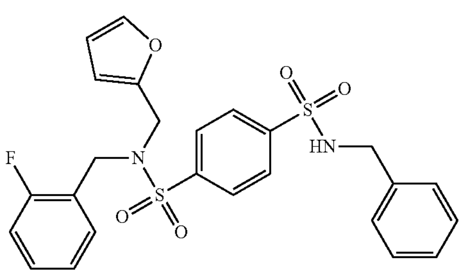 [SMILES: O=S(=O)(NCc1ccccc1)c1ccc(S(=O)(=O)N(Cc2ccco2)Cc2ccccc2F)cc1] | N1-benzyl-N4-(2-fluorobenzyl)-N4-(furan-2-ylmethyl)benzene-1,4-disulfonamide |
| 67 | 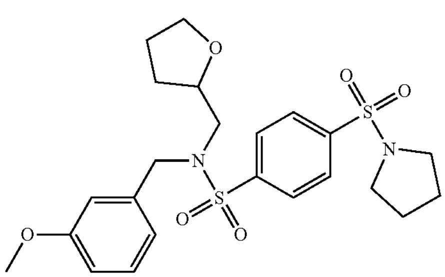 [SMILES: COc1cccc(CN(CC2CCCO2)S(=O)(=O)c2ccc(S(=O)(=O)N3CCCC3)cc2)c1] | N-(3-methoxybenzyl)-4-(pyrrolidin-1-ylsulfonyl)-N-((tetrahydrofuran-2-yl)methyl)benzenesulfonamide |

-continued

| No. | Structure | Nomenclature |
|---|---|---|
| 68 | 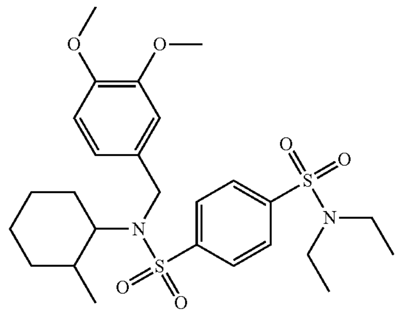 [SMILES: CCN(CC)S(=O)(=O)c1ccc(S(=O)(=O)N(Cc2ccc(OC)c(OC)c2)C2CCCCC2C)cc1] | N1-(3,4-dimethoxybenzyl)-N4,N4-diethyl-N1-(2-methylcyclohexyl)benzene-1,4-disulfonamide |
| 69 | 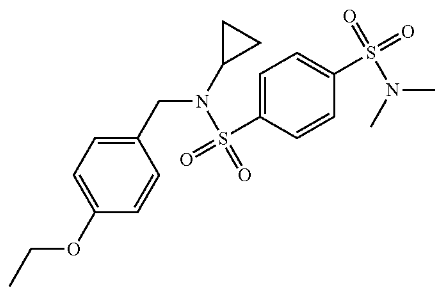 [SMILES: CCOc1ccc(CN(C2CC2)S(=O)(=O)c2ccc(S(=O)(=O)N(C)C)cc2)cc1] | N1-cyclopropyl-N1-(4-ethoxybenzyl)-N4,N4-dimethylbenzene-1,4-disulfonamide |
| 70 | 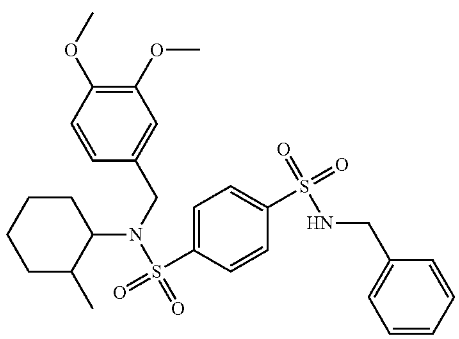 [SMILES: COc1ccc(CN(C2CCCCC2C)S(=O)(=O)c2ccc(S(=O)(=O)NCc3ccccc3)cc2)cc1OC] | N1-benzyl-N4-(3,4-dimethoxybenzyl)-N4-(2-methylcyclohexyl)benzene-1,4-disulfonamide |
| 71 | 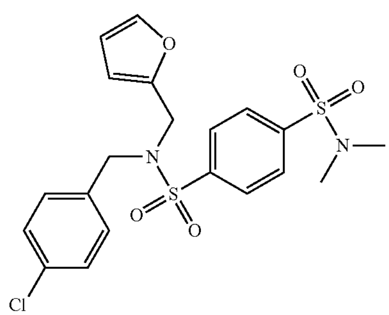 [SMILES: CN(C)S(=O)(=O)c1ccc(S(=O)(=O)N(Cc2ccc(Cl)cc2)Cc2ccco2)cc1] | N1-(4-chlorobenzyl)-N1-(furan-2-ylmethyl)-N4,N4-dimethylbenzene-1,4-disulfonamide |
| 72 | 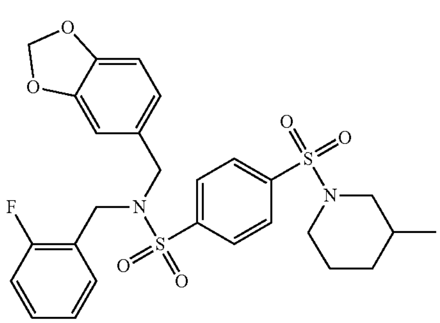 [SMILES: CC1CCCN(S(=O)(=O)c2ccc(S(=O)(=O)N(Cc3ccc4c(c3)OCO4)Cc3ccccc3F)cc2)C1] | N-(benzo[d][1,3]dioxol-5-ylmethyl)-N-(2-fluorobenzyl)-4-((3-methylpiperidin-1-yl)sulfonyl)benzenesulfonamide |

-continued

| No. | Structure | Nomenclature |
|---|---|---|
| 73 | 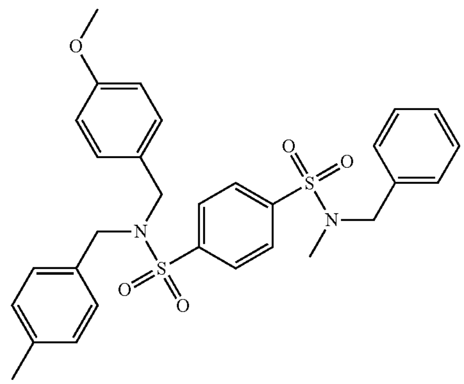 [SMILES: COc1ccc(CN(Cc2ccc(C)cc2)S(=O)(=O)c2ccc(S(=O)(=O)N(C)Cc3ccccc3)cc2)cc1] | N1-benzyl-N4-(4-methoxybenzyl)-N1-methyl-N4-(4-methylbenzyl)benzene-1,4-disulfonamide |
| 74 | 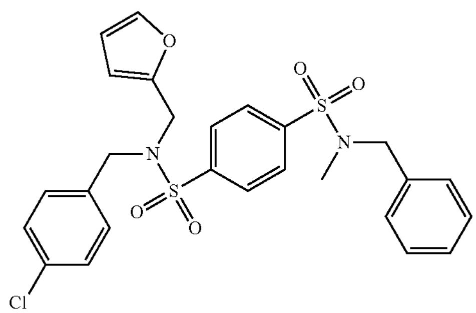 [SMILES: CN(Cc1ccccc1)S(=O)(=O)c1ccc(S(=O)(=O)N(Cc2ccc(Cl)cc2)Cc2ccco2)cc1] | N1-benzyl-N4-(4-chlorobenzyl)-N4-(furan-2-ylmethyl)-N1-methylbenzene-1,4-disulfonamide |
| 75 | 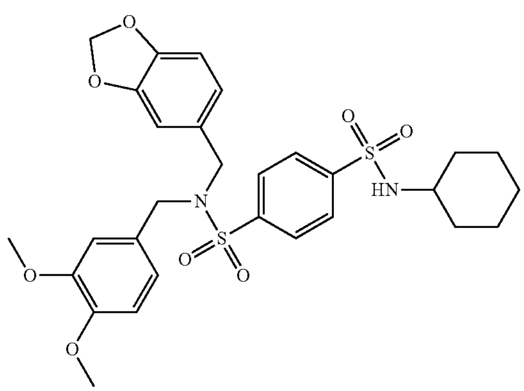 [SMILES: COc1ccc(CN(Cc2ccc3c(c2)OCO3)S(=O)(=O)c2ccc(S(=O)(=O)NC3CCCCC3)cc2)cc1OC] | N1-(benzo[d][1,3]dioxol-5-ylmethyl)-N4-cyclohexyl-N1-(3,4-dimethoxybenzyl)benzene-1,4-disulfonamide |
| 76 | 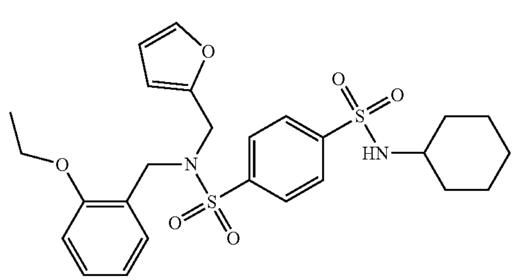 [SMILES: CCOc1ccccc1CN(Cc1ccco1)S(=O)(=O)c1ccc(S(=O)(=O)NC2CCCCC2)cc1] | N1-cyclohexyl-N4-(2-ethoxybenzyl)-N4-(furan-2-ylmethyl)benzene-1,4-disulfonamide |

-continued

| No. | Structure | Nomenclature |
| --- | --- | --- |
| 77 | 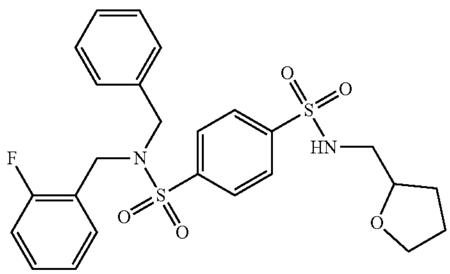 [SMILES: O=S(=O)(NCC1CCCO1)c1ccc(S(=O)(=O)N(Cc2ccccc2)Cc2ccccc2F)cc1] | N1-benzyl-N1-(2-fluorobenzyl)-N4-((tetrahydrofuran-2-yl)methyl)benzene-1,4-disulfonamide |
| 78 | 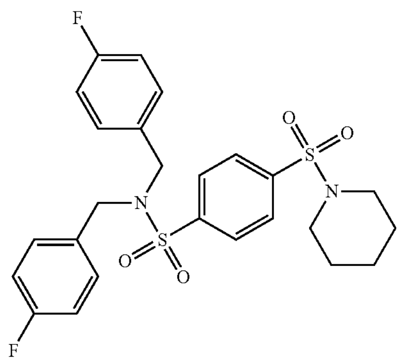 [SMILES: O=S(=O)(c1ccc(S(=O)(=O)N(Cc2ccc(F)cc2)Cc2ccc(F)cc2)cc1)N1CCCCC1] | N,N-bis(4-fluorobenzyl)-4-(piperidin-1-ylsulfonyl)benzenesulfonamide |
| 79 | 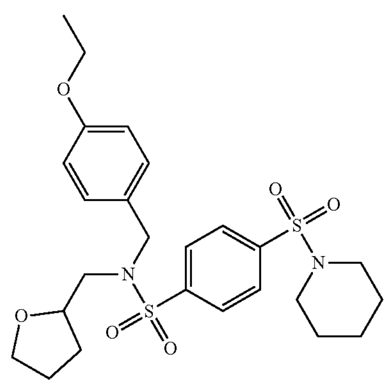 [SMILES: CCOc1ccc(CN(CC2CCCO2)S(=O)(=O)c2ccc(S(=O)(=O)N3CCCCC3)cc2)cc1] | N-(4-ethoxybenzyl)-4-(piperidin-1-ylsulfonyl)-N-((tetrahydrofuran-2-yl)methyl)benzenesulfonamide |
| 80 | 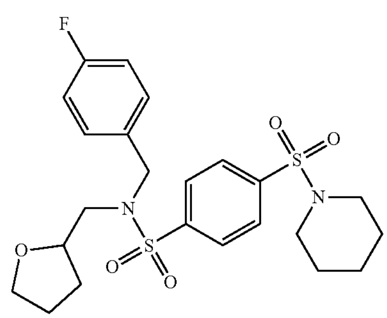 [SMILES: O=S(=O)(c1ccc(S(=O)(=O)N(Cc2ccc(F)cc2)CC2CCCO2)cc1)N1CCCCC1] | N-(4-fluorobenzyl)-4-(piperidin-1-ylsulfonyl)-N-((tetrahydrofuran-2-yl)methyl)benzenesulfonamide |

| No. | Structure | Nomenclature |
| --- | --- | --- |
| 81 | 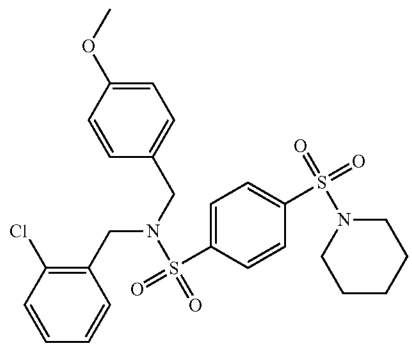 [SMILES: COc1ccc(CN(Cc2ccccc2Cl)S(=O)(=O)c2ccc(S(=O)(=O)N3CCCCC3)cc2)cc1] | N-(2-chlorobenzyl)-N-(4-methoxybenzyl)-4-(piperidin-1-ylsulfonyl)benzenesulfonamide |
| 82 | 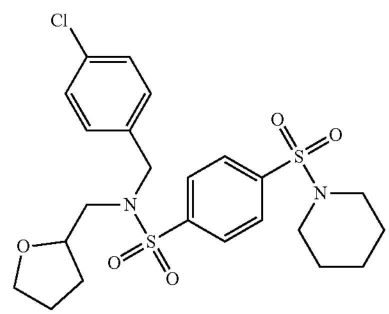 [SMILES: O=S(=O)(c1ccc(S(=O)(=O)N(Cc2ccc(Cl)cc2)CC2CCCO2)cc1)N1CCCCC1] | N-(4-chlorobenzyl)-4-(piperidin-1-ylsulfonyl)-N-((tetrahydrofuran-2-yl)methyl)benzenesulfonamide |
| 83 | 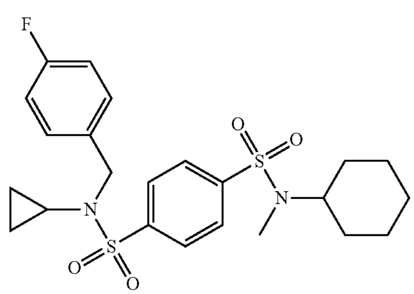 [SMILES: CN(C1CCCCC1)S(=O)(=O)c1ccc(S(=O)(=O)N(Cc2ccc(F)cc2)C2CC2)cc1] | N1-cyclohexyl-N4-cyclopropyl-N4-(4-fluorobenzyl)-N1-methylbenzene-1,4-disulfonamide |
| 84 | 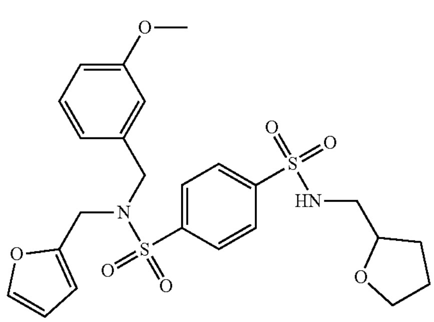 [SMILES: COc1cccc(CN(Cc2ccco2)S(=O)(=O)c2ccc(S(=O)(=O)NCC3CCCO3)cc2)c1] | N1-(furan-2-ylmethyl)-N1-(3-methoxybenzyl)-N4-((tetrahydrofuran-2-yl)methyl)benzene-1,4-disulfonamide |

| No. | Structure | Nomenclature |
|---|---|---|
| 85 | 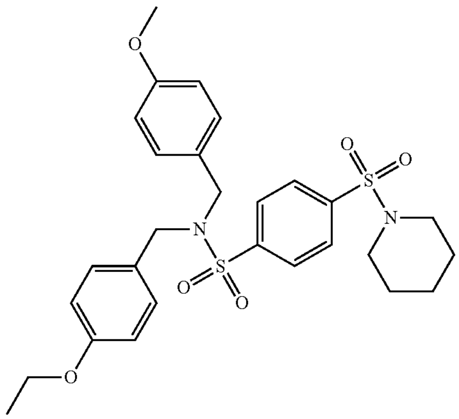 [SMILES: CCOc1ccc(CN(Cc2ccc(OC)cc2)S(=O)(=O)c2ccc(S(=O)(=O)N3CCCCC3)cc2)cc1] | N-(4-ethoxybenzyl)-N-(4-methoxybenzyl)-4-(piperidin-1-ylsulfonyl)benzenesulfonamide |
| 86 | 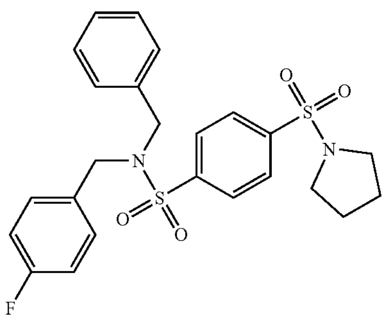 [SMILES: O=S(=O)(c1ccc(S(=O)(=O)N(Cc2ccccc2)Cc2ccc(F)cc2)cc1)N1CCCC1] | N-benzyl-N-(4-fluorobenzyl)-4-(pyrrolidin-1-ylsulfonyl)benzenesulfonamide |
| 87 | 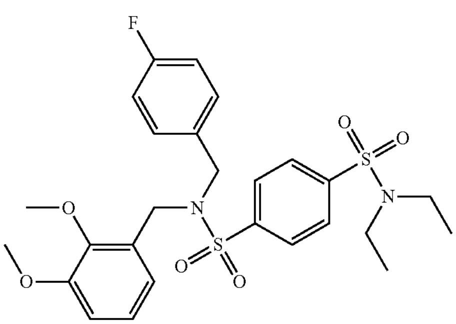 [SMILES: CCN(CC)S(=O)(=O)c1ccc(S(=O)(=O)N(Cc2ccc(F)cc2)Cc2cccc(OC)c2OC)cc1] | N1-(2,3-dimethoxybenzyl)-N4,N4-diethyl-N1-(4-fluorobenzyl)benzene-1,4-disulfonamide |
| 88 | 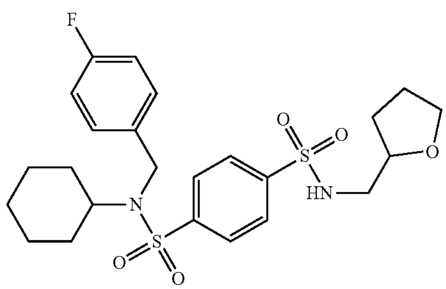 [SMILES: O=S(=O)(NCC1CCCO1)c1ccc(S(=O)(=O)N(Cc2ccc(F)cc2)C2CCCCC2)cc1] | N1-cyclohexyl-N1-(4-fluorobenzyl)-N4-((tetrahydrofuran-2-yl)methyl)benzene-1,4-disulfonamide |

-continued

| No. | Structure | Nomenclature |
|---|---|---|
| 89 | 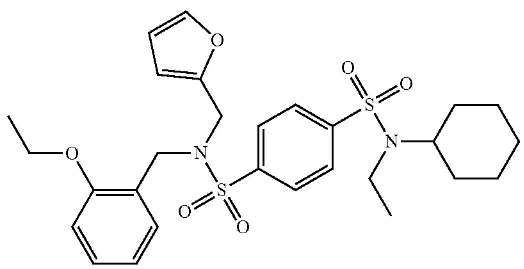 [SMILES: CCOc1ccccc1CN(Cc1ccco1)S(=O)(=O)c1ccc(S(=O)(=O)N(CC)C2CCCCC2)cc1] | N1-cyclohexyl-N4-(2-ethoxybenzyl)-N1-ethyl-N4-(furan-2-ylmethyl)benzene-1,4-disulfonamide |
| 90 | 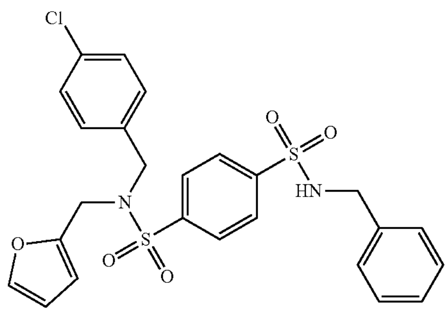 [SMILES: O=S(=O)(NCc1ccccc1)c1ccc(S(=O)(=O)N(Cc2ccc(Cl)cc2)Cc2ccco2)cc1] | N1-benzyl-N4-(4-chlorobenzyl)-N4-(furan-2-ylmethyl)benzene-1,4-disulfonamide |
| 91 | 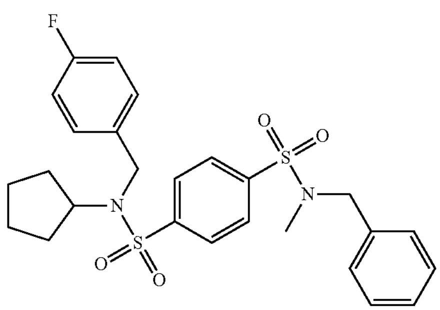 [SMILES: CN(Cc1ccccc1)S(=O)(=O)c1ccc(S(=O)(=O)N(Cc2ccc(F)cc2)C2CCCC2)cc1] | N1-benzyl-N4-cyclopentyl-N4-(4-fluorobenzyl)-N1-methylbenzene-1,4-disulfonamide |
| 92 | 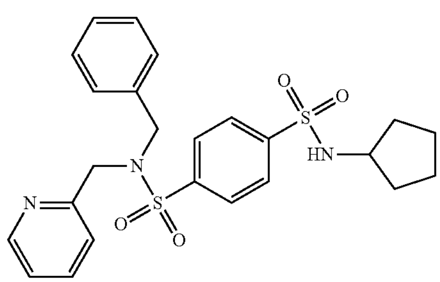 [SMILES: O=S(=O)(NC1CCCC1)c1ccc(S(=O)(=O)N(Cc2ccccc2)Cc2ccccn2)cc1] | N1-benzyl-N4-cyclopentyl-N1-(pyridin-2-ylmethyl)benzene-1,4-disulfonamide |
| 93 | 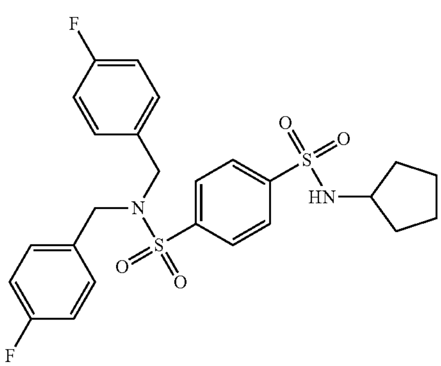 [SMILES: O=S(=O)(NC1CCCC1)c1ccc(S(=O)(=O)N(Cc2ccc(F)cc2)Cc2ccc(F)cc2)cc1] | N1-cyclopentyl-N4,N4-bis(4-fluorobenzyl)benzene-1,4-disulfonamide |

-continued

| No. | Structure | Nomenclature |
|---|---|---|
| 94 | 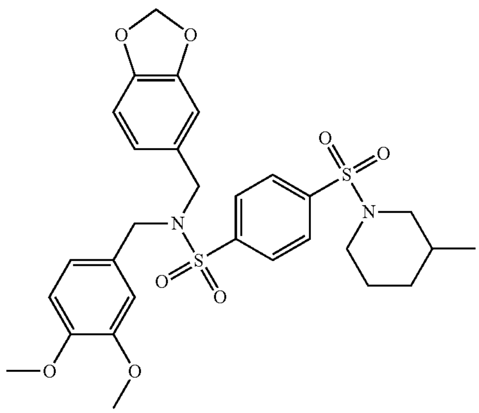 | N-(benzo[d][1,3]dioxol-5-ylmethyl)-N-(3,4-dimethoxybenzyl)-4-((3-methylpiperidin-1-yl)sulfonyl)benzenesulfonamide |
| 95 | 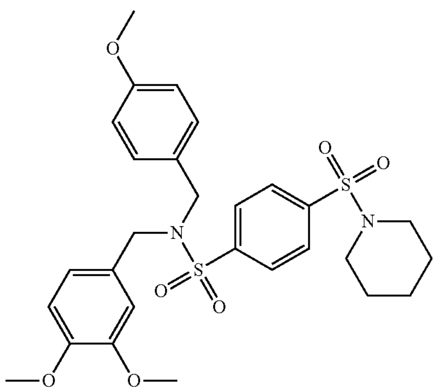 [SMILES: COc1ccc(CN(Cc2ccc(OC)c(OC)c2)S(=O)(=O)c2ccc(S(=O)(=O)N3CCCCC3)cc2)cc1] | N-(3,4-dimethoxybenzyl)-N-(4-methoxybenzyl)-4-(piperidin-1-ylsulfonyl)benzenesulfonamide |
| 96 | 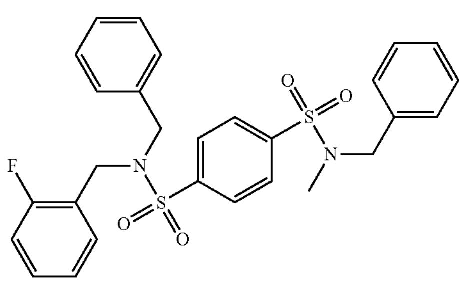 [SMILES: CN(Cc1ccccc1)S(=O)(=O)c1ccc(S(=O)(=O)N(Cc2ccccc2)Cc2ccccc2F)cc1] | N1,N4-dibenzyl-N1-(2-fluorobenzyl)-N4-methylbenzene-1,4-disulfonamide |
| 97 | 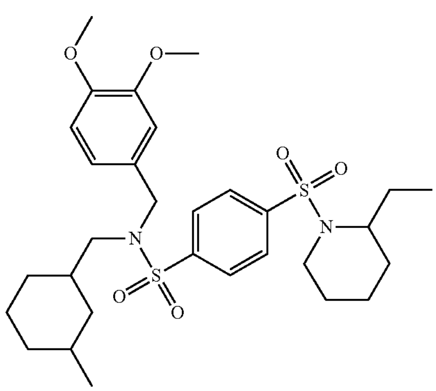 [SMILES: CCC1CCCCN1S(=O)(=O)c1ccc(S(=O)(=O)N(Cc2ccc(OC)c(OC)c2)CC2CCCC(C)C2)cc1] | N-(3,4-dimethoxybenzyl)-4-((2-ethylpiperidin-1-yl)sulfonyl)-N-(2-methylcyclohexyl)benzenesulfonamide |

| No. | Structure | Nomenclature |
|---|---|---|
| 98 | 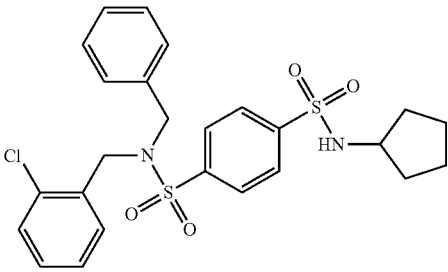 [SMILES: O=S(=O)(NC1CCCC1)c1ccc(S(=O)(=O)N(Cc2ccccc2)Cc2ccccc2Cl)cc1] | N1-benzyl-N1-(2-chlorobenzyl)-N4-cyclopentylbenzene-1,4-disulfonamide |
| 99 | 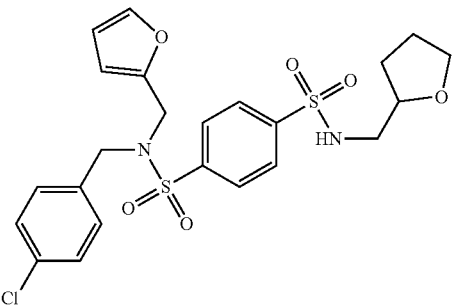 [SMILES: O=S(=O)(NCC1CCCO1)c1ccc(S(=O)(=O)N(Cc2ccc(Cl)cc2)Cc2ccco2)cc1] | N1-(4-chlorobenzyl)-N1-(furan-2-ylmethyl)-N4-((tetrahydrofuran-2-yl)methyl)benzene-1,4-disulfonamide |
| 100 | 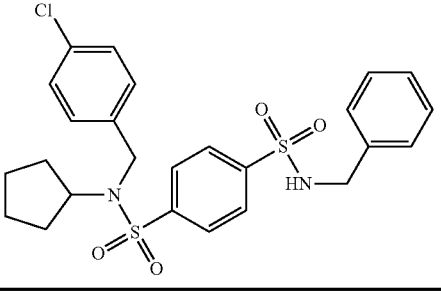 | N1-benzyl-N4-(4-chlorobenzyl)-N4-cyclopentylbenzene-1,4-disulfonamide |

B. Crystallization and Structure Determination

Compounds were dissolved in DMSO at final concentration of 50 mM. PDE6δ was mixed with 1:1 molar ratio of each compound at final concentration of 500 µM in buffer A. Crystallization conditions of all compound in complex with PDEδ are summarized in the Table 1. The crystals were directly fished out of the 96-well plates and flash frozen in a cryoprotectant solution that contains glycerol in addition to the mother. Diffraction datasets were collected at the X10SA beamline of the Suisse Light Source, Villigen. Data were processed by XDS and the structures were solved by molecular replacement using Molrep from CCP4 (suite). PDEδ from the PDEδ-farnesylated Rheb complex (PDB code: 3T5G) was used as a search model in the molecular replacement. Building of models and compounds was carried out using WinCoot and the refinement was done using REFMAC5. Refinement and data collection statistics of all structures are summarized in Table 2.

TABLE 1

Crystallization conditions of compounds in complex with PDEδ

| Compound | Qiagen Suite | Crystallization condition |
|---|---|---|
| 45 | Classics | 30% PEG 4000, 0.2M NaOAc, 0.1M TRIS-HCL, pH 8.5 |
| 44 | PEGs | 20% PEG 3350, 0.2M $Na_2SO_4$ |
| 16 | Protein Complex | 0.2M NaOAc, 0.1M Na3Cit, pH 5.5, 10% PEG 4000 |
| 21 | Core III | 1.4M NaOAc, 0.1M NaCAC, ph 6.8 |
| 22 | PEGs II | 0.1M NaOAc, pH 4.6, 30% PEG 4000, 0.2M $(NH_4)_2SO_4$ |

All crystals were grown at 293K.

TABLE 2

Data collection and refinement statistics for the structures of compounds (16, 21, 22, 44, 45) in complex with PDEδ

|  | Cpd 45 | Cpd 44 | Cpd 16 | Cpd 21 | Cpd 22 |
|---|---|---|---|---|---|
| Data collection |  |  |  |  |  |
| Space group | P 32 2 1 | P 32 2 1 | P 32 2 1 | P 32 2 1 | P 32 2 1 |
| Cell dimensions |  |  |  |  |  |
| a, b, c (Å) | 55.6, 55.6, 115.3 | 56.1, 56.1, 115.1 | 56.0, 56.0, 115.0 | 55.9, 55.9, 115.3 | 55.7, 55.7, 114.9 |
| α, β, γ (°) | 90.0, 90.0, 120.0 | 90.0, 90.0, 120.0 | 90.0, 90.0, 120.0 | 90.0, 90.0, 120.0 | 90.0, 90.0, 120.0 |
| Resolution (Å) | 27.83 (1.60) | 28.07 (2.60) | 44.07 (1.40) | 27.98 (2.40) | 27.88 (1.87) |
| $R_{sym}$ or $R_{merge}$ | 6.3 (44.5) | 14.0 (76.5) | 7.5 (64.9) | 16.1 (85.5) | 9.1 (34.9) |
| $I/\sigma(I)$ | 28.8 (7.5) | 20.4 (4.8) | 16.5 (3.4) | 17.1 (3.6) | 15.6 (5.2) |
| $CC_{1/2}$ | 100 (98.7) | 99.9 (95) | 99.8 (93.1) | 99.8 (90.0) | 99.9 (88.7) |
| Completeness (%) | 99.9 (99.8) | 99.9 (100) | 100 (100) | 99.9 (99.9) | 99.6 (94.5) |
| Redundancy | 19.1 (19.3) | 19.0 (20.3) | 9.6 (9.4) | 11.0 (11.1) | 8.2 (6.2) |
| Refinement |  |  |  |  |  |
| Resolution (Å) | 1.60 | 2.60 | 1.40 | 2.4 | 1.87 |
| No. reflections | 26598 | 6541 | 39854 | 8200 | 16799 |
| $R_{work}/R_{free}$ | 20.2/22.7 | 20.3/25.1 | 18.9/20.3 | 18.5/25.3 | 20.3/24.2 |
| No. atoms |  |  |  |  |  |
| Protein | 1173 | 1168 | 1224 | 1200 | 1178 |
| Ligand | 34 | 39 | 43 | 46 | 45 |
| Water | 131 | 29 | 180 | 63 | 101 |
| Bfactors |  |  |  |  |  |
| Protein | 23.2 | 40.2 | 19.7 | 27.9 | 25.8 |
| Ligand | 25.9 | 53.7 | 21.7 | 33.1 | 35.7 |
| Water | 35.1 | 51.1 | 33.4 | 30.4 | 32.8 |
| R.m.s. deviations |  |  |  |  |  |
| Bond lengths (Å) | 0.011 | 0.012 | 0.011 | 0.013 | 0.012 |
| Bond angles (°) | 1.55 | 1.39 | 1.66 | 1.46 | 1.35 |

C. Molecular Modeling

Molecular modeling experiments were carried out with the Maestro 9.1 suite (Schrödinger). Both ligand and receptor flexibility were taken into account by using receptor docking (Glide) in combination with the protein structure prediction embedded in the program Prime. Protein Preparation Wizard (Schrödinger Maestro suite) was used to prepare the PDEδ co-crystal for the calculations. Previously obtained X-ray structures were used to define the active site. Water molecules were removed from the protein crystal structure, hydrogen atoms were added and resulting structure was refined by OPLS2005 force-field. The minimization was ended when the RMSD reached 0.18 Å. Receptor Grid Preparation (Glide) was used to generate the protein grid that was subsequent utilized in docking experiments. The Van der Waals radius scaling factor was set to 0.5 with a partial charge cutoff of 0.25. Arg61 was selected as a possible site for hydrogen bonding. Additionally, docking runs were carried out using additional hydrogen bond constraints with Tyr149, Cys56, Gln78 and/or Glu88. Ligand preparation for docking was carried out with LigPrep in Maestro 9.1 and the OPLS_2005 force-field. Epika was used to generate possible states at target pH 7.0±4.0. Ligand docking options in Glide were used for the first round of docking experiments. Under Setting, XP (extra precision), Dock flexibly, Sample nitrogen inversions, Sample ring conformation and Epik state penalties to docking score were selected, amide bonds were penalized for nonplanar conformation. Under the Ligands section, the Van der Walls radius scaling factor was set to 0.5 and the docking was set to match at least 1 out of two constraints. Several high-score binding poses were generated and co-crystallized compounds were re-docked and analyzed in terms of overlay with the X-ray structure.

D. Biochemical Experiments

Example D.1: Alpha-Screen (*Nature* 2013, 497, 638)

Screening based on Alpha-technology was conducted in white, non-binding 1536-well plates (Corning) in a final volume of 6 μL. For the screen a mixture of $His_6$-PDEδ, and biotinylated K-Ras-peptide (final concentrations 100 nM and 250 nM in HEPES 20 mM, 100 mM NaCl, 0.005% Chaps, pH 7.5) were added to the 1536-well plates. Compound solutions were directly added from 10 mM DMSO stock solutions to a final concentration of 10 μM and the resulting mixture was incubated for 30 min (For dose-response curves, compounds were tested at concentrations between 10 μM and 5 nM). Premixed Nickel Chelate Acceptor Beads and Streptavidin Donor Beads were added to a final concentration of 10 μg/mL. The resulting mixture was incubated at 4° C. overnight. Plates were read on a Paradigm reader (Molecular devices, Alphascreen 1536 HTS detection cartridge, temperature 29° C.–33° C.).

Example D.2: Displacement Titrations of Labeled Atorvastatin-Probe for the Determination of $K_D$ Values Displacement Titrations of Labeled Atorvastatin-Probe for the Determination of $K_D$ Values:

Binding to PDEδ was validated and quantified by means of a displacement assay employing a fluorescent-tagged analog of the HMG-CoA reductase inhibitor Atorvastatin (Lipitor®) which has previously been shown to also bind to PDEδ. (*Nat. Chem. Biol.* 2011, 7, 375-383) The $K_D$ values were determined by the Fluorescence polarization competition binding assay previously developed by the inventors (*Nature* 2013, 497, 638).

Protein Purification

C-terminal histidine-tagged Arl2 and N-terminal histidine-tagged PDE5 were purified as described before (Fansa et al 2016 Natcomm). The purification was followed by size exclusion gel filtration on a Superdex 75 S26/60 column using buffer A (25 mM Tris-HCl, pH 7.5, 150 mM NaCl and 3 mM DTE).

The activity of the compounds was classified according to their $K_D$ values into the following ranges:

1 nM<$K_D$≤30 nM++++
30 nM<$K_D$≤100 nM+++
100 nM<$K_D$≤1000 nM++
$K_D$>1000 nM+

TABLE 3

$K_D$ values for compounds of general formula (I) as determined by means of fluorescence polarization assay

| Compound | $K_D$ [nM] |
|---|---|
| 1 | ++ |
| 2 | ++ |
| 3 | + |
| 4 | ++ |
| 5 | +++ |
| 6 | ++++ |
| 7 | ++++ |
| 8 | +++ |
| 9 | ++++ |
| 10 | ++++ |
| 11 | ++++ |
| 12 | ++++ |
| 13 | +++ |
| 14 | +++ |
| 15 | +++ |
| 16 | ++++ |
| 17 | +++ |
| 18 | ++ |
| 19 | ++++ |
| 20 | +++ |
| 21 | ++++ |
| 22 | ++++ |
| 23 | ++++ |
| 24 | +++ |
| 25 | ++ |
| 26 | ++++ |
| 27 | ++++ |
| 28 | ++ |
| 29 | ++ |
| 30 | ++ |
| 31 | +++ |
| 32 | +++ |
| 33 | ++ |
| 34 | +++ |
| 35 | +++ |
| 36 | +++ |
| 37 | +++ |
| 38 | ++ |
| 39 | +++ |
| 40 | ++ |
| 41 | + |
| 42 | ++ |
| 43 | ++ |
| 44 | ++++ |
| 45 | ++++ |
| 46 | ++ |
| 47 | +++ |
| 48 | ++++ |
| 49 | ++++ |
| 50 | +++ |
| 51 | ++ |
| 52 | ++ |
| 53 | ++ |
| 54 | ++ |
| 55 | ++++ |
| 56 | ++++ |
| 57 | ++ |
| 58 | +++ |
| 59 | ++ |
| 60 | ++ |
| 61 | ++++ |
| 62 | ++ |
| 63 | ++++ |
| 64 | ++ |
| 65 | ++++ |
| 66 | + |
| 67 | ++ |
| 68 | ++++ |
| 69 | ++ |
| 70 | ++ |
| 71 | + |
| 72 | ++ |
| 73 | ++ |
| 74 | + |
| 75 | + |
| 76 | ++ |
| 77 | ++ |
| 78 | ++ |
| 79 | + |
| 80 | +++ |
| 81 | +++ |
| 82 | ++ |
| 83 | +++ |
| 84 | ++++ |
| 85 | ++ |
| 86 | + |
| 87 | + |
| 88 | ++ |
| 89 | ++++ |
| 90 | ++ |
| 91 | +++ |
| 92 | ++++ |
| 93 | ++ |
| 94 | + |
| 95 | + |
| 96 | + |
| 97 | ++ |
| 98 | ++++ |
| 99 | ++ |
| 100 | +++ |

Example D.3: Cellular Thermal Shift Assay

General Appreciations:

Three biological replicates employing lysates from Jurkat cells were measured in which compound 22 was used at a concentration of 1 μM and alternatively with DMSO (1% v/v) treated samples as controls. The samples were split into 10 aliquots each and incubated at 10 different temperatures between 37 and 63.4° C. The precipitated fraction of the proteins was centrifuged off and the soluble fraction quantified relatively to the lowest temperature using a 10plex TMT label mass spectrometry based approach, i.e. thermal protein profiling (TPP) (M. M. Savitski, F. B. M. Reinhard, H. Franken, T. Werner, M. F. Savitski, D. Eberhard, D. Martinez Molina, R. Jafari, R. B. Dovega, S. Klaeger, et al., Science 2014, 346, 1255784; F. B. M. Reinhard, D. Eberhard, T. Werner, H. Franken, D. Childs, C. Doce, M. F. Savitski, W. Huber, M. Bantscheff, M. M. Savitski, et al., Nat. Methods 2015, 12, 1129-1131; H. Franken, T. Mathieson, D. Childs, G. M. A. Sweetman, T. Werner, I. Tögel, C. Doce, S. Gade, M. Bantscheff, G. Drewes, et al., Nat. Protoc. 2015, 10, 1567-93.)

Proteins were considered as stabilized or destabilized, respectively, when 1) they in all three replicates had a shift in melting points of at least ±2° C. (same direction) or when 2) in all three replicates they showed a difference in the relative peak intensities of at least 10% for the two highest temperatures. The shift of the melting point, i.e. the inflection point of the melting curve, has been used repeatedly in previous studies as decisive parameter (1-3). The second parameter was used as an alternative since orientating experiments had shown an atypical melting behavior upon binding of ligand 22 to proteins in some cases (see below). In total, we identified 5492 proteins of which 2872 were identified with at least two unique peptides in all replicates (compound treated and DMSO controls). 2186 of these proteins showed a normal melting curve in the DMSO control, i.e. they had relative intensities of the labels of the two highest temperatures of smaller or equal to 35% of the labels of the lowest temperatures. Out of the 5492 proteins only PDEδ and RPL31 (Ribosomal Protein L31) could be identified as hits according to the definition above. RPL31 showed a typical melting behavior in the DMSO controls and in the compound treated samples with a shift in melting temperature of +3±0.4° C. (see FIG. 4A). PDEδ showed a typical melting behavior only in the DMSO controls. In the compound treated samples the percentage of soluble protein at high temperatures (59.6° C. and 63.4° C.) was much higher, resulting in 26-28% higher signal intensities compared to DMSO controls (see FIG. 4B), i.e. the stabilization of PDEδ by compound 22 leads to an incomplete precipitation of the protein at higher temperatures.

Cultivation and Harvest of Cells, Cell Lysis

Jurkat cells were cultivated until a cell density of 1.5-2.0*10$^6$ was reached. 50 ml of cell suspension were transferred into a falcon tube and incubated on ice for 2 min followed by centrifugation at 350×g at room temperature for 3 min. The supernatant was discarded and the pellet re-suspended in 25 ml ice cold phosphate buffered saline (PBS). The cells were harvested by centrifugation at 350×g at room temperature for 2 min and the supernatant discarded again. This washing procedure was repeated twice (first using 25 ml PBS, second just 10 ml PBS). After the last washing and centrifugation step the cells were re-suspended in 1.5 ml PBS and quick frozen in liquid nitrogen. Cell lysis was performed via thaw/freeze cycles. Therefore, frozen cells were thawed at 23° C. until about 60-80% of the cells are unfrozen and kept on ice until the whole sample was thawed. After that, cells were quick frozen with liquid nitrogen again and the cycle was repeated 4 times. Afterwards, the cell lysate was centrifuged for 20 min at 100.000×g at 4° C. in an ultracentrifuge. The resulting supernatant was gently transferred into a new tube, quick frozen with liquid nitrogen and stored at −80° C. until further usage Thermal Shift Before the thermal shift the protein concentration was determined by e.g. using the Bradford method. Samples were diluted with PBS to a final protein concentration of around 4 mg/ml. Samples were divided into two aliquots a 1.4 ml. One of the aliquots was incubated with 14 µl of compound 22 solution (1 µmol/l in DMSO) the other aliquots with 14 µl of DMSO for 10 min at room temperature. Each of the aliquots was divided into 10 new aliquots with 100 µl each which were incubated at the following temperatures for 3 min (Aliquot 1: 36.9° C., 2: 40.1° C., 3: 44.1° C., 4: 47.9° C., 5: 51.0° C., 6: 54.4° C., 7: 58° C., 8: 61.3° C., 9: 64.5° C., 10: 67° C.). Afterwards samples were allowed to cool for 5 min to room temperature and centrifuged for 20 min at 100.000×g at 4° C. in an ultracentrifuge.

Mass Spectrometry Based Readout

For the mass spectrometry based readout samples were reduced, alkylated, precipitated with acetone and tryptic digested. After that each aliquot was labeled using TMT reagents according to the temperature used during the thermal shift procedure. For reduction, to each 75 µl aliquot resulting from the thermal shift procedure 7.5 µl of 200 mM TCEP (Tris(2-carboxyethyl)phosphine) solution (prepared from 140 µl of 0.5 M TCEP, 140 µl H$_2$O and 70 µl 1 M TEAB (Triethylammonium bicarbonate buffer)) were added, mixed by inversion, shortly centrifuged at 10.000×g and incubated at 55° C. for 1 h in a thermo block. To alkylate 7.5 µl of freshly prepared 375 mM iodoacetamide solution (26 mg iodoacetamide dissolved in 375 µl of 200 mM TEAB buffer) were added to each sample and incubated for 30 minutes in the dark at room temperature. For precipitation of proteins six volumes of pre-chilled (−20° C.) acetone were added and incubated at −20° C. overnight. Afterwards samples were centrifuged for 10 min at 8000 g at 4° C. and the supernatants were disposed. The pellets were dried for about 30 to 45 min at room temperature and then re-suspended in 107.5 µl of trypsin solution (165 µl of a trypsin solution of 100 µg in 250 ml of 10 mM HCl diluted in 2200 µl of 100 mM TEAB buffer). Samples were vortexed for about 20 s and shortly centrifuged to gather the suspension at the bottom to the tube, followed by incubation at 37° C. for 2-3 hours. Vortexing and centrifugation were repeated and samples were incubated at 37° C. overnight. At the next day, samples were spinned down and labeled with TMT label according to the description of the manufacturer, but using just half the amount of labeling reagent. Briefly, 82 µl of anhydrous acetonitrile were added to each 0.8 mg of TMT label reagent aliquot (TMT10plex, #90110 ThermoFisher Scientific). 41 µl of the respective TMT reagent solution were transferred to the peptide sample of the respective DMSO control (V1-10). Directly after addition, samples were briefly vortexed. For the other samples (compound treated) 100 µl were transferred to the respective remaining TMT reagent. Directly after addition samples are briefly vortexed. Samples were incubated for 2 h at room temperature. Afterwards, 8 µl of 5% hydroxylamine were added to the samples and samples were incubated for 15 min to quench the reaction. After that 120 µl of each labeled aliquot incubated with compound 22 were combined into one sample and 120 µl of each labeled aliquots incubated with DMSO were combined to a second one. Both samples were evaporated in a Speedvac device at 30° C. until a dry white pellet remains.

Prior to nanoHPLC-MS/MS analysis samples were fractionated into 10 fractions on a C18 column using high pH conditions to reduce the complexity of the samples and thereby increasing the number of quantified proteins. Therefore, both samples were dissolved in 120 µl 20 mM ammonium formate (NH$_4$COO) at pH 11 each, followed by incubation in an ultra-sonicator for about 2 min and subsequently vortexing for 1 min and centrifugation at 13.000 rpm for 3 min at room temperature. 50 µl of supernatant were injected onto an XBridge C18 column (130 Å, 3.5 µm, 1 mm×150 mm) using a U3000 capHPLC-System (ThermoFisher scientific, Germany). Separation was performed at a flow rate of 50 µl/min using 20 mM NH$_4$COO pH 11 in water as solvent A and 40% 20 mM NH$_4$COO pH 11 in water premixed with 60% acetonitrile as solvent B. Separation conditions were 95% solvent A/5% solvent B isocratic for the first 15 min, to desalt the samples, followed by a linear gradient up to 25% in 5 min and a second linear gradient up to 100% solvent B in 60 min (80 min separation time in total). Afterwards the column was washed at 100% solvent B for 20 min and re-equilibrated to starting conditions. Detection was carried out at a valve length of 214 nm. The eluate between 10 and 80 min was fractionated into 10 fractions (1$^{st}$ fraction 20 min, 2$^{nd}$ fraction 10 min, 3$^{rd}$-8$^{th}$ fraction 5 min each, 9$^{th}$ fraction 10 min, 10$^{th}$ fraction 25 min). Each fraction was dried in a SpeedVac at 30° C. until complete dryness and subsequently subjected to nanoHPLC-MS/MS analysis.

For nanoHPLC-MS/MS analysis samples were dissolved in 10 µl of 0.1% TFA in water and 4 µl were injected onto a UltiMate™ 3000 RSLCnano system (ThermoFisher scientific, Germany) online coupled to a Q Exactive™ Plus Hybrid Quadrupole-Orbitrap Mass Spectrometer equipped with a nano-spray source (Nanospray Flex Ion Source, Thermo Scientific). All solvents were LC-MS grade. For desalting the samples were injected onto a pre-column cartridge (5 µm, 100 Å, 300 µm ID*5 mm, Dionex, Germany) using 0.1% TFA in water as eluent with a flow rate of 30 µL/min. Desalting was performed for 5 min with eluent flow to waste followed by back-flushing of the sample during the whole analysis from the pre-column to the PepMap100 RSLC C18 nano-HPLC column (2 µm, 100 Å, 75 µm ID×25 cm, nanoViper, Dionex, Germany) using a linear gradient starting with 95% solvent A (water containing 0.1% formic acid)/5% solvent B (acetonitrile containing 0.1% formic acid) and increasing to 60% solvent A 0.1% formic acid/40% solvent B after 125 min using a flow rate of 300 nL/min. Afterwards the column was washed (95% solvent B as highest acetonitrile concentration) and re-equilibrated to starting conditions.

The nano-HPLC was online coupled to the Quadrupole-Orbitrap Mass Spectrometer using a standard coated Silica-Tip (ID 20 µm, Tip-ID 10 µM, New Objective, Woburn, Mass., USA). Mass range of m/z 300 to 1650 was acquired with a resolution of 70000 for full scan, followed by up to ten high energy collision dissociation (HCD) MS/MS scans of the most intense at least doubly charged ions using a resolution of 35000 and a NCE energy of 35%.

Data evaluation was performed using MaxQuant software[7] (v.1.5.3.30) including the Andromeda search algorithm and searching the human reference proteome of the Uniprot database. The search was performed for full enzymatic trypsin cleavages allowing two miscleavages. For protein modifications carbamidomethylation was chosen as fixed and oxidation of methionine and acetylation of the N-terminus as variable modifications. For relative quantification the type "reporter ion MS2" was chosen and for all lysines and peptide N-termini 10plex TMT labels were defined. The mass accuracy for full mass spectra was set to 20 ppm (first search) and 4.5 ppm (second search), respectively and for MS/MS spectra to 20 ppm. The false discovery rates for peptide and protein identification were set to 1%. Only proteins for which at least two peptides were quantified were chosen for further validation. Relative quantification of proteins was carried out using the reporter ion MS2 algorithm implemented in MaxQuant. All experiments were performed in biological triplicates.

Melting Curves Calculation

To determine the melting point shifts between compound 22 and DMSO treated samples of each protein an in-house developed Excel-Macro was used. Briefly, denaturation changes at different temperatures were tracked by the reporter ion intensity and observed in relation to the lowest temperature; therefore, the lowest temperature got the value 1.

The relative fold changes were calculated as a function of temperature. The measuring points showed a sigmoidal trend, which were fitted with the following equation using an iterative working macro for Microsoft Excel.

$$y = \text{bottom plateau} + \frac{(\text{top plateau} - \text{bottom plateau})}{1 + e^{-(\frac{a}{Temp})-b}}$$

Top plateau is fixed to one, Temp is the temperature, bottom plateau is a protein specific constant that defines the maximal denaturation and a and b are constants which describe the curve progression.

The melting point of a protein is defined as the temperature at which half of the protein has been denatured. This point aligns with the inflection point of the curve.

The inflection point shows the highest slope of the curve which is defined as the value of the first derivation.

For hit identification following requirements were defined and had to be fulfilled for all replicates: (1) the protein has to be identified with at least two unique peptides, (2) the DMSO control has to melt nicely, i.e. the TMT labels of the two highest temperatures have to have a relative intensity of smaller or equal of 35% of the label of the highest temperature, (3a) the shift of the melting point has to be at least 2° C. in the same direction, i.e. all stabilized or all destabilized, and/or (3b) the difference in the relative peak intensities of DMSO control compared to compound treated is at least 10% for the two highest temperatures.

Example D.4: Real Time Proliferation and FILM Assays

Cell Culture

Panc-TU-1, MiaPaCa-2, PANC-1 and BxPC-3 cell lines were cultured in DMEM supplemented with 10% fetal calf serum, 1% L-glutamine (PAN-Biotech) and 1% non-essential amino acids (PAN-Biotech). The cells were maintained in a humidified incubator at 37° C. and 5% CO2. For microscopy, cells were seeded in four-well Lab-Tek chambers (Thermo Scientific) in DMEM without phenol red, supplemented with 25 mM HEPES. Transfection was performed with either Effectene (Qiagen) or Lipofectamine 2000 (Invitrogen).

HCT-116, Hke3, Hkh2, DiFi and SW480 cell lines are maintained in DMEM (Dulbecco's modified Eagle medium, Sigma-Aldrich Biochemie GmbH, Taufkirchen, Germany) supplemented with 10% FCS (fetal calf serum), 2 mM L-glutamine (Sigma-Aldrich Biochemie GmbH, Taufkirchen, Germany), and 1% non-essential amino acids (NEAA; Sigma-Aldrich Biochemie GmbH, Taufkirchen, Germany), at 37° C. and 5% CO2 in a humidified incubator.

HT29 cells (ATCC, American Type Culture Collection, Manssas, Va., USA) are maintained in Ham's medium, supplemented with 10% FCS (fetal calf serum) and 1 mM L-glutamine (Sigma-Aldrich Biochemie GmbH, Taufkirchen, Germany), at 37° C. and 5% $CO_2$ in a humidified incubator.

TABLE A

Overview of colorectal cancer cell lines used

| Cell line | KRas status | other onc. mutations |
|---|---|---|
| SW480 | G12V//G12V | |
| HCT-116 | G13D//wt | |
| Hke3 | G13D//wt | |
| Hkh2 | —//wt | |
| HT29 | wt//wt | BRaf (V600E) |
| DiFi | wt//wt | EGFR overexpression |

Real Time Cell Analysis (RTCA)

RTCA measurements of Panc-TU-1, MiaPaCa-2, PANG-1 and BxPC-3 cell lines were performed on a Dual Plate xCELLigence instrument (Roche Applied Science, Indianapolis, Ind.). This device measures a dimensionless cell index which is based on impedance. Depending on the cell line $5 \times 10^3$-$7.5 \times 10^3$ cells were seeded in each well of 16-well E-plate. After seeding, cells were allowed to settle for 15 min at room temperature before insertion into the xCELLigence instrument in a humidified incubator at 37° C. with 5% $CO_2$. The cells were treated with the small-molecule inhibitors compound 16 (Deltasonamide 1) or compound 19 (Deltasonamide 2) after a growth period of approximately 24 h. The amount of DMSO was kept constant between the distinct inhibitor dilutions and did not exceed an amount of 0.2%. The impedance was measured in 15 min intervals for up to 100 h. Assays were performed in triplicates, each containing two technical duplicates. The cell index was normalized to 1 at the time point of drug administration. To display the inhibitor-dose growth-response relationships of the sulfonamide inhibitors, the area below the curves were integrated over 60 h starting at the administration time point and normalized to the DMSO control. (FIG. 5A-E).

RTCA measurements of HT29, HCT-116, Hke3, Hkh2, DiFi and SW480 cell lines were performed using 16-well E-plates on a Dual Plate xCELLigence instrument (Roche Applied Science, Indianapolis, Ind.) in a humidified incubator at 37° C. with 5% $CO_2$. This device measures the impedance-based cell index (CI), Continuous impedance measurements are monitored every 15 min for up to 300 hours. Blank measurements are performed with growth medium. Depending on the cell line $1 \times 10^4$-$2 \times 10^4$ cells are plated in each well of 16-well E-plate for short-term measurements and $0.75$-$2 \times 10^3$ cells/well for long-term measurements. After seeding, cells were allowed to reach steady growth for 24 h before inhibitor administration, whereas in case of cells stably expressing the inducible shRNA transgene, doxycline is directly applied to the wells of interest. In case of dose-dependent inhibitor measurements, the amount of DMSO is kept constant between the individual conditions and did not exceed 0.24%. Cell indices are normalized to the time point of drug administration. For shRNA experiments no normalization is applied. (FIG. 6A-G).

Confocal Microscopy

Confocal images were acquired with a confocal laser-scanning microscope (FV1000, Olympus). For detection of mCitrine-RheB and mCitrine-KRas, the sample was excited using the 488 nm wavelength of an argon laser. Fluorescence signal was collected through an oil immersion objective (×60/1.35 UPlanSApo, Olympus) and spectrally filtered by a band pass filter from 500 nm to 550 nm. For detection of mCherry-PDEδ, a 561 nm diode laser was used for excitation. The fluorescence emission was spectrally filtered by a band pass filter from 600 to 700 nm.

Fluorescence Lifetime Imaging Microscopy (FLIM)

Fluorescence lifetime images were acquired using a confocal laser-scanning microscope (FV1000, Olympus) equipped with a time-correlated single-photon counting module (LSM Upgrade Kit, Picoquant). For detection of the donor (mCitrine), the sample was excited using a 507-nm diode laser (Picoquant) at a 40-MHz repetition frequency. Fluorescence signal was collected through an oil immersion objective (×60/1.35 UPlanSApo, Olympus) and spectrally filtered using a narrow-band emission filter (HQ 530/11, Chroma). Photons were detected using a single-photon counting avalanche photodiode (PDM Series, MPD) and timed using a single-photon counting module (PicoHarp 300, Picoquant).

FLIM Data Analysis

Intensity thresholds were applied to segment the cells from the background fluorescence. Data were further analyzed via global analysis (H. E. Grecco, P. Roda-Navarro, A. Girod, J. Hou, T. Frahm, D. C. Truxius, R. Pepperkok, A. Squire, P. I. H. Bastiaens, Nat. Methods 2010, 7, 467-472.) to obtain the molecular fraction α of interacting mCitrine-RheB and mCherry-PDEδ. Furthermore, the resulting α-maps were multiplied pixel-wise with the FLIM intensity image and divided by the average intensity to calculate intensity-weighted α values. Resulting α-maps were binned by factor two to reduce background noise. Dependence of α on the inhibitor concentration was determined through sequential addition of compound 16 (Deltasonamide 1) or compound 19 (Deltasonamide 2) followed by incubation periods of 10 min before FLIM data acquisition. Dose-response relationships were calculated by plotting obtained α per concentration of the respective compound, using the equation:

$$\alpha = A_0 - \frac{A \times [X]}{[X] + KD}$$

where $A_0$ is α in absence of the inhibitor, A an asymptotic offset and [X] the concentration of inhibitor in the medium. $A_0$ was normalized to 0.2. (FIGS. 4 A and B)

KRas Localization Analysis

Confocal images of cells were segmented into plasma membrane and cytoplasm whereby the plasma membrane segment contained one third of all pixels. The mean intensity of plasma membrane and cytoplasm were normalized to the total mean intensity of each cell at each time point (FIG. 4C).

Example D.5: Permeability Assay

Caco-2 Permeability Assay:

Compounds from a 10 mM DMSO stock were diluted to a final concentration of 10 µM in HBSS buffer ph 7.4 and incubated for 2 hours at 37° C. and 5% CO2 on a monolayer of Caco-2 cells that had been grown on a transwell membrane for 21 days. The compound concentration was measured in the receiver as well as the donor well. Apparent permeability (Papp) from either the apical to basolateral direction or vice versa was calculated by the equation: Papp=1/AC0 (dQ/dt), where A is the membrane surface area, C0 is the donor drug concentration at t=0, and dQ/dt is the amount of drug transported within the given time period of 2 hours.

The apparent permeability ($P_{aap}$) values measured from the apical (A) to the basolateral (B) side of Caco-2 cells indicate that both compound 16 (Deltasonamide 1) and compound 19 (Deltasonamide 2) are slowly migrating compounds comparable to the low permeability of Deltarasin. Moreover, while compound 16 (Deltasonamide 1), Deltarasin and to a lesser extent compound 19 (Deltasonamide 2) show enhanced apparent permeability from the B to A side suggesting the putative interaction of the compounds with efflux transpoerters, this effect is only moderate. In contrast, Deltazinone 1, that is devoid of ionizalbe amines, shows good apparent permeability in both directions.

TABLE 4

| Compound | Caco-2 pH 6.5/7.4 $P_{app}$ A→B [$10^{-6}$ cm/s] Arith. Mean | Caco-2 pH 6.5/7.4 $P_{app}$ B→A [$10^{-6}$ cm/s] Arith. Mean | Caco-2 pH 6.5/7.4 Ratio B→A:A→B [NA] Arith. Mean |
|---|---|---|---|
| 44 | 0.6 | 0.6 | 0.9 |
| 16 | 1.6 | 13.7 | 8.8 |
| 19 | 0.9 | 2.7 | 2.9 |
| 21 | 0.4 | 0.5 | 1.1 |
| 22 | 0.9 | 0.6 | 0.6 |
| Deltarasin | 1.0 | 5.1 | 5.0 |
| Deltazinone 1 | 41.1 | 25.1 | 0.6 |

Log P/Log D Calculations:

ACD/Percepta was used to calculate log P and log D (pH 7.4). Log P values of compound 16 and 19 are similar to that fo Deltazinone 1, but markedly lower than that of Deltarasin. Most importantly, as expected compounds 16 (Deltasonamide 1) and 19 (Deltasonamide 2) showed a calculated log D at neutral pH lower than that of Deltarasine and Deltazinonel. This is consistent with a less effective membrane drug penetration of compounds 16 and 19, in comparison to the previously reported more lipophilic chemotypes.

TABLE 5

| Compound | logP | logD (pH = 7.4) |
|---|---|---|
| 16 | 5.17 | 2.48 |
| 19 | 4.81 | 2.12 |
| Deltarasin | 8.18 | 5.45 |
| Deltazinone 1 | 4.27 | 4.27 |

Example D.6: SRB Viability/Cytotoxicity Assay

Cells were incubated with test substances at titrated concentrations ranging between 30 µM and 1.7 nM for 72 h. After the incubation period, the cells were fixed with 10% (wt/vol) trichloroacetic acid and stained for 30 min with sulforhodamine B (SRB) staining solution prior to removing unbound dye by washing repeatedly with 1% (vol/vol) acetic acid. The protein-bound dye is dissolved in 10 mM Tris base solution for OD (optical density) determination at 510 nm using a microplate reader.

Example D.7: Apoptosis Assay

Apoptosis assays are performed on a LSR II flow cytometer (BD Bio-science). For this, cells are seeded in 6-well plates with an amount of $2 \times 10^5$ cells per well. Cells are treated with different concentrations of compound 19 (Deltasonamide 2) for 24 h. DMSO is used as a control. Subsequently, the supernatant is collected in FACS vials and the cells are washed with 1 mL PBS. Afterwards, cells are detached with 0.5 mL Accutase™ (EMD Millipore Corporation). The detached cells are resuspended in 1 mL PBS and transferred to the respective FACS vials. The vials are centrifuged at 200 g for 5 min. The supernatant is discarded and the cells are washed twice with PBS. Cell pellets are re-suspended in 100 µL PBS containing 5 µL of 7-AAD. Samples are vortexed and incubated in the dark at RT for 15 min. Afterwards, 200 µL PBS are added and the samples are transferred to fresh FACS vials through filter lids. The samples are measured within one hour after transfer using 488 nm as excitation wave length and the emission filter 695/40. The measurements are acquired and gated with the BD FACSDiva™ software.

The results are shown in FIG. 7.

What is claimed is:

1. A compound of the formula (I):

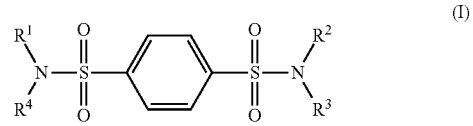

wherein $R^1$ represents —$CH_2R^5$;

$R^2$ represents —$CH_2$—$R^6$;

$R^3$ represents —$R^7$, —$CH_2$—$R^7$, or —$CH_2$—$CH_2$—$R^7$, $R^4$ represents —$R^8$, —$CH_2$—$R^8$, or —$CH_2$—$CH_2$—$R^8$;

$R^5$ represents

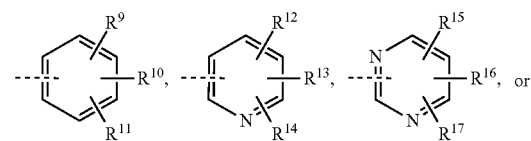

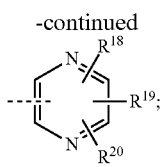

R⁶ represents

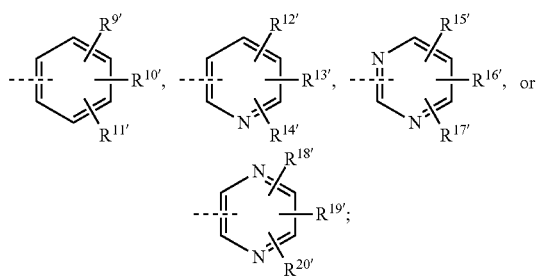

R⁷ represents

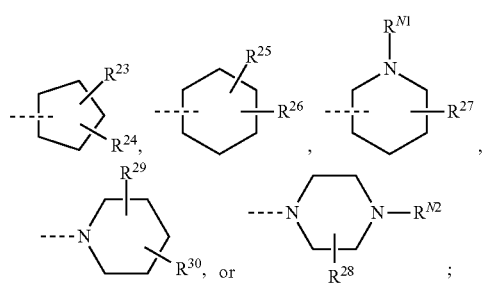

R⁸ represents

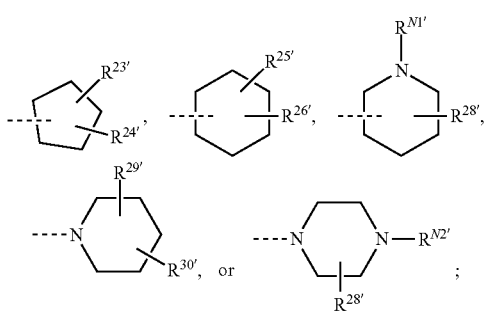

R⁹-R²⁰ and R⁹'-R²⁰' represent independently of each other
—H, —F, —Cl, —Br, —I, —OH, —CN, —NO₂, —CH₃, —C₂H₅, —C₃H₇, —CH(CH₃)₂, —C₄H₉, —CH₂—CH(CH₃)₂, —CH(CH₃)—C₂H₅, —C(CH₃)₃, -cyclo-C₃H₅, —CH₂-cyclo-C₃H₅, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, —OCH₃, —OC₂H₅, —OC₃H₇, —OCH(CH₃)₂, —OC(CH₃)₃, —OC₄H₉, —OCHF₂, —OCF₃, —OCH₂CF₃, —OC₂F₅, —OCH₂OCH₃, —O-cyclo-C₃H₅, —OCH₂-cyclo-C₃H₅, —O—C₂H₄-cyclo-C₃H₅, —CHO, —COCH₃, —COCF₃, —COC₂H₅, —COC₃H₇, —COCH(CH₃)₂, —COC(CH₃)₃, —COOH, —COOCH₃, —COOC₂H₅, —COOC₃H₇, —COOCH(CH₃)₂, —COOC(CH₃)₃, —OOC—CH₃, —OOC—CF₃, —OOC—C₂H₅, —OOC—C₃H₇, —OOC—CH(CH₃)₂, —OOC—C(CH₃)₃, —NH₂, —NHCH₃, —NHC₂H₅, —NHC₃H₇, —NHCH(CH₃)₂, —NHC(CH₃)₃, —N(CH₃)₂, —N(C₂H₅)₂, —N(C₃H₇)₂, —N[CH(CH₃)₂]₂, —N[C(CH₃)₃]₂, —CH₂NH₂, —CH₂NHCH₃, —CH₂NHC₂H₅, —CH₂N(CH₃)₂, —CH₂N(C₂H₅)₂, —NHCOCH₃, —NHCOCF₃, —NHCOC₂H₅, —NHCOC₃H₇, —NHCOCH(CH₃)₂, —NHCOC(CH₃)₃, —CONH₂, —CONHCH₃, —CONHC₂H₅, —CONHC₃H₇, —CONHCH(CH₃)₂, —CONH-cyclo-C₃H₅, —CONHC(CH₃)₃, —CON(CH₃)₂, —CON(C₂H₅)₂, —CON(C₃H₇)₂, —CON[CH(CH₃)₂]₂, —CON[C(CH₃)₃]₂, —SO₂NH₂, —SO₂NHCH₃, —SO₂NHC₂H₅, —SO₂NHC₃H₇, —SO₂NHCH(CH₃)₂, —SO₂NH-cyclo-C₃H₅, —SO₂NHC(CH₃)₃, —SO₂N(CH₃)₂, —SO₂N(C₂H₅)₂, —SO₂N(C₃H₇)₂, —SO₂N[CH(CH₃)₂]₂, —SO₂N[C(CH₃)₃]₂, —NHSO₂CH₃, —NHSO₂CF₃, —NHSO₂C₂H₅, —NHSO₂C₃H₇, —NHSO₂CH(CH₃)₂, —NHSO₂C(CH₃)₃, —CH=CH₂, —CH₂—CH=CH₂, —C(CH₃)=CH₂, —CH=CH—CH₃, —C≡CH, —C≡C—CH₃, —CH₂—C≡CH, -Ph, —O-Ph, —O—CH₂-Ph, —OSi(CH₃)₃, —OSi(C₂H₅)₃, —OSi(CH₃)₂C(CH₃)₃,

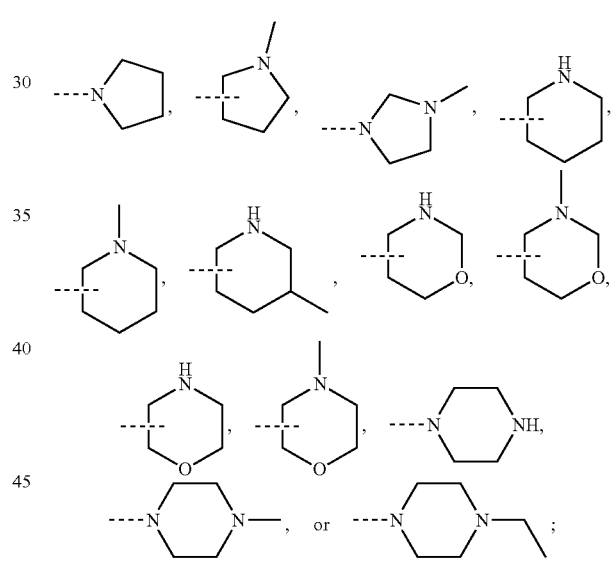

R²³-R³⁰, R²³'-R²⁶' and R²⁸'-R³⁰' represent independently of each other
—H, —F, —Cl, —OH, —CN, —NO₂, —CH₃, —C₂H₅, —C₃H₇, —CH(CH₃)₂, —CF₃, —OCH₃, —OC₂H₅, —OC₃H₇, —OCH(CH₃)₂, —OCF₃, —OCH₂OCH₃, —O-cyclo-C₃H₅, —OCH₂-cyclo-C₃H₅, —COOCH₃, —COOC₂H₅, —OOC—CH₃, —OOC—CF₃, —OOC—C₂H₅, —OOC—C(CH₃)₃, —NH₂, —NHCH₃, —NHC₂H₅, —NHCH(CH₃)₂, —N(CH₃)₂, —N(C₂H₅)₂, —CH₂NH₂, —CH₂NHCH₃, —CH₂NHC₂H₅, —CH₂N(CH₃)₂, —CH₂N(C₂H₅)₂, —NHCOCH₃, —NHCOCF₃, —CONH₂, —CONHCH₃, —CONHC₂H₅, —CON(CH₃)₂, —CON(C₂H₅)₂, —SO₂NH₂, —SO₂NHCH₃, —SO₂NHC₂H₅, —SO₂N(CH₃)₂, —SO₂N(C₂H₅)₂, —NHSO₂CH₃, —NHSO₂CF₃, or —NHSO₂C₂H₅;

R^{N1}, R^{N1'}, R^{N2}, and R^{N2"} represent independently of each other

—H, —CH₃, —C₂H₅, —C₃H₇, —CH(CH₃)₂, -cyclo-C₃H₅, —COCH₃, —COCF₃, —COC(CH₃)₃, —OOC—CH₃, —OOC—CF₃, —OOC—C₂H₅, —OOC—C(CH₃)₃, —SO₂CH₃, or —SO₂CF₃;
or pharmaceutically acceptable salts thereof.

2. The compound according to claim 1, wherein
R⁵ is

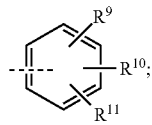

R⁶ is

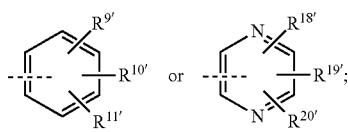

and
R⁹-R¹¹, R⁹'-R¹¹' and R¹⁸'-R²⁰' have the same meanings as defined in claim 1.

3. The compound according to claim 1, wherein
R⁵ is

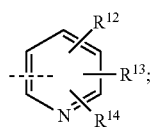

R⁶ is

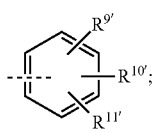

and
R¹²-R¹⁴ and R¹⁵-R¹⁷ have the same meanings as defined in claim 1.

4. The compound according to claim 1, wherein
R⁵ is

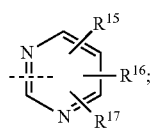

R⁶ is

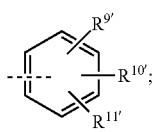

and
R⁹'-R¹¹' and R¹⁵-R¹⁷ have the same meanings as defined in claim 1.

5. The compound according to claim 1, wherein
R⁵ is

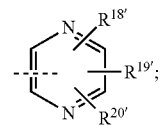

R⁶ is

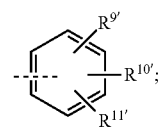

and
R⁹'-R¹¹' and R¹⁸-R²⁰ have the same meanings as defined in claim 1.

6. The compound according to claim 1, wherein
R³ is —R⁷, or —CH₂—R⁷; R⁴ is —R⁸;
R⁷ is

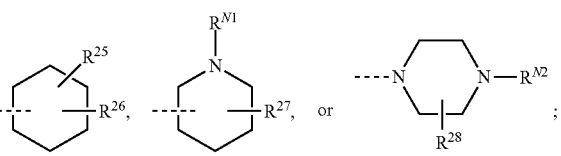

R⁸ is

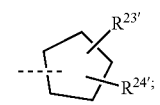

and
R²³'-R²⁴', R²⁵-R²⁸ and R^{N1}-R^{N2} have the same meanings as defined in claim 1.

7. The compound according to claim 1, having any of the formulae (III-1) to (III-8):

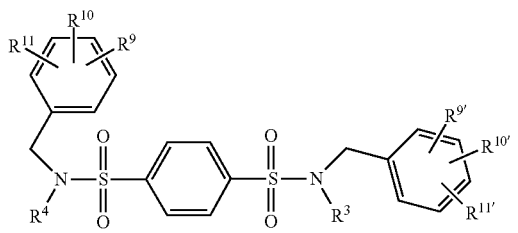

(III-1)

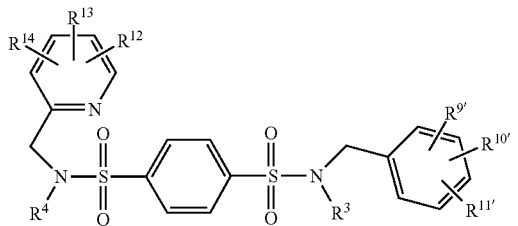

(III-2)

-continued
(III-3)
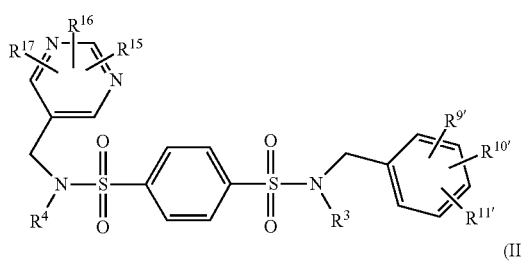
(III-4)
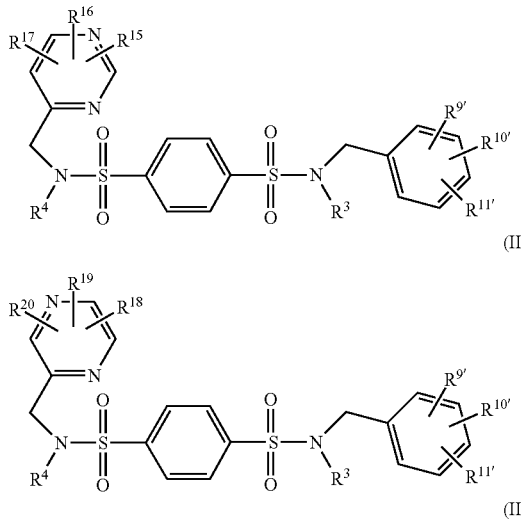
(III-5)
(III-6)
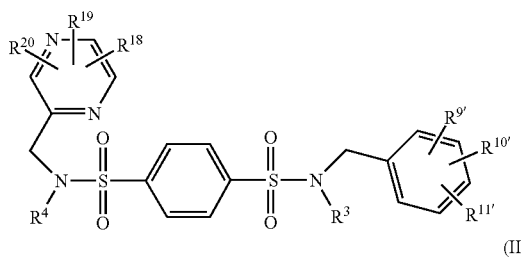
(III-7)
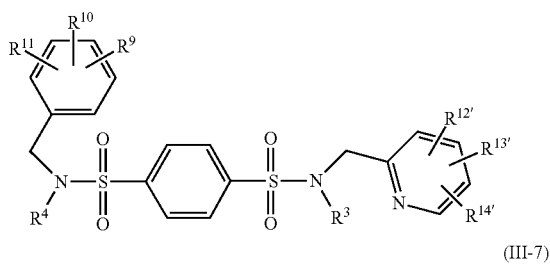
(III-8)
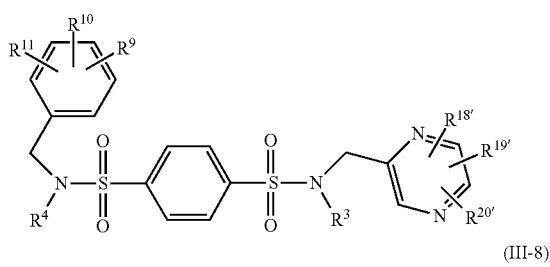
wherein
R³ represents —R⁷;
R⁴ represents —CH₂—R⁸, or —CH₂—CH₂—R⁸;
R⁷ represents
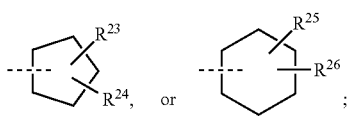
R⁸ represents
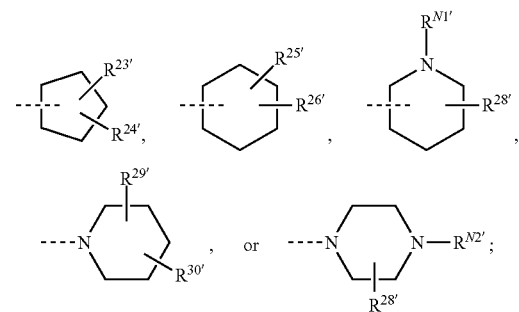
R⁹-R²⁰, R⁹'-R²⁰', R²³-R²⁶, R²³'-R²⁶', R²⁸'-R³⁰' and R^{N1'}-R^{N2'} have the same meanings as defined in claim 1.
8. The compound according to claim 1, having of the formula (V)
(V)
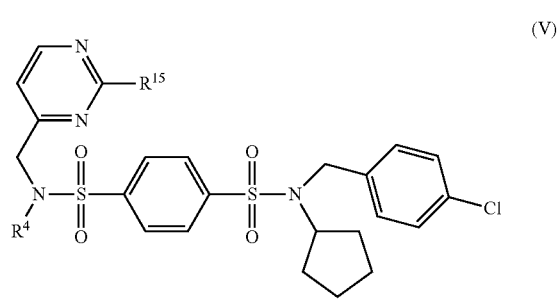
wherein
R⁴ represents
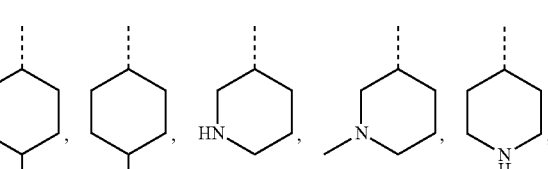
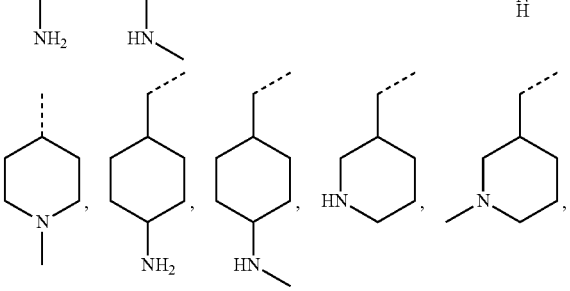

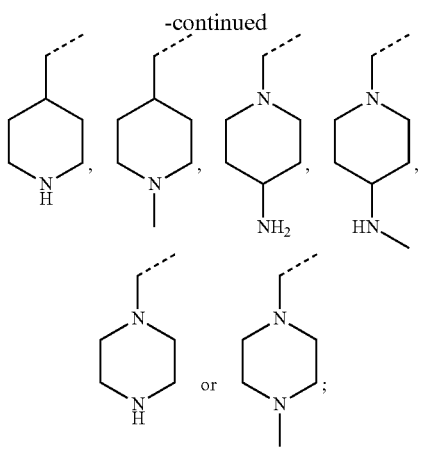

$R^{15}$ represent —H, —F, —Cl, —Br, —CH$_3$, —CH$_2$F, —CHF$_2$, —CF$_3$, —CH$_2$Cl, —OCHF$_2$, —OCF$_3$, —COOH, —COOCH$_3$, —NH$_2$, —NHCH$_3$, —CONH$_2$, —CONHCH$_3$, —NHSO$_2$CH$_3$, —NHSO$_2$CF$_3$, —SO$_2$NH$_2$, —SO$_2$NHCH$_3$, or NHSO$_2$CF$_3$.

9. The compound according to claim 1, selected from the group consisting of:

Compound 02: N1-(5-amino-2-bromobenzyl)-N4-(4-chlorobenzyl)-N4-cyclopentyl-N1-(piperidin-4-ylmethyl)benzene-1,4-disulfonamide, Compound 04: tert-butyl 4-(((N-benzyl-4-(N-cyclopentyl-N-(3,5-dibromobenzyl)sulfamoyl)phenyl)sulfonamido)methyl)piperidine-1-carboxylate, Compound 05: N1-((5-bromo-2-(methylamino)pyrimidin-4-yl)methyl)-N4-(4-chlorobenzyl)-N1-(cyclohexylmethyl)-N4-cyclopentylbenzene-1,4-disulfonamide, Compound 06: N1-benzyl-N4-(4-chlorobenzyl)-N4-cyclopentyl-N1-((1-methylpiperidin-4-yl)methyl)benzene-1,4-disulfonamide, Compound 09: N1-benzyl-N4-(4-chlorobenzyl)-N1-(cyclohexylmethyl)-N4-cyclopentylbenzene-1,4-disulfonamide, Compound 10: N1-benzyl-N4-(4-chlorobenzyl)-N4-cyclopentyl-N1-(2-(piperazin-1-yl)ethyl)benzene-1,4-disulfonamide, Compound 11: N1-(4-chlorobenzyl)-N1-cyclopentyl-N4-(piperidin-4-ylmethyl)-N4-(pyrazin-2-ylmethyl)benzene-1,4-disulfonamide, Compound 12: N1-benzyl-N4-((5-chloropyrazin-2-yl)methyl)-N4-cyclopentyl-N1-(piperidin-4-ylmethyl)benzene-1,4-disulfonamide, Compound 16: N1-(4-chlorobenzyl)-N1-cyclopentyl-N4-((2-(methylamino)pyrimidin-4-yl)methyl)-N4-(piperidin-4-ylmethyl)benzene-1,4-disulfonamide, Compound 17: N1-benzyl-N4-(3-bromobenzyl)-N4-cyclopentyl-N1-(piperidin-4-ylmethyl)benzene-1,4-disulfonamide, Compound 18: N1,N4-dibenzyl-N1,N4-bis(piperidin-4-ylmethyl)benzene-1,4-disulfonamide, Compound 19: N1-(4-aminocyclohexyl)-N4-(4-chlorobenzyl)-N4-cyclopentyl-N1-((2-(methylamino)pyrimidin-4-yl)methyl)benzene-1,4-disulfonamide, Compound 20: N1-(4-chlorobenzyl)-N4-(cyclohexylmethyl)-N1-cyclopentyl-N4-((2-(methylamino)pyrimidin-4-yl)methyl)benzene-1,4-disulfonamide, Compound 21: 4-(((4-(N-(4-chlorobenzyl)-N-cyclopentylsulfamoyl)-N-(piperidin-4-ylmethyl)phenyl)sulfonamido)methyl)-2-(methylamino)benzoic acid, Compound 22: 2-amino-4-(((4-(N-(4-chlorobenzyl)-N-cyclopentylsulfamoyl)-N-(piperidin-4-ylmethyl)phenyl)sulfonamido)methyl)benzoic acid, Compound 23: methyl 2-amino-4-(((4-(N-(4-chlorobenzyl)-N-cyclopentylsulfamoyl)-N-(piperidin-4-ylmethyl)phenyl)sulfonamido)methyl)benzoate, Compound 24: N1-benzyl-N4-(3-bromo-5-(tert-butyl)benzyl)-N4-cyclopentyl-N1-(piperidin-4-ylmethyl)benzene-1,4-disulfonamide, Compound 25: N1-benzyl-N4-(3-bromo-5-(trifluoromethyl)benzyl)-N4-cyclopentyl-N1-(piperidin-4-ylmethyl)benzene-1,4-disulfonamide, Compound 26: N1-benzyl-N4-(4-chlorobenzyl)-N4-cyclopentyl-N1-(piperidin-3-ylmethyl)benzene-1,4-disulfonamide, Compound 27: N1-(4-chlorobenzyl)-N1-cyclopentyl-N4-(piperidin-4-ylmethyl)-N4-(pyrimidin-5-ylmethyl)benzene-1,4-disulfonamide, Compound 34: N1-(2-bromobenzyl)-N4-(4-chlorobenzyl)-N1-(cyclohexylmethyl)-N4-cyclopentylbenzene-1,4-disulfonamide, Compound 35: N1-(3-bromobenzyl)-N4-(4-chlorobenzyl)-N1-(cyclohexylmethyl)-N4-cyclopentylbenzene-1,4-disulfonamide, and Compound 44: N1-benzyl-N4-(4-chlorobenzyl)-N4-cyclopentyl-N1-(piperidin-4-ylmethyl)benzene-1,4-disulfonamide.

10. A method for treating a cancer in a patient, comprising administering to said patient a therapeutically effective amount of at least one compound according to claim 1, wherein the cancer is selected from the group consisting of colorectal cancer, pancreatic cancer, and lung cancer.

11. A pharmaceutical composition comprising at least one compound according to claim 1 together with at least one pharmaceutically acceptable carrier, excipient and/or diluent.

* * * * *